(12) United States Patent
Dai et al.

(10) Patent No.: US 12,296,037 B2
(45) Date of Patent: May 13, 2025

(54) FUSION PROTEINS FOR HYDROXYLATING AMINO ACIDS AND PRODUCTS

(71) Applicant: HTL Biotechnology Innovation Inc., Nutley, NJ (US)

(72) Inventors: Lixin Dai, Livingston, NJ (US); Poonam Srivastava, Union City, NJ (US)

(73) Assignee: HTL BIOTECHNOLOGY INNOVATION, INC., Nutley, NJ (US)

( * ) Notice: Subject to any disclaimer, the term of this patent is extended or adjusted under 35 U.S.C. 154(b) by 947 days.

(21) Appl. No.: 17/269,123

(22) PCT Filed: Aug. 16, 2019

(86) PCT No.: PCT/US2019/046883
§ 371 (c)(1),
(2) Date: Feb. 17, 2021

(87) PCT Pub. No.: WO2020/037243
PCT Pub. Date: Feb. 20, 2020

(65) Prior Publication Data
US 2021/0308031 A1 Oct. 7, 2021

Related U.S. Application Data

(60) Provisional application No. 62/719,419, filed on Aug. 17, 2018.

(51) Int. Cl.
| | |
|---|---|
| *A61K 8/66* | (2006.01) |
| *A61K 8/65* | (2006.01) |
| *A61K 8/9728* | (2017.01) |
| *A61Q 19/00* | (2006.01) |
| *C12N 1/16* | (2006.01) |
| *C12N 9/02* | (2006.01) |
| *C12R 1/84* | (2006.01) |

(52) U.S. Cl.
CPC .................. *A61K 8/66* (2013.01); *A61K 8/65* (2013.01); *A61K 8/9728* (2017.08); *A61Q 19/00* (2013.01); *C12N 1/165* (2021.05); *C12N 9/0071* (2013.01); *C07K 2319/00* (2013.01); *C12R 2001/84* (2021.05); *C12Y 114/11002* (2013.01)

(58) Field of Classification Search
CPC .......... A61K 8/66; A61K 8/65; A61K 8/9728; A61Q 19/00; C12N 1/165; C12N 9/0071; C12N 1/16; C07K 2319/00; C12R 2001/84; C12Y 114/11002; Y02A 50/30; C12P 21/00
See application file for complete search history.

(56) References Cited

U.S. PATENT DOCUMENTS

| | | |
|---|---|---|
| 2002/0037567 A1 | 3/2002 | Kivirikko et al. |
| 2004/0146964 A1 | 7/2004 | Maxwell et al. |
| 2006/0110769 A1 | 5/2006 | Ramakrishnan et al. |
| 2006/0134629 A1 | 6/2006 | Link et al. |
| 2007/0134720 A1 | 6/2007 | Nakajima et al. |
| 2008/0081353 A1 | 4/2008 | Islam et al. |
| 2013/0203959 A1 | 8/2013 | Huang et al. |
| 2017/0283822 A1 | 10/2017 | Shoseyov et al. |
| 2020/0037243 A1 | 2/2020 | Tamura et al. |

FOREIGN PATENT DOCUMENTS

| | | |
|---|---|---|
| CA | 2536071 A1 | 3/2005 |
| CN | 1242044 A | 1/2000 |
| CN | 1871360 A | 11/2006 |
| CN | 102164949 A | 8/2011 |
| CN | 107810271 A | 3/2018 |
| CN | 108220259 A | 6/2018 |
| JP | 5008932 B2 | 8/2012 |
| WO | WO 03/025162 A2 | 3/2003 |
| WO | WO-2005019472 A1 | 3/2005 |
| WO | WO-2020037243 A1 | 2/2020 |
| WO | WO-2023194333 A1 | 10/2023 |

OTHER PUBLICATIONS

Kersteen et al. (Prot Express Purif, 2004, 38:279-291) (Year: 2004).*
Koski, M. K., et al., "Assembly of the elongated collagen prolyl 4-hydroxylase α2β2. Heterotetramer around a central α2 dimer," Biochemical Journal 474 (5): 751-769, Portland Press Limited on behalf of the Biochemical Society, United Kingdom (Mar. 2017).
Merriweather, A., et al., "Characterization and expression of enzymatically active recombinant filarial prolyl 4-hydroxylase," Molecular & Biochemical Parasitology, 116:185-197, Elsevier, Netherlands (2001).
Yuasa, K., et al., "Membrane-anchored prolyl hydroxylase with an export signal from the endoplasmic reticulum," The Plant Journal, 41:81-94, Blackwell Publishing Ltd., United States (2005).

(Continued)

*Primary Examiner* — David Steadman
*Assistant Examiner* — Joseph R Spangler
(74) *Attorney, Agent, or Firm* — HOYNG ROKH MONEGIER B.V.; David P. Owen

(57) ABSTRACT

The disclosure herein provides a fusion protein comprising prolyl 4-hydroxylase alpha subunit (P4HA) and a soluble protein partner. A fusion protein comprising prolyl 4-hydroxylase alpha subunit (P4HA1) and prolyl 4-hydroxylase beta subunit (P4HB) is provided. A microorganism including a fusion protein comprising prolyl 4-hydroxylase alpha subunit-1 (P4HA1) and prolyl 4-hydroxylase beta subunit (P4HB) is provided. The disclosure provides a microorganism including a fusion protein comprising prolyl 4-hydroxylase alpha subunit-1 (P4HA1) and prolyl 4-hydroxylase beta subunit (P4HB); and another protein to be hydroxylated. A method for providing skincare benefits including applying the fusion protein of the present disclosure on skin is also taught.

3 Claims, 10 Drawing Sheets
Specification includes a Sequence Listing.

(56) References Cited

OTHER PUBLICATIONS

Gibson, D.G., et al., "Enzymatic assembly of DNA molecules up to several hundred kilobases," *Nat. Methods.* 6(5):343-5, Nature Portfolio, Germany (2009).
Gorres, K.L., et al., "Prolyl 4-hydroxylase," *Crit. Rev. Biochem. Mol. Biol.* 45(2):106-124, Taylor & Francis Group, England (Apr. 2010).
International Search Report for International Patent Application PCT/US2019/046883, , United States Patent and Trademark Office, United States, mailed Nov. 5, 2019, 4 pages.
Kivirikko, K.I., et al., "Post-translational enzymes in the biosynthesis of collagen: intracellular enzymes," *Methods in Enzymol.*, 82:245-304 Academic Press, United States (1982).
Kivirikko,K.I., et al., "Characterization of the iron- and 2-oxoglutarate-binding sites of human prolyl 4-hydroxylase," *EMBO J.*, 16:1173-1180 EMBO Press, Germany (Mar. 1997).
Myllylä R., et al. "The role of ascorbate in the prolyl hydroxylase reaction" *Biochemical and Biophysical Research Communications* 83:441-448 Elsevier, Inc., Netherlands (Jul. 1978).
OMIM 176710 "Procollagen-Proline, 2-Oxoglutarate-4-Dioxygenase, Alpha Subunit, Isoform 1; P4HA1," retrieved from: https://omim.org/entry/176710, retrieved on Mar. 11, 2020, 3 pages.
OMIM 176790 "Procollagen-Proline, 2-Oxoglutarate-4-Dioxygenase, Beta Subunit; P4HB," retrieved from: https://omim.org/entry/176790, retrieved on Mar. 11, 2020, 4 pages.
OMIM 610339 "Prolyl 3-Hydroxylase 1; P3H1," retrieved from: https://omim.org/entry/610339, retrieved on Mar. 11, 2020, 4 pages.
Pinkas, D.M., et al., "Tunable, post-translation hydroxylation of collagen domains in *Escherichia coli,*" *ACS Chem. Biol.* 6(4):320-324, American Chemical Society, United States (Jan. 2011).
Rutschmann, C., et al., "Recombinant expression of hydroxylated human collagen in *Escherichia coli,*" *Appl. Microbiol Biotechnol.* 98:4445-4455, Springer Verlag, Germany (2014).
Shi, J., et al., "Hydroxylation of Human Type III Collagen Alpha Chain by Recombinant Coexpression with a Viral Prolyl 4-Hydroxylase in *Escherichia coli,*" *Protein J. 36*:322-331, Springer New York, United States (Jun. 2017).
Vranka, J.A., et al., "Prolyl 3-Hydroxylase 1, Enzyme Characterization and Indentification of a Novel Family of Enzymes," *Journal of Biological Chemistry 279*(22):23615-23621, American Society for Biochemistry and Molecular Biology, United States (May 2004).
Vuorela, A., et al., "Assembly of human prolyl 4-hydroxylase and type III collagen in the yeast *Pichia pastoris*: formation of a stable enzyme tetramer requires coexpression with collagen and assembly of a stable collagen requires coexpression with prolyl 4-hydroxylase," *EMBO J. 16*(22):6702-6712, Oxford University Press, United Kingdom (Nov. 1997).
Yamauchi, M., et al., "Lysine Hydroxylation and Cross-linking of Collagen," *Post-translation Modifications of Proteins. Methods of Molecular Biology 446*:95-108, Springer Nature, Switzerland (2008).

\* cited by examiner

FUSION PROTEINS FOR HYDROXYLATING AMINO ACIDS AND PRODUCTS

SEQUENCE LISTING

The present application contains a sequence listing that has been submitted electronically, and that is incorporated by reference in its entirety.

FIELD

Described herein are engineered proteins and their use in fermentation, methods for production of proteins, and methods for in vitro and in vivo hydroxylation of proteins.

BACKGROUND

There is an entire industry using microorganisms to make compounds for commercial applications. The microorganisms are typically engineered with DNA necessary to make the compounds. Examples of these microorganisms include yeast and bacteria. Compounds that are made include drugs, fragrances, flavors, proteins and the like.

Fusion proteins are created through the joining of two or more genes that originally made separate proteins. One purpose of creating fusion proteins in drug development is to impart properties from each of the "parent" proteins to the resulting fusion protein.

SUMMARY

In some embodiments, the disclosure provides a fusion protein comprising: a prolyl 4-hydroxylase alpha subunit; and a soluble protein partner. In some embodiments, the disclosure provides a fusion protein encoded by: a DNA sequence encoding a prolyl 4-hydroxylase alpha subunit; and a DNA sequence encoding a soluble protein partner.

In some embodiments, the prolyl 4-hydroxylase alpha subunit is selected from the group consisting of: prolyl 4-hydroxylase alpha subunit-1, prolyl 4-hydroxylase alpha subunit-2 and prolyl 4-hydroxylase alpha subunit-3. In some embodiments, the soluble protein partner is selected from the group consisting of: prolyl 4-hydroxylase beta subunit, Maltose binding protein, Small Ubiquitin-like Modifier, Calmodulin binding protein and Glutathione S-transferase. In certain embodiments, the prolyl 4-hydroxylase alpha subunit is from a species selected from the group consisting of bovine, human, rat, mouse, bacteria, virus, fish and *C. elegans*.

In some embodiments, the disclosure provides a fusion protein comprising: a prolyl 4-hydroxylase alpha subunit-1; and a prolyl 4-hydroxylase beta subunit. In some embodiments, the disclosure provides a fusion protein comprising: a DNA sequence encoding a prolyl 4-hydroxylase alpha subunit; and a DNA sequence encoding a prolyl 4-hydroxylase beta subunit. In certain embodiments, the prolyl 4-hydroxylase alpha subunit-1 is at the N-terminus of the fusion protein. In particular embodiments, the prolyl 4-hydroxylase beta subunit is at the C-terminus of the fusion protein.

In some embodiments, the disclosure provides a fusion protein comprising: a prolyl 4-hydroxylase alpha subunit-1; and a prolyl 4-hydroxylase beta subunit, wherein the prolyl 4-hydroxylase alpha subunit-1 is at the N-terminus of the fusion protein and the prolyl 4-hydroxylase beta subunit is at the C-terminus of the fusion protein.

In certain embodiments, the prolyl 4-hydroxylase alpha subunit is from a species selected from the group consisting of bovine, human, rat, mouse, bacteria, virus, fish and *C. elegans*. In some embodiments, the prolyl 4-hydroxylase alpha subunit-1 is encoded for by the nucleic acid of SEQ ID NO: 1 and the prolyl 4-hydroxylase beta subunit is encoded for by the nucleic acid of SEQ ID NO: 2.

In some embodiments, the disclosure provides a microorganism comprising any fusion protein disclosed herein. In some embodiments, the disclosure provides a microorganism comprising: a fusion protein comprising a prolyl 4-hydroxylase alpha subunit-1 and prolyl 4-hydroxylase beta subunit. In some embodiments, the disclosure provides a microorganism comprising: a fusion protein comprising a prolyl 4-hydroxylase alpha subunit-1 located at the N-terminus and a prolyl 4-hydroxylase beta subunit located at the C-terminus. In some embodiments, the disclosure provides a microorganism comprising: a fusion protein comprising a prolyl 4-hydroxylase alpha subunit-1 and a prolyl 4-hydroxylase beta subunit; and a second protein to be hydroxylated. In certain embodiments, the microorganism is selected from the group consisting of *Bacillus, Escherichia coli*, and filamentous fungi. In some embodiments, the microorganism is a yeast. In specific embodiments, the second protein is selected from the group consisting of: collagen, recombinant collagen, collagen-like proteins and the like. In some embodiments, the prolyl 4-hydroxylase alpha subunit-1 is encoded for by the nucleic acid of SEQ ID NO: 1 and the prolyl 4-hydroxylase beta subunit is encoded for by the nucleic acid of SEQ ID NO: 2

In some embodiments, the disclosure provides a method for providing skincare benefits to skin of an individual comprising: applying a fusion protein disclosed herein onto the skin. In certain embodiments, the fusion protein is formulated into a composition selected from the group consisting of a cream, a lotion, an ointment, a gel, a serum and combinations thereof. In some embodiments, the skincare benefit is selected from the group consisting of anti-wrinkle, improve skin pigmentation, hydration, reduction of acne, prevention of acne, reduction of black heads, prevention of blackheads, reduction of stretch marks, prevention of stretch marks, prevention of cellulite, reduction of cellulite and combinations thereof. In certain embodiments, the fusion protein is combined with other skin care benefit ingredients selected from the group consisting of salicylic acid, retinol, benzoyl peroxide, vitamin C, glycerin, alpha-hydroxy acids, hydroquinone, kojic acid, hyaluronic acid and combinations thereof.

In some embodiments, the disclosure provides an in vitro method for hydroxylating a protein comprising: providing a microorganism containing a protein to be hydroxylated; providing a fusion protein disclosed herein; lysing the microorganism to create a lysate; adding a specific concentration of the fusion protein to the lysate; and incubating the lysate and the fusion protein in reaction conditions that promote the hydroxylation of the protein by the fusion protein. In some embodiments, the lysate is purified prior to adding the fusion protein. In certain embodiments, the fusion protein concentration ranges from about 0.05 µM to about 5 µM based on about 1 µM of protein to be hydroxylated. In particular embodiments, the hydroxylation takes place at a pH ranging from about 5 about to 12. In some embodiments, the hydroxylation takes place at a temperature ranging from about 16° C. to about 40° C. In certain embodiments, the hydroxylation takes places over about 30 mins to about 1 hour.

In some embodiments, the disclosure provides a method for making hydroxylated protein comprising: providing a microorganism disclosed herein; and growing the microorganism in a medium for a time sufficient to hydroxylate the second protein. In certain embodiments, the microorganism is a yeast. In a particular embodiment, the yeast is *Pichia pastoris*. In some embodiments, the microorganism is grown for about 50 hours to about 72 hours.

In some embodiments, the disclosure provides a microorganism comprising: a DNA sequence encoding a prolyl 4-hydroxylase alpha subunit; and a DNA sequence encoding a soluble protein partner.

Additional aspects and embodiments are found in the following detailed description.

FIGURES

Figure 3:
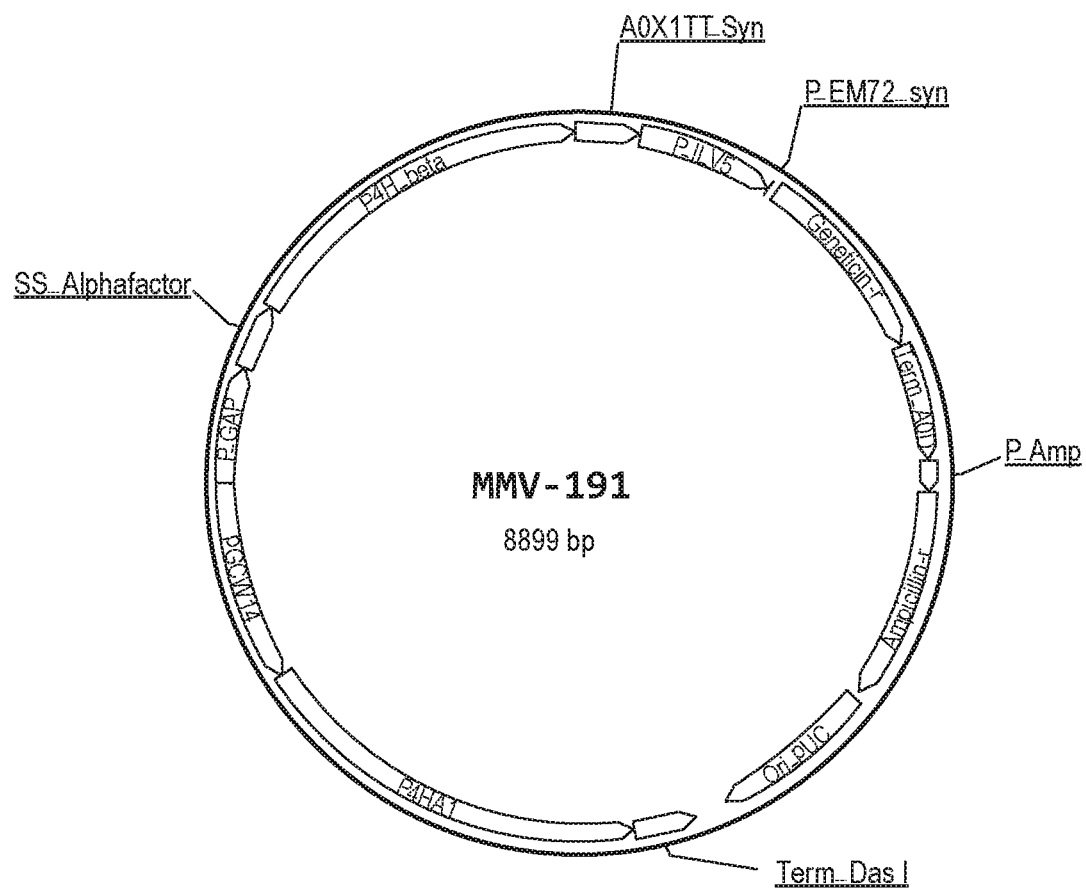

FIG. 3 MMV-191 which was used as described in Example 3 to generate *Pichia pastoris* yeast strain PP268.

Figure 4:
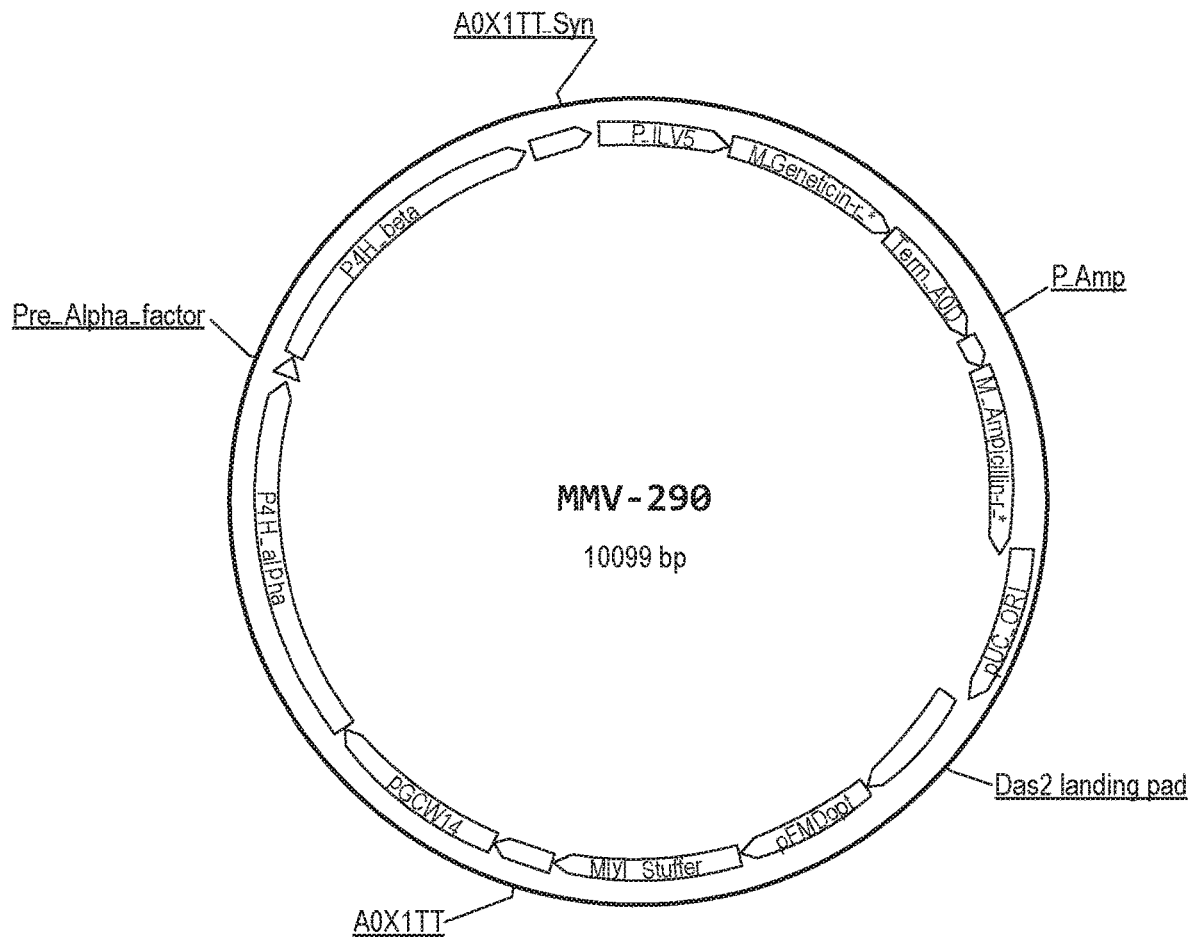

FIG. 4 shows MMV-290 vector which was produced as described in Example 1 and transformed into *Pichia pastoris* yeast strain PP153 to generate *Pichia pastoris* yeast strain PP336 and expresses a fusion protein with P4HA1 at the N-terminus and P4HB at the C-terminus with a linker sequence of "GSGSGS".

Figure 5:
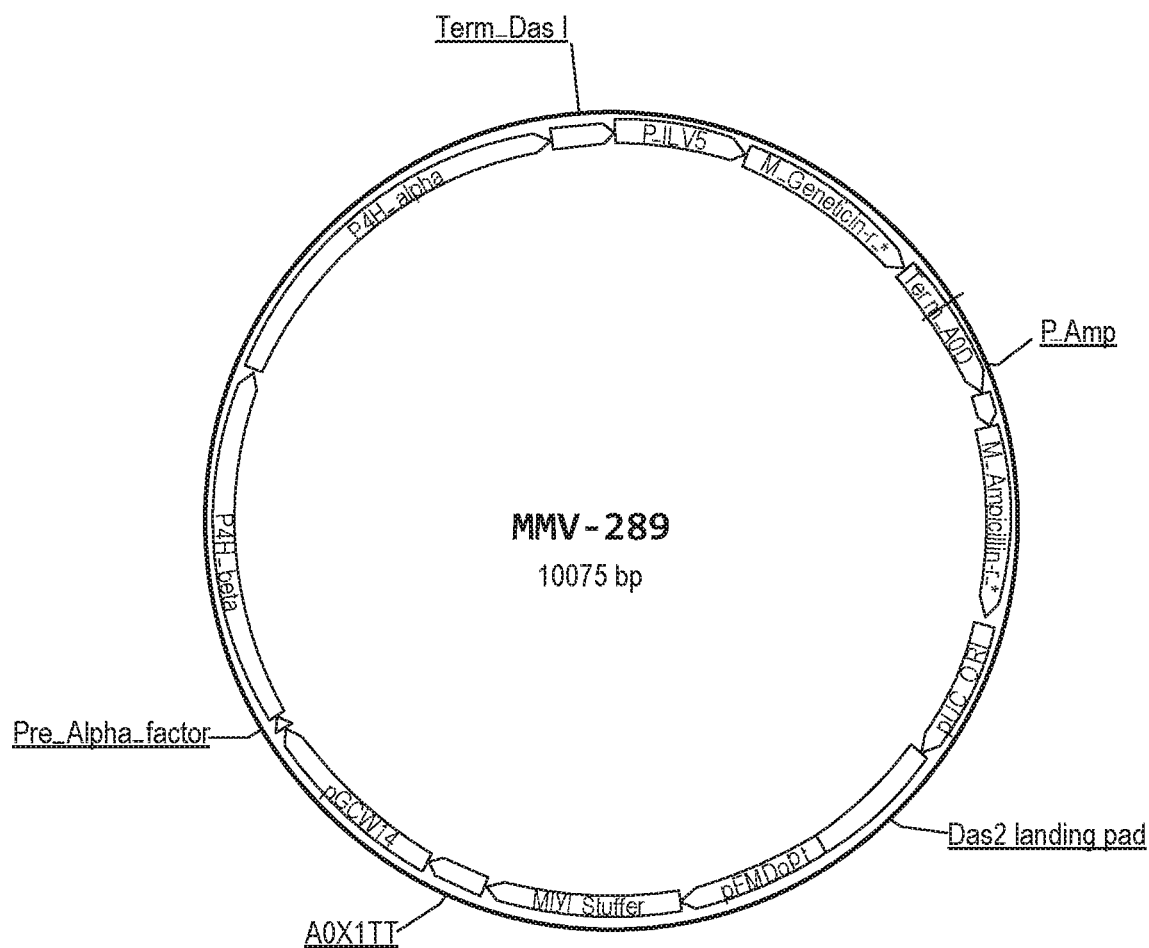

FIG. 5 shows MMV-289 vector which was produced as described in Example 2 and was transformed into *Pichia pastoris* yeast strain PP153 to generate *Pichia pastoris* yeast strain PP335 and expresses a fusion protein with P4HB at the N-terminus and P4HA1 at the C-terminus.

Figure 6:
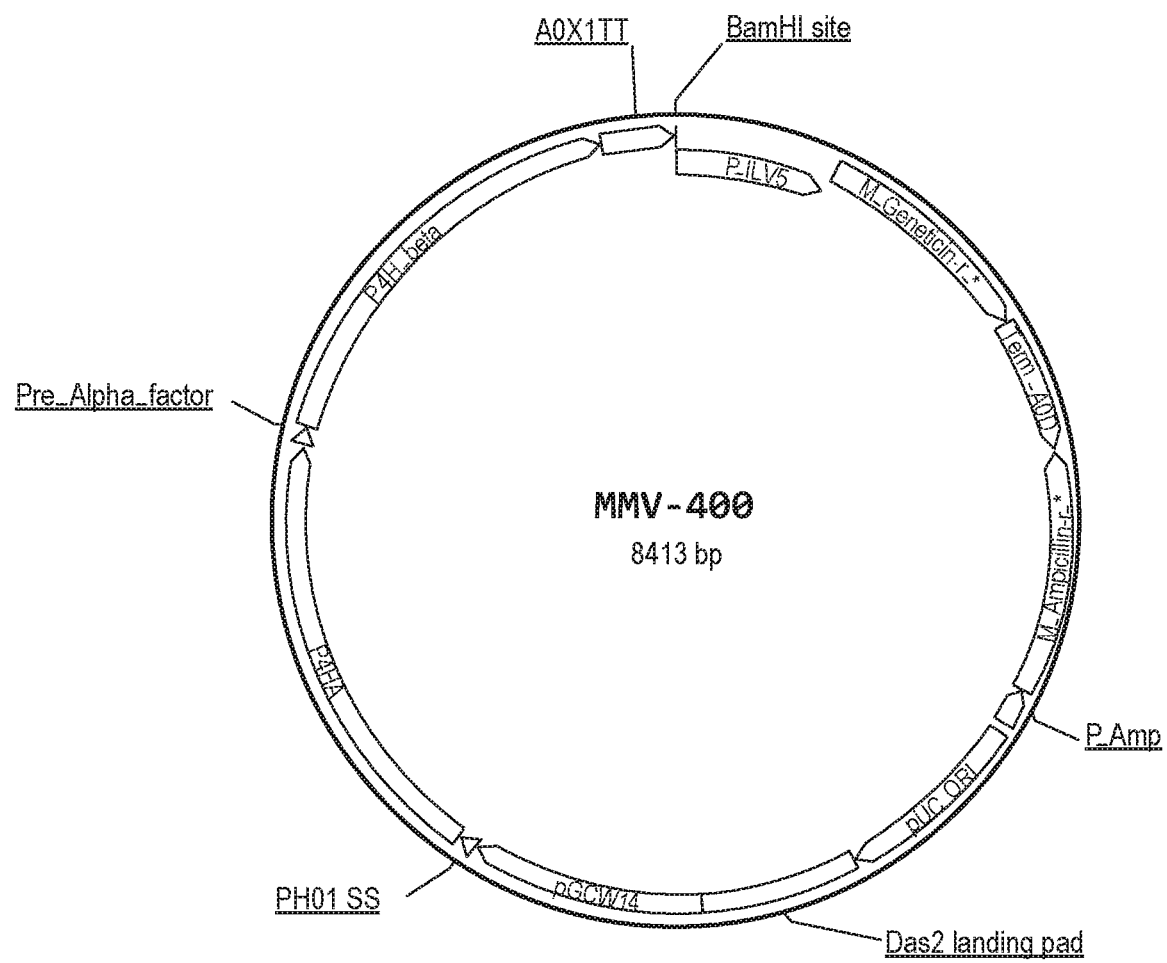

FIG. 6 shows MMV-400 vector as described in Example 4 and which contains DNA sequence for the AB fusion protein (i.e., a fusion protein with P4HA1 at the N-terminus and P4HB at the C-terminus as described in Example 3).

Figure 7:
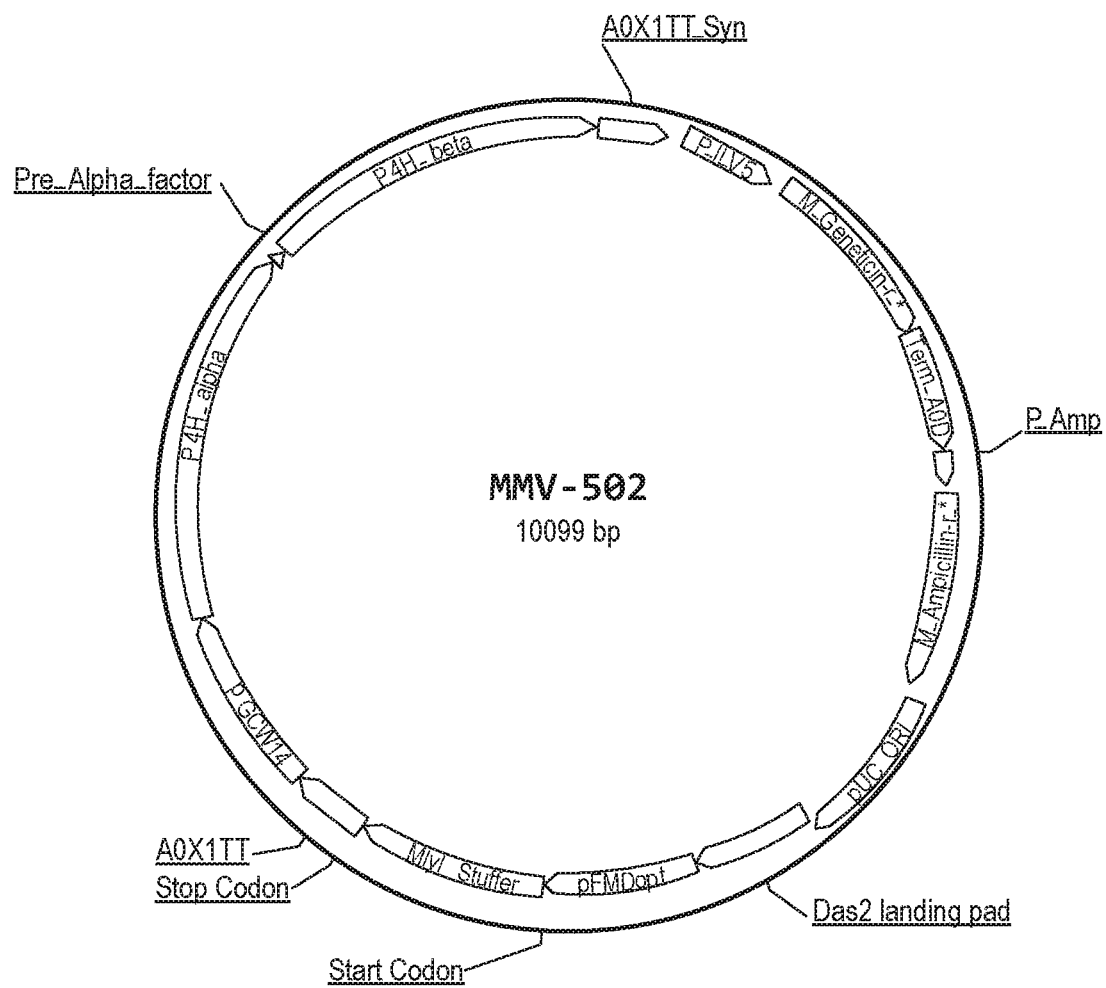

FIG. 7 shows MMV-502 vector as described in Example 5 and which contains the DNA sequence for the AB fusion protein, a nucleotide sequence representing six consecutive amino acids of Histidine (His-tag), two stop codons, and the AOX1 transcription terminator.

Figure 8:
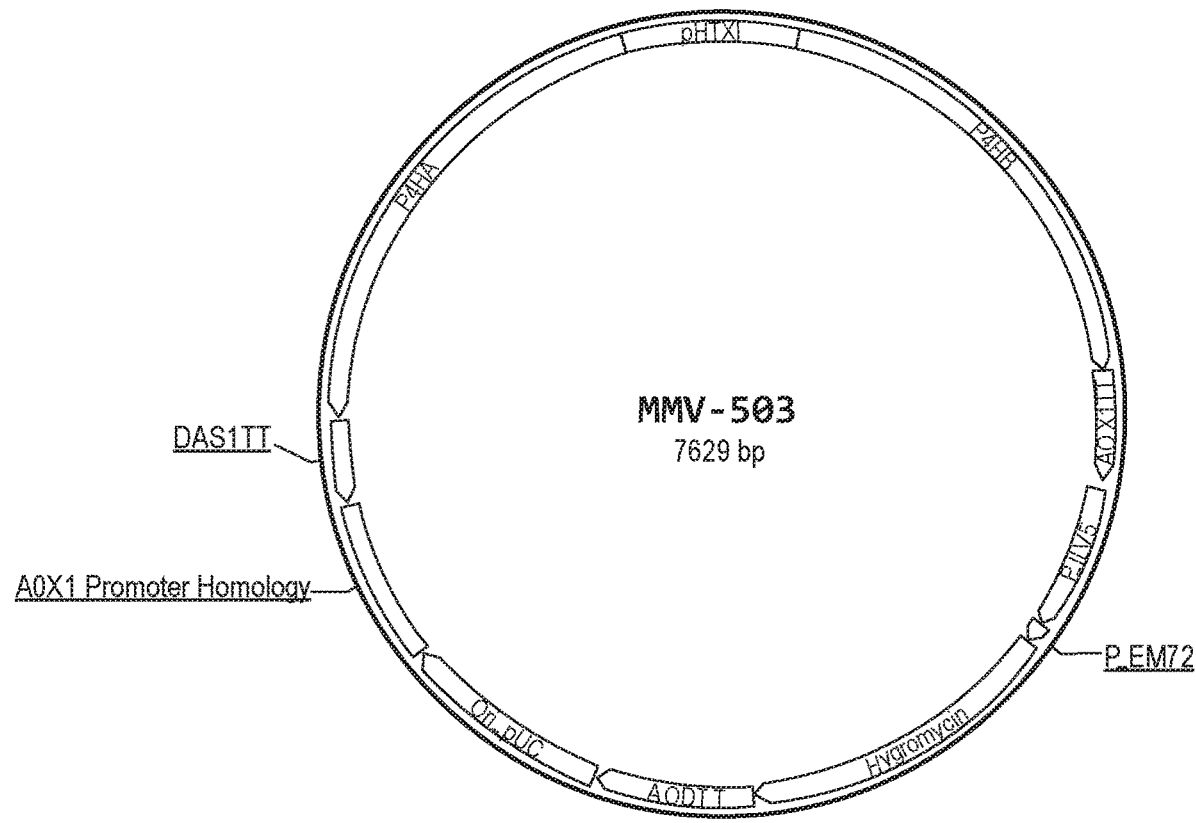

FIG. 8 shows MMV-503 vector as described in Example 5 and which contains the C-terminus of the P4HB subunit protein, a nucleotide sequence presenting six consecutive amino acids of Histidine (His-tag), two stop codons, and the AOX1 transcription terminator.

Figure 9:
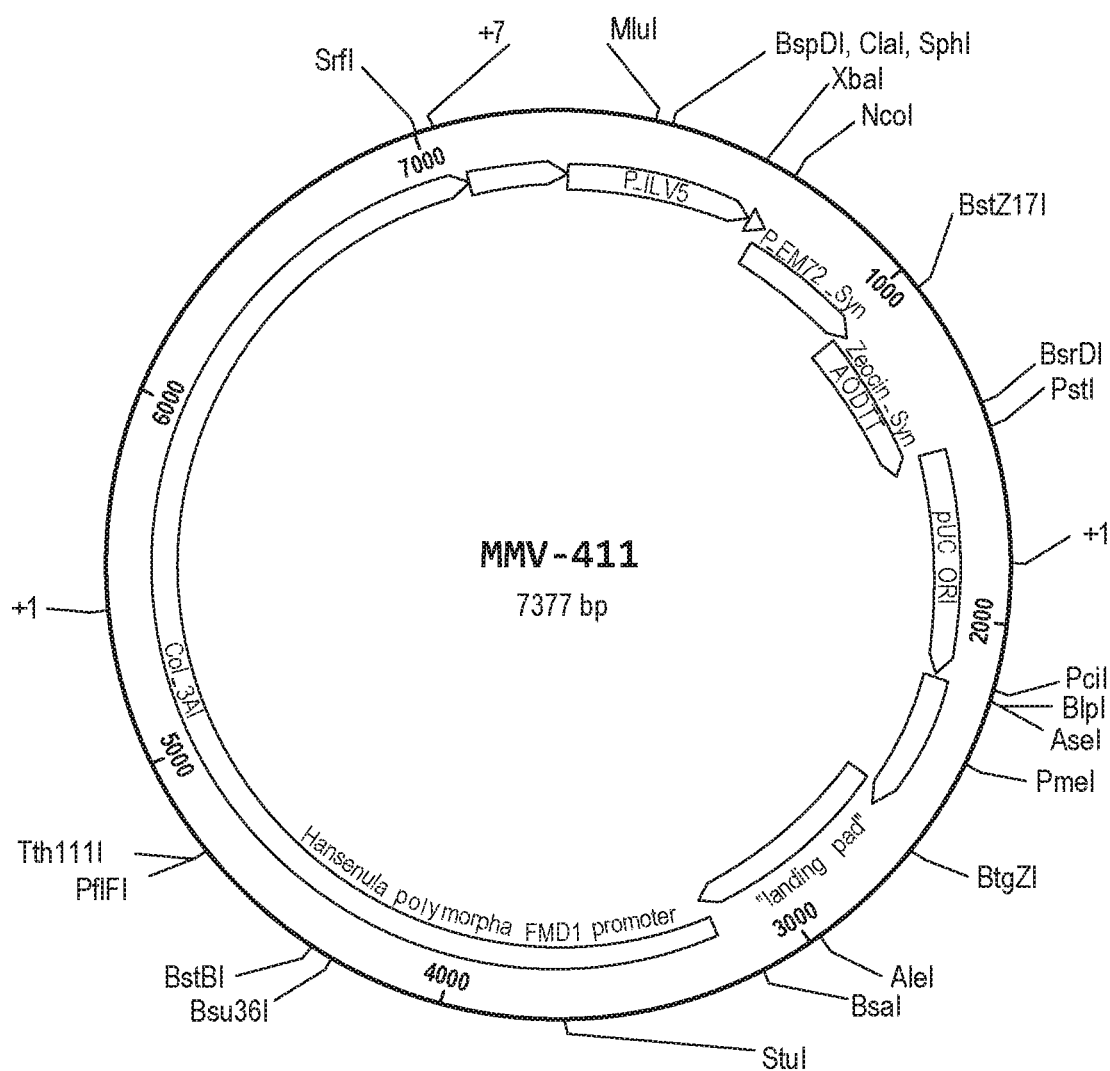

FIG. 9 shows the MMV411 vector used in Example 7.

Figure 10:
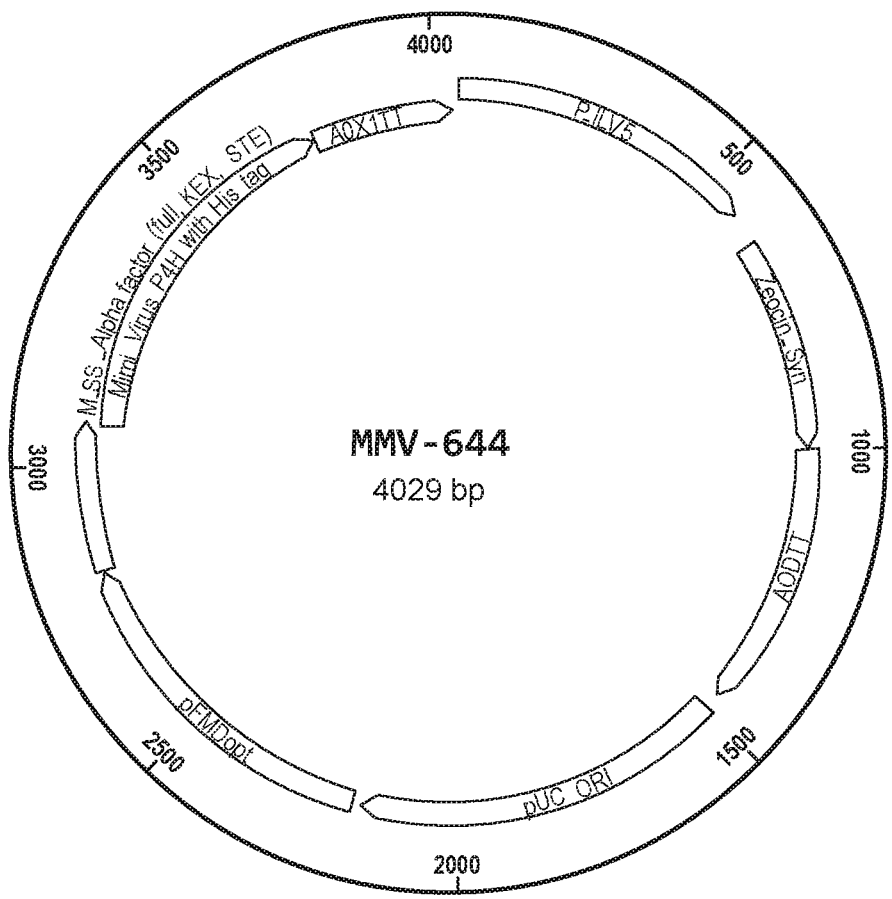

FIG. 10 shows vector MMV-644 as described in Example 1.

DETAILED DESCRIPTION

All methods and materials similar or equivalent to those described herein can be used in the practice or testing of the present disclosure, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

In some embodiments, the present disclosure provides a fusion protein encoded by: a DNA sequence of a prolyl 4-hydroxylase alpha subunit and a DNA sequence of a soluble protein partner. In certain embodiments, the fusion protein comprises a prolyl 4-hydroxylase alpha subunit-1 (P4HA1) and a prolyl 4-hydroxylase beta subunit (P4HB).

In certain embodiments, a monomeric prolyl 4-hydroxylase alpha subunit can be used in any embodiment in place of a fusion protein disclosed herein.

The P4HA and P4HB genes encode components of prolyl-4-hydroxylase, a key enzyme in collagen synthesis composed of two identical alpha subunits and two beta subunits (heterotetramer). The P4HA encoded protein is one of several different types of alpha subunits and provides the major part of the catalytic site of the active enzyme. See, e.g., *Crit Rev Biochem Mol Biol.* 45(2): 106-124 (2010). P4HA comprises three domains: the dimerization domain, the substrate binding domain and the catalytic domain. In some embodiments, the prolyl 4-hydroxylase alpha subunit is from a species selected from the group consisting of bovine, human, rat, mouse, bacteria, virus, fish and *C. elegans*. In certain embodiments, the monomeric prolyl 4-hydroxylase alpha subunit is from a species selected from the group consisting of bacteria, virus, fungus and Algae. In certain embodiments, the monomeric prolyl 4-hydroxylase alpha subunit is from mimivirus (DNA sequence: SEQ ID NO: 15; protein sequence: SEQ ID NO: 16). See, e.g., Rutschmann et al., *Appl. Microbiol Biotechnol.* 98: 4445-4455 (2014) and Shi et al. *Protein J.* 36: 322-331 (2017). In collagen and related proteins, prolyl 4-hydroxylase catalyzes the formation of 4-hydroxyproline that is important to the proper three-dimensional folding of newly synthesized procollagen chains. The P4HB protein is also known as disulfide-isomerase. It is an enzyme in humans encoded by the P4HB gene. The human P4HB gene is localized in chromosome 17q25. This protein is multifunctional unlike other prolyl 4-hydroxylase family proteins and acts as an oxidoreductase for disulfide formation, breakage, and isomerization. The activity of P4HB is tightly regulated, both dimer dissociation and substrate binding are likely to enhance its enzymatic activity during the catalysis process. In some embodiments, the P4HB is from a species selected from the group consisting of bovine, human, rat, mouse, bacteria, virus, fish and *C. elegans*.

The DNA sequences for P4HA (NCBI Ref: XP 005226443.1; UNIPROT: Q1RMU3), P4HB (Genbank: AAI46272.1; UNIPROT: P05307), P4HA3 (UNIPROT: P4HA3), and P4HA2 (UNIPROT: G3N2F2) are known and commercially available. In some embodiments, fusion proteins are made by removing the stop codon from a cDNA sequence coding for the first protein, then appending the DNA sequence of the second protein in frame through ligation or overlap extension polymerase chain reaction (PCR). The DNA sequence of the fusion protein will then be expressed by a cell as a single protein.

One technique for making a fusion protein is ligation, which is the joining of two nucleic acid fragments with the action of an enzyme. DNA fragments are joined together to create recombinant DNA molecules, such as when a foreign DNA fragment is inserted into a plasmid. The ends of DNA fragments are joined together by the formation of phosphodiester bonds between the 3'-hydroxyl of one DNA terminus with the 5'-phosphoryl of another. Another technique for making a fusion protein is overlap extension PCR, also known as splicing by overlap extension. Overlap extension PCR is used to insert specific mutations at specific points in a sequence or to splice smaller DNA fragments into a larger polynucleotide. A secretion signal sequence, such as the *Saccharomyces cerevisiae* alpha mating factor signal, can be placed in front of a monomeric prolyl 4-hydroxylase alpha subunit to secret the protein from the host into production media.

In some embodiments, fusion proteins disclosed herein may be encoded by the following combinations: the DNA sequence of prolyl 4-hydroxylase alpha subunit-1 (P4HA1) or the DNA sequence of prolyl 4-hydroxylase alpha subunit-2 (P4HA2) or the DNA sequence of prolyl 4-hydroxylase alpha subunit-3 (P4HA3) and the DNA sequence of prolyl 4-hydroxylase beta subunit (P4HB); and the DNA sequence of prolyl 4-hydroxylase alpha subunit-1 (P4HA1) or the DNA sequence of prolyl 4-hydroxylase alpha subunit-2 (P4HA2) or the DNA sequence of prolyl 4-hydroxylase alpha subunit-3 (P4HA3) and the DNA sequence of a soluble protein partner selected from: prolyl 4-hydroxylase beta subunit (P4HB), Maltose binding protein, Small Ubiquitin-like Modifier, Calmodulin binding protein, Glutathione S-transferase and the like. The active prolyl-4-hydroxylase complex may include P4H subunits from species such as bovine, human, rat, mouse, C. elegans and the like. In one embodiment, the fusion protein comprises P4HA1 and P4HB.

When making a fusion protein described herein, it is possible to make a protein with P4HA or P4HB at the N-terminus. We have surprisingly found that the fusion protein with P4HA at the N-terminus forms a functioning hydroxylating enzyme in yeast in the presence of free proline, whereas the fusion protein with P4HB at the N-terminus doesn't form a functioning hydroxylating enzyme in yeast. In certain embodiments, the fusion protein has P4HA at the N-terminus and a second protein at the C-terminus. In some embodiments, the fusion protein has with P4HA at the N-terminus and P4HB at the C-terminus.

The DNA of the fusion protein encoding P4HA1 and P4HB or the DNA of the monomeric prolyl 4-hydroxylase alpha subunit may be transformed or transfected into an organism. Suitable organisms include yeast, bacteria, fungi and the like. In some embodiments, the bacteria can be Bacillus or Escherichia coli. In some embodiments, the microorganism can be a filamentous fungi. In some embodiments, the organism can be yeast. In certain embodiments, the yeast can be Pichia pastoris. Typically, for functioning hydroxylating enzymes, multiple transfection/transformation reactions are required. The fusion protein described herein enables a more efficient process. The fusion protein described herein reduces the number of transformation reactions to one instead of two (e.g., one for P4HA1 and one for P4HB). If the enzymes are transformed separately, they will go through three reactions to form a tetramer in order to be an effective enzyme. A tetramer consists of, e.g., two P4HA subunits and two P4HB subunits. The three reactions are as follows: 1) a first P4HA and a first P4HB combining to form a first dimer, 2) a second P4HA and a second P4HB combining to form a second dimer, and 3) the two dimers forming a tetramer. When the enzymes are transformed separately, not all P4HAs and P4HBs will react to form the tetramer. A fusion protein will require one reaction with another fusion protein to form an effective tetramer. A benefit of the present disclosure is that the fusion proteins (two molecules) form a tetramer more efficiently than separate proteins (four proteins). Two fusion proteins will form one tetramer. Therefore, the fusion protein described herein provides a more efficient and effective hydroxylating enzyme. In some embodiments, the fusion protein can be used in a method for in vitro hydroxylation of proteins. In some embodiments, the fusion protein can be used in a method for in vivo hydroxylation of proteins.

In some embodiments, the fusion protein described herein can be used to hydroxylate proteins in vitro. Microorganisms that contain protein such as collagen may be lysed creating a lysate. The lysate may be processed to create purified proteins. The fusion protein may be added to purified samples of protein or added to the lysate. In some embodiments, co-factors for the hydroxylation reaction can include one or more of: ascorbic acid, sodium ascorbate, or iron (II), for example $FeSO_4$. In certain embodiments, the substrate for the hydroxylation reaction can be selected from: AKG, molecular collagen and molecular oxygen. In some embodiments, bovine serum albumin and/or catalase can be added to the reaction to help with efficient hydroxylation. The hydroxylation reaction may be performed at a temperature ranging from about 16° C. to about 40° C., for example about 32° C. In some embodiments, the hydroxylation reaction can be performed at about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C. or about 40° C. The amount of fusion protein added lysate may range from about 0.05 µM to about 5 µM based on 1 µM of protein to be hydroxylated, for example about 2.5 µM. In some embodiments, the amount of fusion protein added lysate can be about 0.05 µM, about 0.1 µM, about 0.15 µM, about 0.2 µM, about 0.25 µM, about 0.3 µM, about 0.35 µM, about 0.4 µM, about 0.5 µM, about 0.6 µM, about 0.7 µM, about 0.8 µM, about 0.9 µM, about 1.0 µM, about 1.1 µM, about 1.2 µM, about 1.3 µM, about 1.4 µM, about 1.5 µM, about 1.6 µM, about 1.7 µM, about 1.8 µM, about 1.9 µM, about 2.0 µM, about 2.5 µM, about 3.0 µM, about 3.5 µM, about 4.0 µM, about 4.5 µM or about 5 µM based on 1 µM of protein to be hydroxylated The amount of fusion protein added to the purified protein may range from 0.05 µM to 5 µM based on 1 µM of protein to be hydroxylated, for example 2.5 µM. In some embodiments, the amount of fusion protein added to the purified protein can be about 0.05 µM, about 0.1 µM, about 0.15 µM, about 0.2 µM, about 0.25 µM, about 0.3 µM, about 0.35 µM, about 0.4 µM, about 0.5 µM, about 0.6 µM, about 0.7 µM, about 0.8 µM, about 0.9 µM, about 1.0 µM, about 1.1 µM, about 1.2 µM, about 1.3 µM, about 1.4 µM, about 1.5 µM, about 1.6 µM, about 1.7 µM, about 1.8 µM, about 1.9 µM, about 2.0 µM, about 2.5 µM, about 3.0 µM, about 3.5 µM, about 4.0 µM, about 4.5 µM or about 5 µM based on 1 µM of protein to be hydroxylated. In some embodiments, the hydroxylation takes place at a pH ranging from about 5 to about 12, for example about 7.5. In some embodiments, the pH can be about 5.0, about 5.5, about 6, about 6.5, about 7, about 7.5, about 8, about 8.5, about 9.0, about 9.5, about 10.0, about 10.5, about 11, about 11.5 or about 12. In some embodiments, the hydroxylation takes place over about 30 mins to about 5 hours, for example about 1 hour. In some embodiments, the hydroxylation takes place over about 30 minutes, about 45 minutes, about 1 hour, about 1.5 hours, about 2 hours, about 2.5 hours, about 3 hours, about 3.5 hours, about 4 hours, about 4.5 hours, or about 5 hours. After the reaction, the fusion protein may be inactivated by adding an acid to lower the pH of the solution to 4 or adding 50%-80% methanol. In embodiments, the in vitro hydroxylation can be performed using any method disclosure in U.S. Pat. No. 7,932,053, wherein is incorporated herein by reference in its entirety.

Alternatively, the DNA sequence of the fusion protein can be transfected into a microorganism and utilized to hydroxylate proteins intracellularly/in vivo. The transfected microorganism can be grown in a media appropriate for the particular microorganism under conditions well known to one of ordinary skill in the art. In some embodiments, suitable media for the reaction can be, for example, LB (Lysogeny broth) for *E. coli*, BMGY (Buffered Glycerol-complex Medium) for *Pichia*, YPD (yeast extract peptone dextrose) for *Pichia* or HMP (Sodium hexametaphosphate) for *Pichia*. The temperature of the media can range from about 16° C. to about 42° C. In some embodiments, the temperature of the media can be about 16° C., about 18° C., about 20° C., about 22° C., about 24° C., about 26° C., about 28° C., about 29° C., about 30° C., about 31° C., about 32° C., about 33° C., about 34° C., about 35° C., about 36° C., about 38° C., about 40° C., or about 42° C. In some embodiments, the microorganism is *Pichia*, and the temperature of the media may range from about 28° C. to about 36° C., for example about 32° C. In some embodiments, the temperature of the media can be about 28° C., about 29° C., about 30° C., about 31° C., about 32° C., about 33° C., about 34° C., about 35° C. or about 36° C. The microorganism can be grown for a time ranging from about 50 hours to about 72 hours, for example about 68 hours. In some embodiments, the microorganism can be grown for about 50 hours, about 51 hours, about 52 hours, about 53 hours, about 54 hours, about 55 hours, about 56 hours, about 57 hours, about 58 hours, about 59 hours, about 60 hours, about 61 hours, about 62 hours, about 63 hours, about 64 hours, about 65 hours, about 66 hours, about 67 hours, about 68 hours, about 69 hours, about 70 hours, about 71 hours, or about 72 hours. In certain embodiments, the substrate for the hydroxylation reaction can be selected from the group consisting of: AKG, molecular collagen and molecular oxygen.

In some embodiments, the DNA sequence for the fusion protein can be placed in a vector along with: a DNA sequence for the fusion protein promoter; a DNA sequence for the fusion protein terminator; a DNA sequence for a selection marker, a DNA sequence for a promoter for the selection marker; a DNA sequence for a terminator for the selection marker; a DNA sequence for a replication origin selected from one for bacteria and one for yeast; and/or a DNA sequence containing homology to the yeast genome (optional to improve efficiency when transformed into a yeast). In some embodiments, the vector has been inserted into (or episomal to) the organism. In some embodiments, the vector then can be transformed into the microorganism by methods known in the art such as electroporation.

The DNA of the fusion protein encoding prolyl 4-hydroxylase alpha subunit-1 (P4HA1) and prolyl 4-hydroxylase beta subunit (P4HB); and the DNA encoding a second protein to be hydroxylated may be transformed into a microorganism. The hydroxylation modification can take place on various amino acids, including but not limited to proline, lysine, asparagine, aspartate and histidine. Suitable proteins that can be hydroxylated include collagen and the like. In any of the embodiments, any of the methods, and/or any of the reactions described herein, a monomeric prolyl 4-hydroxylase alpha subunit can be used in place of the fusion protein.

In some embodiments, the DNA sequence for the fusion protein can be placed in a vector along with: a DNA sequence for the fusion protein promoter; a DNA sequence for the fusion protein terminator; a DNA sequence for a selection marker, a DNA sequence for a promoter for the selection marker; a DNA sequence for a terminator for the selection marker; a DNA sequence for a replication origin selected from one for bacteria and one for yeast; and/or a DNA sequence containing homology to the host organism's genome. In some embodiments, the DNA sequence for the second protein to be hydroxylated can be placed on a vector along with: a DNA sequence for the second protein promotor; a DNA sequence for the second protein terminator; a DNA sequence for a selection marker, a DNA sequence for a promoter for the selection marker; a DNA sequence for a terminator for the selection marker; a DNA sequence for a replication origin selected from one for bacteria and one for yeast; and/or a DNA sequence containing homology to the host organism's genome. In some embodiments, the two vectors are then transformed into the microorganism by methods known in the art such as electroporation.

Alternatively, in some embodiments, an all-in-one vector can be used, wherein the DNA for the fusion protein, including a promoter and a terminator; the DNA for the second protein; including a promoter and a terminator; a DNA for a selection marker, including a promoter and a terminator; and/or DNAs with homology to the organism's genome for integration into the genome are included in the all-in-one vector. The all-in-one vector then can be transformed into the microorganism by methods known in the art such as electroporation.

It is known in the art that promotors can improve the production of proteins. Promoters are DNA sequences included in the vectors. Suitable promoters for use in the present disclosure include, but are not limited to, AOX1 methanol induced promoter, pDF de-repressed promoter, pCAT de-repressed promoter, Das1-Das2 methanol induced bi-directional promoter, pHTX1 constitutive Bi-directional promoter, pGCW14-pGAP1 constitutive Bi-directional promoter and combinations thereof.

A terminator is required at the end of each open reading frame utilized in the vectors incorporated into the yeast. In some embodiments, the DNA sequence for the terminator can be inserted into the vector.

An origin of replication is necessary to initiate replication. In some embodiments, the DNA sequence for the origin of replication can be inserted into the vector.

When yeast is the microorganism, a DNA sequence containing homology to the yeast genome is necessary and can be incorporated into the vector.

Selection markers are used to select organisms that have been successfully transformed. The markers sometimes are related to antibiotic resistance. The markers may also be related to the ability to grow with or without certain amino acids (auxotrophic markers). Suitable auxotrophic markers included, but are not limited to ADE, HIS, URA, LEU, LYS, TRP and combinations thereof. In some embodiments, the DNA sequence for a selection marker can be incorporated into the vector. The present disclosure includes methods of growing cells expressing the fusion protein, expressing the fusion protein, isolating and purifying the fusion protein. The present disclosure also includes uses of the fusion protein as described herein.

Specifically, the fusion protein described herein may be useful for personal care compositions. For personal care compositions, the fusion protein may be applied to the skin. For this use, the fusion protein may be isolated or purified in its entirety or to only a certain degree (e.g., at least 25% purified, at least 50% purified, at least 65% purified, at least 75% purified, at least 85% purified, at least 90% purified, at least 95% purified, at least 96% purified, at least 97% purified, at least 98% purified, at least 99% purified or 100% purified). In other words, the fusion protein may be added to a personal care product as a purified protein or it can be added as part of the fraction from which the protein is found. The fusion protein may be made into a cream, a lotion, an ointment, a gel, a serum and the like.

The personal care compositions may provide formulations suitable for topical application to skin. The composition may further include a cosmetically-acceptable carrier. The cosmetically-acceptable carrier may comprise from about 50% to about 99%, by weight, of the composition (e.g., from about 80% to about 95%, by weight, of the composition). In some embodiments, the carrier can be about 50%, about 55%, about 60%, about 65%, about 70%, about 75%, about 80%, about 85%, about 90%, about 95%, about 96%, about 97%, about 98?, or about 99%, by weight, of the composition. The compositions may be made into a wide variety of product types that include but are not limited to liquid compositions such as lotions, creams, gels, sticks, sprays, shaving creams, ointments, cleansing liquid washes and solid bars, pastes, powders, mousses, masks, peels, make-ups, and wipes. These product types may comprise several types of cosmetically acceptable carriers including, but not limited to solutions, emulsions (e.g., microemulsions and nanoemulsions), gels, solids and liposomes). The following are non-limitative examples of such carriers. Other carriers can be formulated by those of ordinary skill in the art.

The topical compositions useful in the present disclosure can be formulated as solutions. Solutions typically include an aqueous solvent (e.g., from about 50% to about 99% or from about 90% to about 95% of a cosmetically acceptable aqueous solvent). In some embodiments, the solution can be about 50%, about 55%, about 60%, about 65%, about 70%, about 75%, about 80%, about 85%, about 90%, about 95%, about 96%, about 97%, about 98%, or about 99 of a cosmetically acceptable aqueous solvent. Topical compositions may be formulated as a solution comprising an emollient. Such compositions preferably contain from about 2% to about 50% of an emollient(s). In some embodiments, the composition can be comprised about 2%, about 3%, about 4%, about 5%, about 6%, about 7%, about 8%, about 9%, about 10%, about 12%, about 15%, about 20%, about 25%, about 30%, about 35%, about 40%, about 45%, or about 50% of an emollient(s). As used herein, "emollients" refer to materials used for the prevention or relief of dryness, as well as for the protection of the skin. A wide variety of suitable emollients are known and may be useful in the personal care compositions. See International Cosmetic Ingredient Dictionary and Handbook, eds. Wenninger and McEwen, (The Cosmetic, Toiletry, and Fragrance Assoc., Washington, D.C., 7.sup.th Edition, 1997) (hereinafter "CTFA Handbook") which contains numerous examples of suitable materials.

A lotion can be made from such a solution. Lotions typically comprise from about 1% to about 20% (e.g., from about 5% to about 10%) of an emollient(s) and from about 50% to about 90% (e.g., from about 60% to about 80%) of water. In some embodiments, the lotion can be about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% of an emollient(s). In some embodiments, the lotion can be about 50%, about 55%, about 60%, about 65%, about 70%, about 75%, or about 80% of water.

Another type of product that may be formulated from a solution can be a cream. A cream typically comprises from about 5% to about 50% (e.g., from about 10% to about 20%) of an emollient(s) and from about 45% to about 85% (e.g., from about 50% to about 75%) of water. In some embodiments, the cream can be about 5%, about 6%, about 7%, about 8%, about 9%, about 10%, about 15%, about 20%, about 25%, about 30%, about 35%, about 40%, about 45%, or about 50% of an emollient(s). In some embodiments, the cream can be about 45%, about 50%, about 55%, about 60%, about 65%, about 70%, about 75%, about 80%, or about 85% of water.

Yet another type of product that may be formulated from a solution can be an ointment. An ointment may comprise a simple base of animal or vegetable oils or semi-solid hydrocarbons. An ointment may comprise from about 2% to about 10% of an emollient(s) plus from about 0.1% to about 2% of a thickening agent(s). In some embodiments, the ointment can be about 2%, about 3%, about 4%, about 5%, about 6%, about 7%, about 8%, about 9% or about 10% of an emollient(s). In some embodiments, the ointment can be about 0.1%, about 0.2%, about 0.3%, about 0.4%, about 0.6%, about 0.8%, about 1.0%, about 1.2%, about 1.4%, about 1.6%, about 1.8% or about 2.0% of a thickening agent(s). A more complete disclosure of thickening agents or viscosity increasing agents useful herein can be found in the CTFA Handbook.

The personal care compositions may be formulated as emulsions. If the carrier can be an emulsion, from about 1% to about 10% (e.g., from about 2% to about 5%) of the carrier comprises an emulsifier(s). In some embodiments, about 1%, about 2%, about 3%, about 4%, about 5%, about 6%, about 7%, about 8%, about 9%, or about 10% of the carrier comprises an emulsifier(s). Emulsifiers may be nonionic, anionic or cationic. Suitable emulsifiers are disclosed in, for example, the CTFA Handbook.

Lotions and creams can be formulated as emulsions. Typically, such lotions comprise from 0.5% to about 5% of an emulsifier(s). Such creams would typically comprise from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care compositions, such as lotions and creams, of the oil-in-water type and water-in-oil type are well-known in the cosmetic art and are useful for the personal care compositions. Multiphase emulsion compositions, such as the water-in-oil-in-water type are also useful. In general, such single or multiphase emulsions contain water, emollients, and emulsifiers as essential ingredients.

The personal care compositions of this disclosure can also be formulated as a gel (e.g., an aqueous gel using a suitable gelling agent(s)). Suitable gelling agents for aqueous gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically comprise between about 0.1% and 5%, by weight, of such gelling agents. In some embodiments, the gel comprises about 0.1%, about 0.2%, about 0.3%, about 0.4%, about 0.5%, about 1.0%, about 1.5%, about 2.0%, about 2.5%, about 3.0%, about 3.5%, about 4.0%, about 4.5%, or about 5.0% by weight, of such gelling agents.

The personal care compositions useful in the subject disclosure may contain, in addition to the aforementioned components, a wide variety of additional oil-soluble materials and/or water-soluble materials conventionally used in compositions for use on the skin at their art-established levels.

The personal care compositions may be applied to or on skin as needed and/or as part of a regular regimen ranging from application once a week up to one or more times a day (e.g., twice a day). The amount used will vary with the age and physical condition of the end user, the duration of the treatment, the specific compound, product, or composition employed, the particular cosmetically-acceptable carrier utilized, and like factors.

The fusion protein described herein may be useful for skin care benefits in personal care applications such as anti-wrinkle, improved skin pigmentation, hydration, reduction of acne, prevention of acne, reduction of black heads, prevention of blackheads, reduction of stretch marks, prevention of stretch marks, prevention of cellulite, reduction of cellulite and the like. By improved skin pigmentation is meant either evening out skin pigmentation or reducing skin pigmentation to provide fair skin.

The fusion protein described herein may also be combined with other skin care benefit ingredients such as, but not limited to salicylic acid, retinol, benzoyl peroxide, vitamin C, glycerin, alpha-hydroxy acids, hydroquinone, kojic acid, hyaluronic acid and the like.

Collagen prolyl 4 hydroxylases contain conserved domain that is similar to prolyl hydroxylase domain proteins (PHDs) including PHD1, PHD2, PHD3, PHD4 and the like. These PHDs play a critical role regulating the hydroxylation of Hypoxia-inducible factors (HIFs). HIFs are DNA-binding transcription factors that interact with specific nuclear cofactors under hypoxia, and they transactivate a series of hypoxia-associated genes to trigger adaptive responses. Due its role in the cell, HIFs are associated with many cellular functions such as homeostasis, vascularization and anaerobic metabolism and the like. Upregulation and downregulation of HIFs in the cell can cause angiogenesis or proliferation of cancerous cells, so HIFs and prolyl hydroxylase are increasingly studied because of their therapeutic potential. Therefore, the fusion protein described herein may be applicable to prolyl hydroxylase domain proteins.

In the context of the present description, all publications, patent applications, patents and other references mentioned herein, if not otherwise indicated, are explicitly incorporated by reference herein in their entirety for all purposes as if fully set forth, and shall be considered part of the present disclosure in their entirety.

Unless otherwise defined, all technical and scientific terms used herein have the same meaning as commonly understood by one of ordinary skill in the art to which this disclosure belongs. In case of conflict, the present specification, including definitions, will control.

When an amount, concentration, or other value or parameter is given as a range, or a list of upper and lower values, this is to be understood as specifically disclosing all ranges formed from any pair of any upper and lower range limits, regardless of whether ranges are separately disclosed. Where a range of numerical values is recited herein, unless otherwise stated, the range is intended to include the endpoints thereof, and all integers and fractions within the range. It is not intended that the scope of the present disclosure be limited to the specific values recited when defining a range.

Further, unless otherwise explicitly stated to the contrary, when one or multiple ranges or lists of items are provided, this is to be understood as explicitly disclosing any single stated value or item in such range or list, and any combination thereof with any other individual value or item in the same or any other list.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but can include other elements not expressly listed or inherent to such process, method, article, or apparatus.

Further, unless expressly stated to the contrary, "or" and "and/or" refers to an inclusive and not to an exclusive. For example, a condition A or B, or A and/or B, is satisfied by any one of the following: A is true (or present) and B is false (or not present), A is false (or not present) and B is true (or present), and both A and B are true (or present).

The use of "a" or "an" to describe the various elements and components herein is merely for convenience and to give a general sense of the disclosure. This description should be read to include one or at least one and the singular also includes the plural unless it is obvious that it is meant otherwise.

The above written description provides a manner and process of making and using it such that any person skilled in this art is enabled to make and use the same, this enablement being provided in particular for the subject matter of the appended claims, which make up a part of the original description.

As used herein, the phrases "selected from the group consisting of," "chosen from," and the like include mixtures of the specified materials.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skilled in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/ elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present disclosure.

When the term "about" is used, it is used to mean a certain effect or result can be obtained within a certain tolerance, and the skilled person knows how to obtain the tolerance. When the term "about" is used in describing a value or an end-point of a range, the disclosure should be understood to include the specific value or end-point referred to. In embodiments, "about" can mean a range of up to 10% (i.e., ±10%).

Any numerical range recited herein is intended to include all sub-ranges subsumed therein.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The above description is presented to enable a person skilled in the art to make and use all fusion proteins disclosed herein, and is provided in the context of a particular application and its requirements. Various modifications to the preferred embodiments will be readily apparent to those skilled in the art, and the generic principles defined herein may be applied to other embodiments and applications without departing from the spirit and scope of the disclosure. Thus, this disclosure is not intended to be limited to the embodiments shown, but is to be accorded the widest scope consistent with the principles and features disclosed herein.

Having generally described this disclosure, a further understanding can be obtained by reference to certain specific examples, which are provided herein for purposes of illustration only, and are not intended to be limiting unless otherwise specified.

EXAMPLES

Example 1

The DNA sequences for bovine P4HA1 (SEQ ID NO: 1) and P4HB (SEQ ID NO: 2) were acquired from DNA 2.0. Polymerase chain reactions were done using the DNA sequences as templates with primers MM-1090 (SEQ ID NO: 3); MM-750 (SEQ ID NO: 4); MM-0782 (SEQ ID NO: 5), MM-0783 (SEQ ID NO: 6); MM-0784 (SEQ ID NO: 7); MM-0785 (SEQ ID NO: 8) and Gibson assembled into vector MMV290 (SEQ ID NO: 9) (Gibson D G, Young L, Chuang R Y, Venter J C, Hutchison C A, Smith H O. *Enzymatic assembly of DNA molecules up to several hundred kilobases. Nat Methods.* 2009; 6:343-5). The final vector MMV290 (FIG. 4) was confirmed by sequencing and transformed into *Pichia pastoris* yeast strain PP153 to generate strain PP336 with P4HA1 at the N-terminus and P4HB at the C-terminus.

Figure 1:
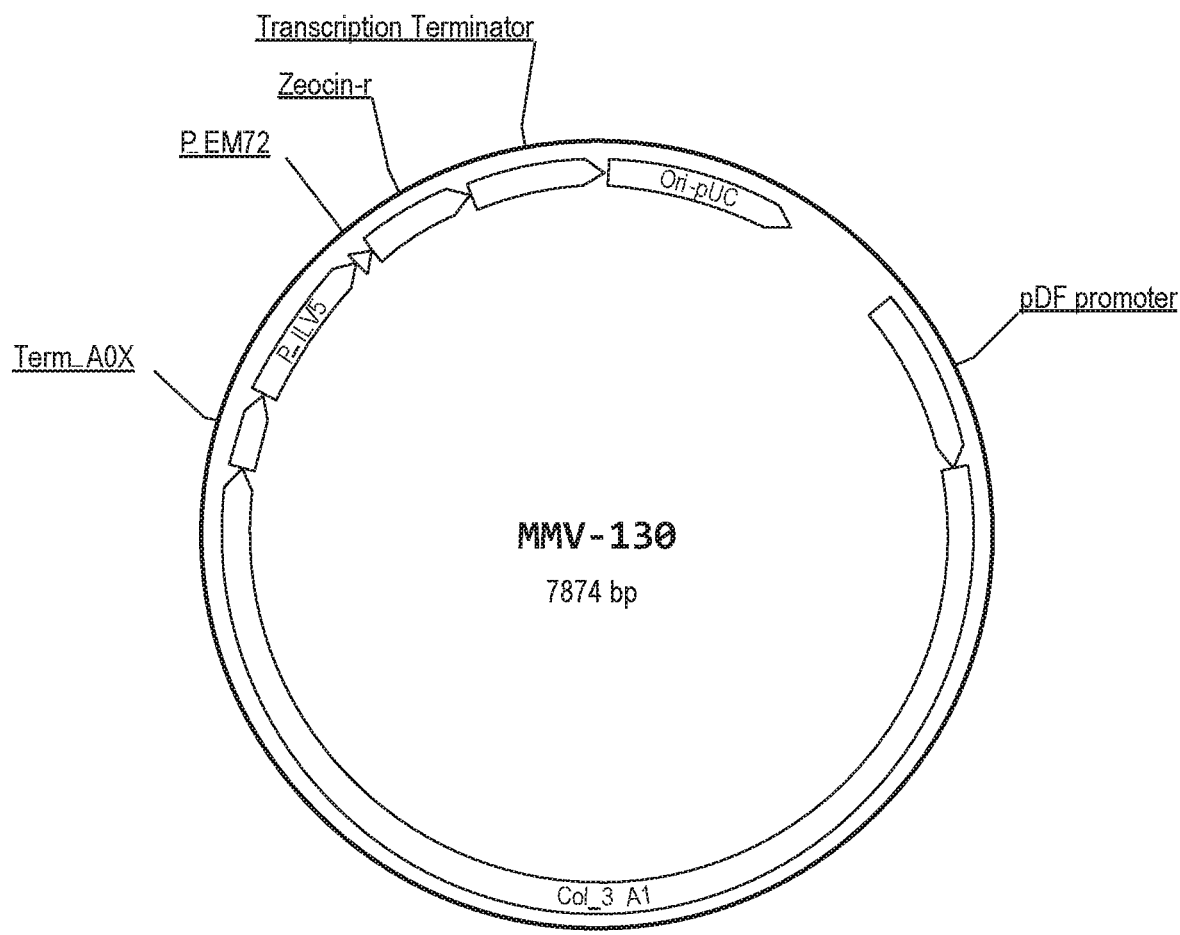
FIG. 1 shows MMV-130 which was used as described in Example 1 to generate *Pichia pastoris* yeast strain PP153.

PP153 was generated by digesting MMV-130 (FIG. 1) with Pme I and transforming into PP1. PP153 contains the wild-type collagen driven by ON promoter.

The DNA sequence of monomeric prolyl 4-hydroxylase alpha (SEQ ID NO: 15) was acquired from IDT. Polymerase chain reactions were performed using the DNA sequences as templates with primers MM-0579 (SEQ ID NO: 18); MM-0580 (SEQ ID NO: 19); MM-1569 (SEQ ID NO: 20), MM-1570 (SEQ ID NO: 21); MM-0784 (SEQ ID NO: 7) and Gibson assembled into vector MMV-644 (SEQ ID NO: 17). The final vector MMV-644 (FIG. 10) was confirmed by sequencing and transformed into *Pichia pastoris* yeast strain PP97 to generate strain PP765.

PP765 was generated by digesting MMV-644 (FIG. 10) with Swa I and transforming into PP97. PP765 contains the monomeric prolyl 4-hydroxylase with 6× His tag at C-terminus driven by pDF promoter and a secretion signal from *Saccharomyces cerevisiae* alpha mating factor.

Example 2

The DNA sequences for bovine P4HA1 and P4HB were acquired from DNA 2.0. Polymerase chain reactions were done using the DNA sequences as templates with primers MM-1090; MM-750; MM-779; MM-780; MM-781; MM-369 and Gibson assembled into vector MMV289 (SEQ ID NO: 10). The final vector MMV289 (FIG. 5) was confirmed by sequencing and transformed into yeast strain PP153 to generate strain PP335 with P4HB at the N-terminus and P4HA1 at the C-terminus.

Example 3

Strain PP336 was inoculated in a 24 well plate with 2 mL BMGY medium and grown for 48 hours at 30° C. with shaking at 900 rpm. Cells were spun down and lysed by Qiagen tissue lyser in 800 uL lysis buffer. The lysis buffer was made with 2.5 mL 1M HEPES; final concentration 50 mM, 438.3 mg NaCl; final concentration 150 mM, 5 ml Glycerol; final concentration 10%, 0.5 mL non-ionic surfactant TRITON X-100; final concentration 1%, and 42 mL Millipure water. The supernatant contained the fusion protein with P4HA1 at the N-terminus and P4HB at the C-terminus (AB fusion protein) and was loaded on SDS PAGE gel and transferred to a PVDF membrane. The fusion protein was probed with P4HB antibody in Western Blot.

Strain PP765 was inoculated in a 24 well plate with 2 mL BMGY medium and grown for 48 hours at 30° C. with shaking at 900 rpm. Cells were spun down and media was collected. The supernatant contained monomeric prolyl 4-hydroxylase was loaded on SDS PAGE gel and transferred to a PVDF membrane. The fusion protein was probed with His tag antibody in Western Blot.

The same procedure above was performed using Strain PP335 to generate the fusion protein with P4HB at the N-terminus and P4HA1 at the C-terminus (BA fusion protein).

For the AB22 fusion protein, we detected a fusion protein with a molecular weight of around 120 kDa by both coomassie staining and western blot. For the BA fusion protein, we were not able to detect the fusion protein by both methods.

Strain PP336 was inoculated in a 24 well plate with 2 mL BMGY fermentation medium and grown for 48 hours at 30° C. with shaking at 900 rpm. At the same time a bench mark yeast strain PP268 with the DNA sequences for collagen, P4HA and P4HB separately was grown under the same condition.

Figure 2:
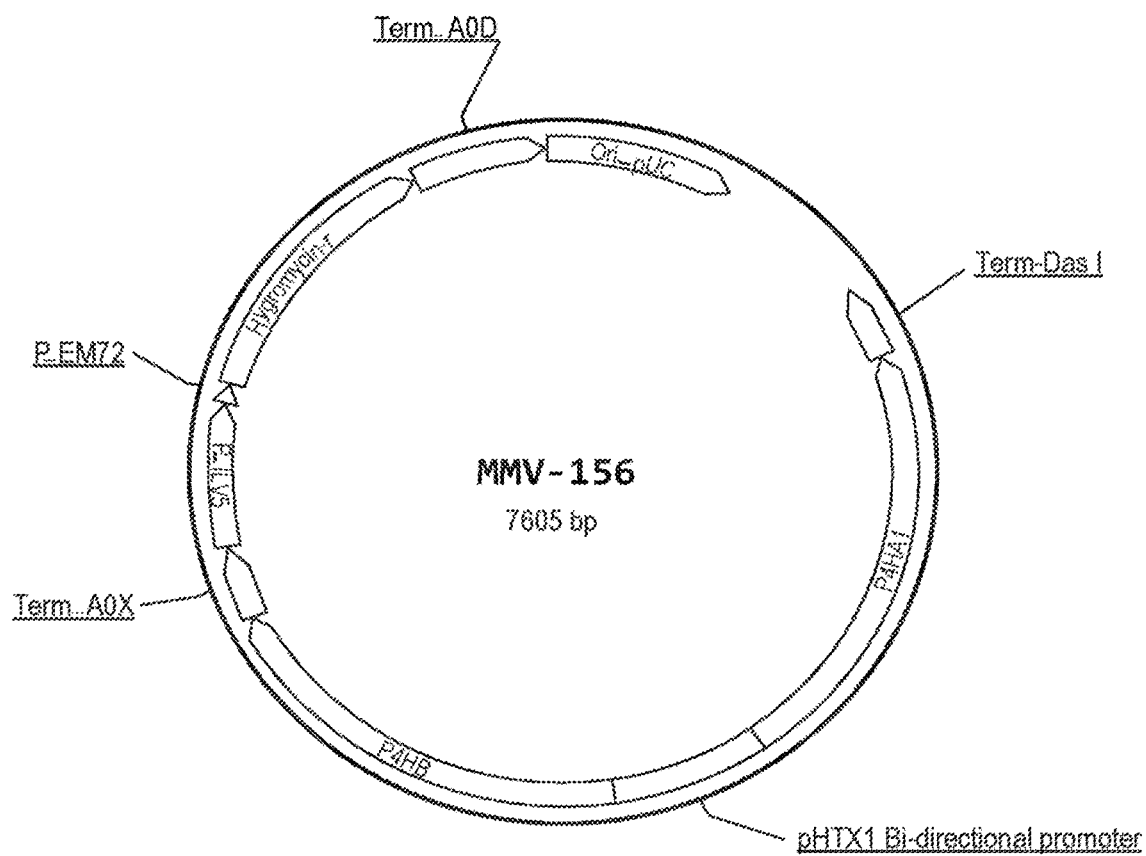
FIG. 2 shows MMV156 which was used as described in Example 3 to generate *Pichia pastoris* yeast strain PP154.

PP268 was generated by digesting MMV156 (FIG. 2) with Bam HI and transforming into PP153 to generate PP154, then MMV-191 (Figure vas digested with Bam HI and transformed into PP154 to generate PP268.

Samples PP336 and PP268 were analyzed by Pepsin assay following the procedure below to evaluate the sensitivity of collagen trimer to pepsin. PP336 will have similar pepsin resistance as PP268.

The proline hydroxylation of PP336 and PP268 was analyzed by amino acid analysis. PP336 will have similar or better proline hydroxylation to what is observed for PP268.

The pepsin assay was performed with the following procedure:
1. Before pepsin treatment perform bicinchoninic acid (BCA) assay to obtain the total protein of each sample per Thermo Scientific protocol. Normalize the total protein to the lowest concentration for all samples.
2. Put 100 uL of lysate in a microcentrifuge tube.
3. Create a master mix containing the following:
   a. 37% HCl (0.6 mL of acid per 100 mL) and
   b. Pepsin (stock is 1 mg/mL in deionized water, and final addition of pepsin should be at a 1:25 ratio pepsin:total protein (weight:weight).
   c. Based on step #1 normalization of total protein the amount of pepsin will vary for final addition, adjust using spreadsheet created.
4. After addition of pepsin, mix 3 times with pipet and allow the samples to incubate for an hour at room temperature for the pepsin reaction to take place.
5. After an hour, add 1:1 volume of LDS loading buffer containing β-mercaptoethanol to each sample and allow to incubate for 7 minutes at 70° C.
6. Then spin at 4,000 rpm for 1 minute to remove the turbidity.

Example 4

Yeast strain PP97 without the DNA for collagen and fusion protein was grown in YPD medium and 80 mM proline overnight to produce the grown culture. 20 mL YPD media and 80 mM proline was inoculated with 5 mL of the grown culture and incubated at 300 rpm at 30° C. for 1 hour. Cells were harvested at 5000 rpm 4° C. for 5 mins and washed with sterile water twice and then mixed with 10 mL of transformation buffer and incubated at 25° C. for 25 mins with 10 mM DDT. Cells were harvested and washed with cold sorbitol twice, then MMV400 (SEQ ID NO: 11 and FIG. 6)) containing the DNA for the AB fusion protein was transformed with electroporation. Cells were plated after three hours of incubation on Zeocin 500 plates with 80 mM proline present for the whole duration. The plates were incubated for two days at 30° C. and colonies were screened following the procedure described in example 3. The results showed that the fusion protein was transformed into the empty host cell in the presence of proline.

In the absence of proline in the YPD medium, there were no colony or only a few colonies formed. When these colonies were analyzed by Western Blot, all of the colonies were negative for the AB fusion protein. In the experiment with 80 mM proline added to the YPD medium, 6/6 colonies were analyzed by Western Blot and all of them were positive for the AB fusion protein.

Example 5

The vector MMV290 (FIG. 4) (SEQ ID NO: 9) was digested with BglII and MluI and Gibson assembled with an insert (SEQ ID NO: 12) encompassing on the C-terminus of the AB fusion protein, a nucleotide sequence representing six consecutive amino acids of Histidine (His-tag), two stop codons, and the AOX1 transcription terminator generating vector MMV502 (FIG. 7).

The vector MMV156 (FIG. 2) (SEQ ID NO: 13) was digested with BglII and MluI and Gibson assembled with an insert (SEQ ID NO: 12) encompassing on the C-terminus of the P4HB subunit protein, a nucleotide sequence presenting six consecutive amino acids of Histidine (His-tag), two stop codons, and the AOX1 transcription terminator generating vector MMV503 (FIG. 8).

MMV502 was transformed into PP153 generating strain PP548. This strain was cultured, lysed and assayed for protein content using various methods including Western Blot and Coomassie stained gel. The Western Blot confirmed the presence of the AB fusion protein. The Coomassie stained gel confirmed the molecular weight of the AB fusion protein with the His-tag (119 kDa). High expressing variants of the PP548 strain were grown in a shake flask and a fermenter. Once confluent, the cells were centrifuged down to pellets and washed. Cells were then lysed by a Qiagen tissue lyser in 800 μL lysis buffer. The lysis buffer was made with 2.5 mL 1M HEPES; final concentration 50 mM, 438.3 mg NaCl; final concentration 150 mM, 5 ml Glycerol; final concentration 10%, 0.5 mL non-ionic surfactant TRITON X-100; final concentration 1%, and 42 mL Millipure water. The lysate was centrifuged, and the soluble fraction was incubated with Nickel-NTA Agarose beads. The clarified lysate-bead mixture was applied to a column which retained the beads. The Nickel-NTA beads were subsequently washed with differing concentrations of imidazole, possibly including other chemicals such as 1,10-phenanthroline and EDTA. The AB fusion protein with the His tag, encoded by the plasmid MMV502, was then eluted by washing with 300 mM imidazole. These elutions were combined or kept separate and buffer exchange was performed using an AMICON Ultra 15 mL centrifugal filter column to remove residual imidazole. The AB fusion protein was then used for subsequent assays.

MMV503 was transformed into PP153 generating strain PP549. This strain was cultured, lysed and assayed for protein content using various methods including Western Blot and Coomassie stained gel. The Western Blot confirmed the presence of the P4HA and P4HB enzymes. The Coomassie stained gel confirmed the molecular weight of the P4HA (61 kDa) and P4HB (57 kDa) enzymes. High expressing variants of the PP549 strain were grown in a shake flask and a fermenter. Once confluent, the cells were centrifuged down to pellets and washed. Cells were then lysed by a Qiagen tissue lyser in 800 uL lysis buffer. The lysis buffer was made with 2.5 ml. 1M HEPES; final concentration 50 mM, 438.3 mg NaCl; final concentration 150 mM, 5 ml Glycerol; final concentration 10%, 0.5 mL non-ionic surfactant TRITON X-100; Triton X 100; final concentration 1%, and 42 mL. Millipure water. The lysate was centrifuged, and the soluble fraction was incubated with Nickel-NTA Agarose beads. The clarified lysate-bead mixture was applied to a column which retained the beads. The Nickel-NTA beads were subsequently washed with differing concentrations of imidazole, possibly including other chemicals such as 1,10-phenanthroline and EDTA. The P4HA and, P4HB with the His tag, encoded by the plasmid MMV503, was then eluted by washing with 300 mM imidazole. The elutions were combined or kept separate and buffer exchange was performed using an AMICON Ultra 15 mL centrifugal filter column to remove residual imidazole. The P4HA and P4HB proteins were then used for subsequent assays.

Example 6

The fusion protein enzymatic activity from PP548 was confirmed by a modification on a method based on the hydroxylation-coupled decarboxylation of α-ketoglutaric acid (Kivirikko, K. I. and Myllyla,R. (1982) Post-translational enzymes in the biosynthesis of collagen: intracellular enzymes. *Methods Enzymol.*, 82, 245-304; Kivirikko, K. I. and Myllyla,R. (1997) Characterization of the iron- and 2-oxoglutarate-binding sites of human prolyl 4-hydroxylase. The EMBO Journal, 16, 1173-1180). The activity measurement was based on α-ketoglutaric acid consumption over time by the AB fusion protein in a hydroxylation reaction on a (Pro-Pro-Gly)$_{10}$ peptide model substrate. The AB fusion protein amount ranges between 0.12 to 0.4 nmol per reaction. The reaction was stopped by mixing 50 µl of a sample selected at different time points ranging from 0 to 10 mins into 150 µl 30 mM o-phenylenediamine in 0.5 M HCl, in a 96 deep-well plate. The plate was put on a heat block set to 95° C. for 10 minutes to stop color formation and then cooled down on ice for 2 minutes. Then 50 ul of the sample was mixed with 30 µl 1.25 M NaOH in a black 96-well plate. The sample's fluorescence was read at emission 420, excitation 340 on a plate reader. The α-ketoglutaric acid concentration was derived from α-ketoglutaric acid standard samples performed under the same assay conditions. The α-ketoglutaric acid consumption was calculated by subtracting the sample concentration from the time zero concentration.

The P4HA and P4HB enzymatic activity from PP548 were confirmed by the same assay as above.

The results show there was less a ketoglutaric acid in the sample with the AB fusion protein than the sample with native P4HA and P4HB proteins. This shows that AB fusion protein is more active than the native P4HA and P4HB proteins.

Example 7

PP434 was generated by digesting MMV411 (SEQ ID NO: 14 and FIG. 9) with Pme I and transforming into PP97.

A single colony was inoculated in 50 mL BMGY media with constant shaking at 250 rpm and 30° C. overnight. The next day, 500 mL of fresh BMGY media was inoculated with the overnight grown culture in a 1 L Erlenmeyer flask and grown with constant shaking at 250 rpm and 30° C. for 2 days.

The PP434 cells were re-suspended (1 g wet cell weight (wcw)) in 5.667 ml phosphate buffer (50 mM, pH-7.4). The cells were lysed in a bead beater using Matrix D beads for 5 cycles with 1-minute cooling in between to generate whole cell lysate. The whole cell lysate was then placed in several 1.5 ml micro-centrifuge tubes and heated at 70° C. for 30 minutes with gentle mixing every 5 minutes. The whole cell lysate was then spun down at 4° C. for 5 minutes at 21000*g.

The supernatant was placed on ice for 10 minutes. Ni-NTA resin (0.5 ml bed volume for 1 g wcw) was equilibrated 3 times with DI water to remove ethanol by centrifuging at 800*g for 2 minutes at 4° C. The clarified lysate was added to the equilibrated Ni-NTA resin and incubate at 4° C. for 60 minutes by end over end rotation. The supernatant was collected by centrifuging at 800*g for 5 minutes at 4° C. The resin was washed with 10 column volumes of 50 mM Phosphate buffer pH-7.4, 20 mM Imidazole by centrifuging at 800*g for 2 minutes at 4° C. The resin was then washed with 10 column volumes of 50 mM Phosphate buffer pH-7.4, 250 mM Imidazole by centrifuging at 800*g for 2 minutes at 4° C. The protein was eluted 3 times with 5 ml of 50 mM Phosphate buffer pH-7.4, 500 mM Imidazole after incubation with elution buffer for 5 minutes at 4° C. (end over end rotation) by centrifuging at 800*g for 2 minutes at 4° C. The samples were analyzed (both supernatant and pellet along with whole cell lysate) on SDSPAGE. The samples were then dialyzed in 50 mM Tris, pH 8.0, 100 mM NaCl with at least one buffer exchange (dialyze in at least 100× sample volume).

Making PP547

The vector MMV363 was modified to include a 22 kD small Pre-Pro-Col3 and associated promoter pDF and terminator AOX1TT, Flag and HA tags, the DNA sequence for marker expression and associated promoter and terminator, the DNA sequence for origin(s) of replication for bacteria and yeast, and the DNA(s) sequence(s) with homology to the yeast genome for integration. Vector MMV88 was the source DNA for the Pre-Pro-Col3 domains. Vector MMV130 was the source DNA for the Col3A1 domains plus the HA and Flag tags. The total length of Col3A1 polypeptide is 190 amino acids (aa). The 3 pieces were Gibsoned together and the resulting plasmid is MMV383.

MMV383 was transformed into PP97, using the Aox landing pad for integration. The resulting *Pichia* strain it PP414. Subsequent western blots showed secretion of the small 22 kD Col3 molecule.

PP414 was transformed with MMV502, a his tagged version of MMV290 to generate PP547

Making PP635 and PP636

A single colony of PP97 was inoculated in 15 ml YPD medium having 80 mM proline and grew at 30° C. overnight with shaking (250 rpm). Next day, the volume of the medium was doubled with fresh YPD having 80 mM proline and grew for another hour at 30° C. with shaking (250 rpm). The cells were spun down at 3,500 g for 5 min; wash twice with sterile water and resuspend in 10 ml transformation buffer (10 mM Tris-Cl pH 7.5, 100 mM LiAc, 0.6 M Sorbitol), 10 mM dithiothreitol (DTT) was added and mixed well. The resuspension was incubated at room temperature for 30 min. The cells were spun down at 3,500×g for 5 min and pellet was resuspended in 5 ml ice cold 1M Sorbitol and spun down again at 3,500×g for 5 min. The wash with 5 ml of 1M Sorbitol was repeated twice. The washed pellets were resuspended in 500 µl ice cold 1M Sorbitol, 100 µl of this resuspension was aliquoted into pre-chilled 0.2 cm electroporation cuvettes. Linearized DNA sequences of MMV502 (FIG. 7) and MMV503 (FIG. 8) were added to the cells (in separate cuvettes) and mixed by pipetting. A negative control was also set up where water was added to the cell mix instead of the linearized DNA sequences. The mix was incubated on ice for 10 minutes. After incubation, electroporation was performed by pulse using *Pichia*-WU protocol (1500 v, 25 uF, 200 W), Bio-Rad Gene PULSER XCELL was used for electroporation. Bio-Rad Gene PULSER XCELL is a modular electroporation system for cell transfection. The cells were immediately transferred to 500 µl mixture of YPD and 1M Sorbitol (1:1) and incubated at 30° C. for 2 hours. A 100 µl aliquot of this 2 hours incubated culture was plated on 750 µg/ml of G418 antibiotic plates. The plates were incubated at 30° C. for two days.

Colonies that appeared on the plate after 2 days of incubation were picked up and inoculated in BMGY media containing 500 µg/ml of G418. Inoculation was done in 2 ml culture and in 24 well format. The plate was incubated at 30° C. with shaking (900 rpm) for 2 days. Each 2 ml culture was spun down, 100 mg pellets were re-suspended in 1 ml of lysis buffer (50 mM sodium phosphate, 5% glycerol and 1% EDTA, pH-7.5). Lysis was done using the tissue lyser and Y matrix beads for 15 minutes. The lysate was mixed with SDS Licor loading dye into 5:1 ratio, heated up for 10 minutes at 90° C. and loaded on 4-12% Bis-Tris gels. The gels were transferred onto PVDF membrane. A Western blot was developed using the anti-His and anti-collagen antibodies. Since the P4H is His tagged, fusion P4H shows in the red channel as 110 kDa protein whereas bidirectionally expressed P4HA/B shows up at 59 kDa in the red channel. There was no collagen band observed in the blot, confirming that the P4H plasmids were transformed without collagen. The clones that showed high expression of fusion P4H were confirmed as PP635 and clones that showed high expression of bidirectionally expressed P4H were confirmed as PP636.

Single colonies of each strain were inoculated separately in 50 mL BMGY media with constant shaking at 250 rpm and 30° C. overnight. The next day, 500 mL of fresh BMGY media was inoculated with the overnight grown culture in a 1 L Erlenmeyer flask and grown with constant shaking at 250 rpm and 30° C. for 2 days.

The cells (0.45 g wcw (wet cell weight)) were re-suspended in 0.65 ml lysis buffer (25 mM Tris, pH 7.5, 50 mM NaCl, 20 mM Imidazole) to obtain a 45% suspension. The cells were lysed in a bead beater with Matrix D beads for 5 cycles (1 minute cooling in between) to generate a lysate. The lysates were spun down to clarify the supernatant and pellet (4° C., 10 minutes, 16000*g). The clarified lysates were removed and placed on ice. The pellets were resuspended with 2 times the wcw of lysis buffer and centrifuged at 16000*g for 10 minutes to collect a more clarified lysate. The clarified lysates were combined together. Ni-NTA resin (~0.025 ml bed volume for 1 g wcw and scale up appropriately) was equilibrated in DI water three times to remove ethanol by centrifuging at 800*g for 2 minutes at 4° C. The clarified lysate was added to the equilibrated Ni-NTA resin and incubate at 4° C. overnight by end over end rotation. The supernatant was collected by centrifuging at 800*g for 5 minutes at 4° C. The resin was washed with 10 column volumes of lysis buffer containing 50 mM Imidazole by centrifuging at 800*g for 2 minutes at 4° C. The resin was then washed with 10 column volumes of 50 mM Phosphate buffer pH-7.4, 250 mM Imidazole by centrifuging at 800*g for 5 minutes at 4° C. The protein was eluted with 5 ml of lysis buffer containing 300 mM Imidazole after incubation with elution buffer for 5 minutes at 4° C. (end over end rotation) by centrifuging at 800*g for 5 minutes at 4° C. The elution was performed 2 more times (a total of 3 times). The samples were analyzed (both supernatant and pellet along with whole cell lysate) on SDSPAGE. The samples were dialyzed in 50 mM Tris, pH 8.0, 100 mM NaCl with at least one buffer exchange (dialyze in at least 100x sample volume) to generate purified collagen lysate.

In Vitro Hydroxylation Reaction with Purified Collage Monomers

1) The reaction mix for 40 reactions (250 ul each reaction) as per the table below was prepared.

| | | Reaction Mix for 40 reactions | | | |
|---|---|---|---|---|---|
| S. No. | Assay component | Stock Concentration | Final Concentration | For 500 ul reaction | 500 * 20 = 10 ml Rxn |
| 1 | Iron Sulfate (FeSO4) | 5 mM | 50 uM | 5 | 100 |
| 2 | DTT | 10 mM | 100 uM | 5 | 100 |
| 3 | Ascorbic Acid | 200 mM | 2 mM | 5 | 100 |
| 4 | Tris-HCl | 1M | 50 mM | 25 | 500 |
| | | | | Total | 800 |

2) Aliquoted 20 ul of the above mix into each tube (each reaction was done in triplicates) for a 250 ul reaction.
3) Add 1 g/L BSA, 0.1 g/L catalase and water to make up the final volume to 250 uL
4) Add 5 µM fusion protein
5) Add 2 µM collagen sample
6) Incubate reaction at 32° C. for 2 min
7) Add 2.5 ul of 0.4 M 2-oxoglutarate and mix well
8) Incubate at 32° C. for 1 hour
9) Transfer 100 ul of each reaction in new tube and hand over samples for hydroxyproline assay Hydroxyproline Assay
  1. The solutions below were prepared:
    A. Citrate/Acetate buffer (for 100 mL)
      5% Citric Acid (5 g) (Sigma Aldrich C1909, monohydrate)
      1.2% Glacial Acetic Acid (1.2 mL) (Fisher Scientific A38-500)
      7.24% Sodium Acetate (7.24 g) (Sigma Aldrich, S2889)
      3.5% Sodium Hydroxide (3.4 g) (Sigma Aldrich, 306576)
      Make up with MILLI-Q ultrapure water to 100 mL
    B. Chloramine T (for 20 mL)
      1.41 g Chloramine T
      10 mL Isopropanol
      10 mL MILLI-Q ultrapure water
    C. Ehrlich's Solution (for 20 mL)
      4 g p-dimethylbenzaldehyde (DMAB)
      6 mL Hydrochloric acid
      14 mL Isopropanol
    D. Chloramine T/Citrate-Acetate Solution (for 20 mL)
      4 mL Chloramine T (from above)
      16 mL Citrate/Acetate buffer (from above)
  2. Sample Preparation:
    a. 100 µL of in-vitro hydroxylation reaction containing collagen was placed into glass amber vials.
    b. 500 µL of concentrated HCl was added and vials were capped tightly.
    c. Vials were incubated at 125° C. in heat block for at least 18 hrs.
    d. Samples were dried using speed vac.
    e. The dry samples were resuspended in vials with 225 uL MILLI-Q ultrapure water.
    f. Centrifuged samples to remove precipitate and debris at 10,000×g for 5 mins and removed supernatant to be used in assay.

3. Standard Curve Preparation:
   a. Prepared a 1000 ug/mL stock solution of hydroxyproline
   b. Used the stock solution to prepare a top standard concentration of 50 ug/mL
   c. Using the 50 ug/mL solution, made the following concentrations for the standard curve: 25, 18.75, 12.5, 6.25, 3.125 ug/mL
   d. 0 ug/mL=water
   e. These standards were placed in wells A1 through A7 with its duplicate in B1 through B7 in a 96-well plate
4. Internal Control:
   a. Followed steps 2a-d, but used 400 μL of Type III Collagen (Abcam, ab7528) in place of in-vitro hydroxylation reaction containing collage
   b. Resuspended in 400 uL MILLI-Q ultrapure water
   c. Internal control was placed in A8 and B8 of a 96-well plate
5. Internal Control quantification:
   a. Took a 50 uL aliquot from the stock vial of Type III Collagen to run on qSDS.
   b. Used the concentration obtained by qSDS to calculate percent hydroxylation of the internal control.
6. Hydroxyproline assay:
   a. Added 50 uL of standards and sampled in quadruplicate (2 replicates will be blanks where no Chloramine T is added)
   b. For each reaction to be analyzed (including standard curve wells), added 100 uL of Chloramine T/Citrate-Acetate solution
   c. For blanks added 100 ul of water/citrate-acetate solution (no oxidation should occur in these samples)
   d. Sealed plate and incubated at 30° C. for 25 minutes with shaking
   e. Added 100 uL of Erhlich's solution and mixed each well thoroughly until wells were clear
   f. Sealed plate and incubated for 25 minutes at 65° C. with shaking
   g. Removed plate(s) from the heat source and measured the absorbance of all samples/blanks at 560 nm.
   h. Calculated percent hydroxylation by obtaining the molecular weight of collagen used. Also needed is the number of hydroxyproline sites and proline in the helical region of said collagen used.
   i. Example Percent (%) hydroxyproline calculation:
      Molecular weight of PP685 collagen=94,752 g/mol
      Molecular weight of hydroxyproline=131.13 g/mol
      # of hydroxyproline sites in helical region=145
      # of proline sites in helical region=246
      PP685 collagen concentration in IVOH reaction=0.084 g/L
      a. Concentration of hydroxyproline obtained from standard curve for IVOH reaction
         3.91 ug/mL
         Corrected using multiplication factor=3.1×3.91 ug/mL=12.1 ug/mL
      b. Concentration of hydroxyproline in terms of micrograms (ug)
         50 uL of sample used per well
         (50 uL×12.1 ug/mL) divide by 1000=0.607 ug hydroxyproline
      c. Microgram of collagen used in IVOH reaction
         50 uL of sample used per well
         (50 uL×0.084 g/L) multiplied by $1\times10^6$=4.2 ug
      d. nmol of PP685 collagen
         (4.2 ug/$1\times10^6$ ug)×1 g=$4.2\times10^{-6}$ g
         ($4.2\times10^{-6}$ g)/(94752.76 g/mol of PP685 collagen)= $4.4\times10^{-11}$ mol
         $4.4\times10^{-11}$ mol×($1\times10^9$ nmol/1 mol)=0.044 nmol
      e. nmol of hydroxyproline
         (0.607 ug/131.13 g/mol)×1000=4.6 nmol hydroxyproline
      f. nmol proline
         0.044 nmol collagen×246=10.8 nmol proline
      g. Percent % hydroxyproline
         (4.6 nmol/10.8 nmol)×100=42% hydroxylation Results

| Unhydroxylated Collagen Strain | Hydroxylating Enzyme | % Hydroxyproline |
|---|---|---|
| PP434 | PP547 (Fusion protein) | 34.8% |
| PP434 | PP635 (Fusion protein) | 26.6% |
| PP434 | PP636 (bidirectional P4HA/B) | 0.9% |

The results indicated that in the presence of necessary cofactors and appropriate reaction conditions (temperature and pH), the fusion protein in both strains (PP547 and PP635) were able to hydroxylate collagen substrate to a higher % than PP636 strain which contains the non-fusion proteins. PP547 and PP635 differed by the presence of a small fragment of collagen in the former which was initially thought to be required for strain as well as protein stability. This indicated that the fusion protein is stable and can function as a better dioxygenase in vitro compared to the non-fusion proteins thereby providing an advantage over the non-fusion counterpart. The fusion of both P4HA and P4HB resulted in stoichiometric amounts of the protein leading to a functional tetramer which helps in protein structure and stability. % hydroxylation results were confirmed by mass spectrometry.

Example 8

In-vitro hydroxylation in lysate was performed on cells lysed at pH 12 using $NaPO_4$ buffer followed by mixing with 0.1 mM $FeSO_4$, 2 mM ascorbic acid, 25 mM DTT and 25 mM α-ketoglutaric acid. The mixture was adjusted to pH 7.5 and incubated for 3 hours at 32° C. by shaking in an incubator for the reaction to proceed. Following completion of the reaction, the pH was dropped to 4 and the reaction was mixed overnight 18 hours) at 25° C. and centrifuged at ~7,000×g to harvest the supernatant. The supernatant was dialyzed against water or buffer and used in the hydroxyproline assay.

Example 9

For in-vivo hydroxylation, collagen was synthesized in the rough endoplasmic reticulum with the help of several chaperones and enzymes. The folding mechanism of collagen was aided by protein disulfide isomerase (PDI) which is part of P4HA-B fusion protein present in the strains used here. PDI helps in correct disulfide bond formation in the noncollagenous N and C-terminal of the protein which is followed by hydroxylation of proline residues by P4HA part of the fusion protein. The cofactors involved in the formation of hydroxylation reaction were present in the ER (endoplasmic reticulum) making it an important organelle for in vivo hydroxylation. Once collagen is synthesized it is stabilized by chaperones present in the ER and hydroxylated by the P4HA-B fusion protein where the B subunit further stabilizes and or helps in trimerization whereas the A subunit hydroxylates the proline residues using its dioxygenase activity.

Numerous modifications and variations on the present disclosure are possible in light of the above teachings. It is, therefore, to be understood that within the scope of the accompanying claims, the disclosure may be practiced otherwise than as specifically described herein.

We claim:

1. A fusion protein comprising:
   a prolyl 4-hydroxylase alpha subunit; and
   a prolyl 4-hydroxylase beta subunit,
   wherein the prolyl 4-hydroxylase alpha subunit is at the N-terminus of the fusion protein and the prolyl 4-hydroxylase beta subunit is at the C-terminus of the fusion protein, wherein the prolyl 4-hydroxylase alpha subunit is encoded by a polynucleotide comprising SEQ ID NO: 1.

2. A fusion protein comprising:
   a prolyl 4-hydroxylase alpha subunit; and
   a prolyl 4-hydroxylase beta subunit,
   wherein the prolyl 4-hydroxylase alpha subunit is at the N-terminus of the fusion protein and the prolyl 4-hydroxylase beta subunit is at the C-terminus of the fusion protein, wherein the prolyl 4-hydroxylase beta subunit is encoded by a polynucleotide comprising SEQ ID NO: 2.

3. A fusion protein comprising:
   a prolyl 4-hydroxylase alpha subunit; and
   a prolyl 4-hydroxylase beta subunit,
   wherein the prolyl 4-hydroxylase alpha subunit is at the N-terminus of the fusion protein and the prolyl 4-hydroxylase beta subunit is at the C-terminus of the fusion protein, wherein the prolyl 4-hydroxylase alpha subunit is encoded by a polynucleotide comprising SEQ ID NO: 1 and the prolyl 4-hydroxylase beta subunit is encoded by a polynucleotide comprising SEQ ID NO: 2.

* * * * *

SEQUENCE LISTING

<160> NUMBER OF SEQ ID NOS: 21

<210> SEQ ID NO 1
<211> LENGTH: 1612
<212> TYPE: DNA
<213> ORGANISM: Artificial Sequence
<220> FEATURE:
<223> OTHER INFORMATION: Synthetic nucleotide

<400> SEQUENCE: 1

```
atgatttggt atatcctagt cgttggtatt ttgttgccac agtcactggc tcacccaggc      60
ttcttcactt ctataggaca gatgactgat ttgattcaca cagaaaaaga cctagttaca     120
agccttaaag actatatcaa agctgaagag gataagttgg agcaaatcaa aaagtgggca     180
gagaaactcg atagattgac tagtactgca acaaaagatc ctgagggttt tgtgggtcac     240
ccagtgaatg ctttcaagct gatgaagaga cttaatacag agtggtcaga attggaaaac     300
ttggtactta agatatgag tgatggattc atttctaact taacaattca aagacaaatac     360
tttccaaacg atgaggacca agtaggagca gcaaaagctt tgttgcgatt gcaggacaca     420
tacaatttgg acaccgacac gatatcgaag ggtgatttac ctggtgtgaa gcataagtcc     480
ttcctcactg tggaagattg ttttgaattg ggaaaagtcg catatacaga agccgactac     540
tatcacacag aattatggat ggagcaagct ctgcgtcagt tggacgaagg tgaagtttct     600
accgttgata aggtttcagt tttggattac ttatcatacg ctgtttacca gcaaggtgat     660
ctggacaaag ctctactttt aactaaaaag ttgttggagc tggacccgga gcatcaaaga     720
gctaacggta atctgaaata ctttgaatac atcatggcta aggaaaagga cgcaaataag     780
tcctcgtccg atgaccaatc cgatcaaaag accactctga aaaaaaaagg tgcagctgtt     840
gactacctcc cagagagaca aaagtatgaa atgctgtgta gaggagaggg tatcaagatg     900
actccaagga gacagaaaaa gctgttctgt agatatcatg atgggaaccg taacccaaaa     960
ttcattcttg ctccagcgaa acaggaagat gaatgggaca gcctagaat cattcgtttt    1020
catgacatca tctccgatgc agaaatagag gttgtgaaag acttggccaa accaagattg    1080
agtagggcta ccgtccatga ccctgagact ggaaaattga ctaccgcaca atatcgtgtc    1140
tctaaatcag catggttgtc cggttacgag aatcccgtgg tcagccgtat caatatgcgt    1200
attcaagatt tgactggtct tgacgtaagc actgctgagg aactacaagt tgccaactat    1260
ggtgtgggcg gtcagtatga accccacttt gatttcgcca gaaaggacga gcctgatgct    1320
tttaaggagc taggtactgg aaatagaatc gcaacgtggt tgttctatat gtccgatgtg    1380
cttgctggag gagccacagt tttccctgag gtaggtgctt ctgtttggcc taaaaagggc    1440
acggccgtat tttggtacaa tctgtttgca tctggagaag gtgattacag cactagacat    1500
gctgcttgtc ccgtcttagt cggtaataag tgggtttcca ataagtggct gcatgagaga    1560
ggtcaagagt ttaggaggcc atgcacattg tcagaattag aatgataatt tt            1612
```

<210> SEQ ID NO 2
<211> LENGTH: 1750
<212> TYPE: DNA
<213> ORGANISM: Artificial Sequence
<220> FEATURE:
<223> OTHER INFORMATION: Synthetic nucleotide

<400> SEQUENCE: 2

```
aaaatgagat cccatctat tttcaccgct gtcttgttcg ctgcctcctc tgcattggct       60
gcccctgtta acactaccac tgaagacgag actgctcaaa ttccagctga agcagttatc     120
```

```
ggttactctg accttgaggg tgatttcgac gtcgctgttt tgcctttctc taactccact    180
aacaacggtt tgttgttcat taacaccact atcgcttcca ttgctgctaa ggaagagggt    240
gtctctctcg agaaaagaga ggccgaagct gcacccgatg aggaagatca tgttttagta    300
ttgcataaag gaaatttcga tgaagctttg gccgctcaca atatctgct cgtcgagttt    360 tacgctccct ggtgcggtca ttgtaaggcc cttgcaccag agtacgccaa ggcagctggt    420
aagttaaagg ccgaaggttc agagatcaga ttagcaaaag ttgatgctac agaagagtcc    480
gatcttgctc aacaatacgg ggttcgagga tacccaacaa ttaagttttt caaaaatggt    540
gatactgctt ccccaaagga atatactgct ggtagagagg cagacgacat agtcaactgg    600
ctcaaaaaga gaacgggccc agctgcgtct acattaagcg acggagcagc agccgaagct    660
cttgtggaat ctagtgaagt tgctgtaatc ggtttcttta aggacatgga atctgattca    720
gctaaacagt tccttttagc agctgaagca atcgatgaca tccctttcgg aatcacctca    780
aatagtgacg tgttcagcaa gtaccaactt gacaaagatg gagtggtctt gttcaaaaag    840
tttgacgaag gcagaaacaa tttcgagggt gaggttacaa aggagaaact gcttgatttc    900
attaaacata accaactacc cttagttatc gaattcactg aacaaactgc tcctaagatt    960
ttcggtggag aaatcaaaac acatatcttg ttgttttttgc caaagtccgt atcggattat   1020
gaaggtaaac tctccaattt caaaaaggcc gctgagagct ttaagggcaa gattttgttc   1080
atctttattg actcagacca cacagacaat cagaggattt tggagttttt cggtttgaaa   1140
aaggaggaat gtccagcagt ccgtttgatc accttggagg aggagatgac caaatacaaa   1200
ccagagtcgg atgagttgac tgccgagaag ataacagaat tttgtcacag atttctggaa   1260
ggtaagatca agcctcatct tatgtctcaa gagttgcctg atgactggga taagcaacca   1320
gttaaagtat tggtgggtaa aaactttgag gaagtggcct cgacgagaa aaaaaatgtc   1380 tttgttgaat tctatgctcc gtggtgtggt cactgtaagc agctggcacc aatttgggat   1440
aaactgggtg aaacttacaa agatcacgaa acattgtta ttgcaaagat ggacagtact   1500
gctaacgaag tggaggctgt gaaagttcac tccttcccta cgctgaagtt ctttcctgca   1560
tctgctgaca gaactgttat cgactataat ggagagagga cattggatgg ttttaaaaag   1620
tttcttgaat ccggaggtca agacggagct ggtgacgacg atgatttgga agatctggag   1680
gaggctgagg aacctgatct tgaggaggat gacgaccaga aggcagtcaa agatgaactg   1740
tgataagggg                                                         1750
```

<210> SEQ ID NO 3
<211> LENGTH: 58
<212> TYPE: DNA
<213> ORGANISM: Artificial Sequence
<220> FEATURE:
<223> OTHER INFORMATION: Synthetic nucleotide

<400> SEQUENCE: 3

```
ctcaattgtt gtttatatca ttgctattta aatcaggtga acccacctaa ctattttt    58
```

<210> SEQ ID NO 4
<211> LENGTH: 30
<212> TYPE: DNA
<213> ORGANISM: Artificial Sequence
<220> FEATURE:
<223> OTHER INFORMATION: Synthetic nucleotide

<400> SEQUENCE: 4

```
ttttgttgtt gagtgaagcg agtgacggaa                                    30
```

<210> SEQ ID NO 5
<211> LENGTH: 60
<212> TYPE: DNA
<213> ORGANISM: Artificial Sequence
<220> FEATURE:
<223> OTHER INFORMATION: Synthetic nucleotide

<400> SEQUENCE: 5

```
ttccgtcact cgcttcactc aacaacaaaa atgatttggt atatcctagt cgttggtatt    60
```

<210> SEQ ID NO 6
<211> LENGTH: 30
<212> TYPE: DNA
<213> ORGANISM: Artificial Sequence
<220> FEATURE:
<223> OTHER INFORMATION: Synthetic nucleotide

<400> SEQUENCE: 6

```
ttctaattct gacaatgtgc atggcctcct                                    30
```

<210> SEQ ID NO 7
<211> LENGTH: 84
<212> TYPE: DNA
<213> ORGANISM: Artificial Sequence
<220> FEATURE:
<223> OTHER INFORMATION: Synthetic nucleotide

<400> SEQUENCE: 7

```
aggaggccat gcacattgtc agaattagaa ggttctggct ctggttctgg ctctatgaga    60
ttcccatcta ttttcaccgc tgtc                                          84
```

<210> SEQ ID NO 8
<211> LENGTH: 69
<212> TYPE: DNA
<213> ORGANISM: Artificial Sequence
<220> FEATURE:
<223> OTHER INFORMATION: Synthetic nucleotide

<400> SEQUENCE: 8

```
ctgcaacaaa agaaacaaga cattactgaa gggccggccg cacaaacgaa ggtctcactt    60
aatcttctg                                                           69
```

<210> SEQ ID NO 9
<211> LENGTH: 10109
<212> TYPE: DNA
<213> ORGANISM: Artificial Sequence
<220> FEATURE:
<223> OTHER INFORMATION: Synthetic nucleotide

<400> SEQUENCE: 9

```
ggatccttca gtaatgtctt gtttcttttg ttgcagtggt gagccatttt gacttcgtga    60
aagtttcttt agaatagttg tttccagagg ccaaacattc cacccgtagt aaagtgcaag   120
cgtaggaaga ccaagactgg cataaatcag gtataagtgt cgagcactgg caggtgatct   180
tctgaaagtt tctactagca gataagatcc agtagtcatg catatggcaa caatgtaccg   240
tgtggatcta agaacgcgtc ctactaacct tcgcattcgt tggtccagtt tgttgttatc   300
gatcaacgtg acaaggttgt cgattccgcg taagcatgca tacccaagga cgcctgttgc   360
aattccaagt gagccagttc caacaatctt tgtaatatta gagcacttca ttgtgttgcg   420
cttgaaagta aaatgcgaac aaattaagag ataatctcga aaccgcgact tcaaacgcca   480
```

```
atatgatgtg cggcacacaa taagcgttca tatccgctgg gtgactttct cgctttaaaa    540
aattatccga aaaatttttc ctctagaatg ggtaaggaaa agactcacgt ttcgaggccg    600
cgattaaatt ccaacatgga tgctgattta tatgggtata atgggctcg cgataatgtc    660 gggcaatcag gtgcgacaat ctatcgattg tatgggaagc ccgatgcgcc agagttgttt    720
ctgaaacatg gcaaaggtag cgttgccaat gatgttacag atgagatggt cagactaaac    780
tggctgacgg aatttatgcc tcttccgacc atcaagcatt ttatccgtac tcctgatgat    840
gcatggttac tcaccactgc gatccccggc aaaacagcat tccaggtatt agaagaatat    900
cctgattcag gtgaaaatat tgttgatgcg ctggcagtgt tcctgcgccg gttgcattcg    960
attcctgttt gtaattgtcc ttttaacagc gatcgcgtat ttcgtctcgc tcaggcgcaa   1020
tcacgaatga ataacggttt ggttgatgcg agtgattttg atgacgagcg taatggctgg   1080
cctgttgaac aagtctggaa agaaatgcat aagcttttgc cattctcacc ggattcagtc   1140
gtcactcatg tgatttctc acttgataac cttattttg acgagggaa attaataggt     1200 tgtattgatg ttggacgagt cggaatcgca gaccgatacc aggatcttgc catcctatgg   1260
aactgcctcg gtgagttttc tccttcatta cagaaacggc ttttttcaaaa atatggtatt  1320 gataatcctg atatgaataa attgcagttt catttgatgc tcgatgagtt tttctaaaat   1380 tgacaccta cgattattta gagagtattt attagttta ttgtatgtat acggatgttt     1440
tattatctat ttatgccctt atattctgta actatccaaa agtcctatct tatcaagcca   1500
gcaatctatg tccgcgaacg tcaactaaaa ataagctttt tatgctgttc tctctttttt   1560
tcccttcggt ataattatac cttgcatcca cagattctcc tgccaaattt tgcataatcc   1620
tttacaacat ggctatatgg gagcacttag cgccctccaa aacccatatt gcctacgcat   1680
gtataggtgt ttttttccaca atattttctc tgtgctctct ttttattaaa gagaagctct   1740
atatcggaga agcttctgtg gccgttatat tcggccttat cgtgggacca cattgcctga   1800
attggtttgc cccggaagat tggggaaact tggatctgat taccttagct gcatcagaat   1860
tggttaattg gttgtaacac tgaccccctat ttgtttattt ttctaaatac attcaaatat   1920
gtatccgctc atgagacaat aaccctgata aatgcttcaa taatattgaa aaaggaagaa   1980
tatgagtatt caacatttcc gtgtcgccct tattccctttt tttgcggcat tttgccttcc   2040
tgtttttgct cacccagaaa cgctggtgaa agtaaaagat gctgaagatc agttgggtgc   2100
acgagtgggt tacatcgaac tggatctcaa cagcggtaag atccttgaga gttttcgccc   2160
cgaagaacgt tttccaatga tgagcacttt taaagttctg ctatgtggcg cggtattatc   2220
ccgtattgac gccgggcaag agcaactcgg tcgccgcata cactattctc agaatgactt   2280
ggttgagtac tcaccagtca cagaaaagca tcttacggat ggcatgacag taagagaatt   2340
atgcagtgct gccataacca tgagtgataa cactgcggcc aacttacttc tgacaacgat   2400
cggaggaccg aaggagctaa ccgcttttttt gcacaacatg ggggatcatg taactcgcct   2460
tgatcgttgg gaaccggagc tgaatgaagc cataccaaac gacgagcgtg acaccacgat   2520
gcctgtagcg atggcaacaa cgttgcgcaa actattaact ggcgaactac ttactctagc   2580
ttcccggcaa caattaatag actggatgga ggcggataaa gttgcaggac cacttctgcg   2640
ctcggccctt ccggctggct ggtttattgc tgataaatcc ggagccggtg agcgtggttc   2700
tcgcggtatc atcgcagcgc tggggccaga tggtaagccc tcccgtatcg tagttatcta   2760
cacgacgggg agtcaggcaa ctatggatga acgaaataga cagatcgctg agataggtgc   2820
```

```
ctcactgatt aagcattggt aactgcagga aaagggtacc actgagcgtc agaccccgta   2880
gaaaagatca aaggatcttc ttgagatcct ttttttctgc gcgtaatctg ctgcttgcaa   2940
acaaaaaaac caccgctacc agcggtggtt tgtttgccgg atcaagagct accaactctt   3000
tttccgaagg taactggctt cagcagagcg cagataccaa atactgttct tctagtgtag   3060
ccgtagttag gccaccactt caagaactct gtagcaccgc ctacatacct cgctctgcta   3120
atcctgttac cagtggctgc tgccagtggc gataagtcgt gtcttaccgg gttggaccca   3180
agacgatagt taccggataa ggcgcagcgg tcgggctgaa cggggggttc gtgcacacag   3240
cccagcttgg agcgaacgac ctacaccgaa ctgagatacc tacagcgtga gctatgagaa   3300
agcgccacgc ttcccgaagg gagaaaggcg gacaggtatc cggtaagcgg cagggtcgga   3360
acaggagagc gcacgaggga gcttccaggg ggaaacgcct ggtatcttta tagtcctgtc   3420
gggtttcgcc acctctgact tgagcgtcga ttttttgtga tgctcgtcag ggggcggagc   3480
ctatggaaaa acgccagcaa cgcggccttt ttacggttcc tggccttttg ctggccttt    3540 gctcacatgt tttgttcgat tattctccag ataaaatcaa caatagttgt ttgtaagtaa   3600
acgaatcaag atactgaaaa tagttttcaaa agcagatcat ctgggattta tatcaggc    3660 atcctgcttt agttcttttt tgaacccaaa ggctatctga tgaaaagttg atataggtat   3720
gaagaccaga atttgcctag aggctaaccg agacctgagg ctaaaaaagg caggaggaaa   3780
agtcctgcca aagataggta tttgaacttg ttcgaaaaag gcggaagttt aaacacatgg   3840
ttggagcaag cggcggaata gcggagggat gatacgcagc aaggctggga tcattcgagt   3900
ttcaaggaac gttagctcaa cattcattga ctggtaagcg acaactggtt tcatctgggt   3960
ggagttagtc tggtgttggg atgctagttg ttccccacaa ttgaaggcca gatgaggagg   4020
atggtgtggt gataagagat gcaaacagat ggttatggcc ttttgagaac aaagtagacc   4080
tgtcactcaa ttgttgttta tatcattgct atttaaataa tgtatctaaa cgcaaactcc   4140
gagctggaaa aatgttaccg gcgatgcgcg gacaatttag aggcggcgat caagaaacac   4200
ctgctgggcg agcagtctgg agcacagtct tcgatgggcc cgagatccca ccgcgttcct   4260
gggtaccggg acgtgaggca gcgcgacatc catcaaatat accaggcgcc aaccgagtgt   4320
ctcggaaaac agcttctgga tatcttccgc tggcggcgca acgacgaata atagtccctg   4380
gaggtgacgg aatatatatg tgtggagggt aaatctgaca gggtgtagca aaggtaatat   4440
tttcctaaaa catgcaatcg gctgccccgc aacgggaaaa agaatgactt tggcactctt   4500
caccagagtg gggtgtcccg ctcgtgtgtg caaataggct cccactggtc accccggatt   4560
ttgcagaaaa acagcaagtt ccggggtgtc tcactggtgt ccgccaataa gaggagccgg   4620
caggcacgga gtttacatca agctgtctcc gatacactcg actaccatcc gggtctctca   4680 gagagggaa tggcactata aataccgcct ccttgcgctc tctgccttca tcaatcaaat   4740
catgctgagg actcgaattc gacctctgtt gcctctttgt tggacgaacc attcaccggt   4800
gtcttgtact taaagggcag tggtatcact gaagacttcc agtccctaaa gggtaagaag   4860
atcggttacg ttggtgactt cggtaagatc caaatcgatg aattgaccaa gcactacggt   4920
atgaagccag aagactacac cgccgtcaga tgtggtatga atgtcgccaa gtacatcatc   4980
gaaggtaaga ttgatgccgg tattggtatc gaatgtatgc aacaagtcga attggaagag   5040
tacttggcca agcaaggcag accagcttct gatgctaaaa tgttgagaat tgacaagttg   5100
gcttgcttgg gttgctgttg cttctgtacc gttcttttaca tctgcaacga tgaatttttg   5160
aagaagaacc ctgaaaaggt cagaaagttc ttgaaagcca tcaagaaggc aaccgactac   5220
```

```
gttctagccg accctgtgaa ggcttggaaa gaatacatcg acttcaagcc tcaattgaac    5280
aacgatctat cctacaagca ataccaaaga tgttacgctt acttctcttc atctttgtac    5340
aatgttcacc gtgactggaa gaaggttacc ggttacggta agagattagc catcttgcca    5400
ccagactatg tctcgaacta cactaatgaa tacttgtcct ggccagaacc agaagaggtt    5460
tctgatcctt tggaagctca aagattgatg gctattcatc aagaaaaatg cagacaggaa    5520
ggtactttca agagattggc tcttccagct taagcggccg cgagtcgtga gtaatcaaga    5580
ggatgtcaga atgccatttg cctgagagat gcaggcttca ttttgatac tttttatt     5640 gtaacctata tagtatagga ttttttttgt cattttgttt cttctcgtac gagcttgctc    5700
ctgatcagcc tatctcgcag ctgatgaata tcttgtggta ggggtttggg aaaatcattc    5760
gagtttgatg ttttcttgg tatttcccac tcctcttcag agtacagaag attaagtgag    5820
acgttcgttt gtgctccgga caggtgaacc cacctaacta tttttaactg ggatccagtg    5880
agctcgctgg gtgaaagcca accatctttt gtttcgggga accgtgctcg ccccgtaaag    5940 ttaattttt tttcccgcgc agctttaatc tttcggcaga gaaggcgttt tcatcgtagc    6000
gtgggaacag aataatcagt tcatgtgcta tacaggcaca tggcagcagt cactattttg    6060 cttttaacc ttaaagtcgt tcatcaatca ttaactgacc aatcagattt tttgcatttg    6120
ccacttatct aaaaatactt ttgtatctcg cagatacgtt cagtggtttc caggacaaca    6180
cccaaaaaaa ggtatcaatg ccactaggca gtcggtttta tttttggtca cccacgcaaa    6240
gaagcaccca cctctttag gttttaagtt gtgggaacag taacaccgcc tagagcttca    6300
ggaaaaacca gtacctgtga ccgcaattca ccatgatgca gaatgttaat ttaaacgagt    6360
gccaaatcaa gatttcaaca gacaaatcaa tcgatcccata gttacccatt ccagcctttt    6420
cgtcgtcgag cctgcttcat tcctgcctca ggtgcataac tttgcatgaa aagtccagat    6480
tagggcagat tttgagttta aaataggaaa tataaacaaa tataccgcga aaaaggtttg    6540
tttatagctt ttcgcctggt gccgtacggt ataaatacat actctcctcc ccccctggt    6600 tctctttttc ttttgttact tacattttac cgttccgtca ctcgcttcac tcaacaacaa    6660
aaatgatttg gtatatccta gtcgttggta tttttgttgcc acagtcactg gctcacccag    6720
gcttcttcac ttctatagga cagatgactg atttgattca cacagaaaaa gacctagtta    6780
caagccttaa agactatatc aaagctgaag aggataagtt ggagcaaatc aaaaagtggg    6840
cagagaaact cgatagattg actagtactg caacaaaaga tcctgagggt tttgtgggtc    6900
acccagtgaa tgctttcaag ctgatgaaga gacttaatac agagtggtca gaattggaaa    6960
acttggtact taaagatatg agtgatggat tcatttctaa cttaacaatt caaagacaat    7020
actttccaaa cgatgaggac caagtaggag cagcaaaagc tttgttgcga ttgcaggaca    7080
catacaattt ggacaccgac acgatatcga agggtgattt acctggtgtg aagcataagt    7140
ccttcctcac tgtggaagat tgttttgaat tgggaaaagt cgcatataca gaagccgact    7200
actatcacac agaattatgg atggagcaag ctctgcgtca gttggacgaa ggtgaagttt    7260
ctaccgttga taaggtttca gttttggatt acttatcata cgctgtttac cagcaaggtg    7320
atctggacaa agctctactt ttaactaaaa agttgttgga gctggacccg gagcatcaaa    7380
gagctaacgg taatctgaaa tactttgaat acatcatggc taaggaaaag gacgcaaata    7440
agtcctcgtc cgatgaccaa tccgatcaaa agaccactct gaaaaaaaaa ggtgcagctg    7500
ttgactacct cccagagaga caaaagtatg aaatgctgtg tagaggagag ggtatcaaga    7560
```

```
tgactccaag gagacagaaa aagctgttct gtagatatca tgatgggaac cgtaacccaa    7620
aattcattct tgctccagcg aaacaggaag atgaatggga caagcctaga atcattcgtt    7680
ttcatgacat catctccgat gcagaaatag aggttgtgaa agacttggcc aaaccaagat    7740
tgagtagggc taccgtccat gaccctgaga ctggaaaatt gactaccgca caatatcgtg    7800
tctctaaatc agcatggttg tccggttacg agaatcccgt ggtcagccgt atcaatatgc    7860
gtattcaaga tttgactggt cttgacgtaa gcactgctga ggaactacaa gttgccaact    7920
atggtgtggg cggtcagtat gaaccccact ttgatttcgc cagaaaggac gagcctgatg    7980
cttttaagga gctaggtact ggaaatagaa tcgcaacgtg gttgttctat atgtccgatg    8040
tgcttgctgg aggagccaca gttttccctg aggtaggtgc ttctgtttgg cctaaaaagg    8100
gcacggccgt attttggtac aatctgtttg catctggaga aggtgattac agcactagac    8160
atgctgcttg tcccgtctta gtcggtaata agtgggtttc caataagtgg ctgcatgaga    8220
gaggtcaaga gtttaggagg ccatgcacat tgtcagaatt agaaggttct ggctctggtt    8280
ctggctctat gagattccca tctatttttca ccgctgtctt gttcgctgcc tcctctgcat    8340
tggctgcacc cgatgaggaa gatcatgttt tagtattgca taaggaaat ttcgatgaag    8400 cttttggccgc tcacaaatat ctgctcgtcg agttttacgc tccctggtgc ggtcattgta    8460
aggcccttgc accagagtac gccaaggcag ctggtaagtt aaaggccgaa ggttcagaga    8520
tcagattagc aaaagttgat gctacagaag agtccgatct tgctcaacaa tacggggttc    8580
gaggataccc aacaattaag ttttttcaaaa atggtgatac tgcttcccca aaggaatata    8640
ctgctggtag agaggcagac gacatagtca actggctcaa aaagagaacg ggcccagctg    8700
cgtctacatt aagcgacgga gcagcagccg aagctcttgt ggaatctagt gaagttgctg    8760
taatcggttt ctttaaggac atggaatctg attcagctaa acagttcctt ttagcagctg    8820
aagcaatcga tgacatccct ttcggaatca cctcaaatag tgacgtgttc agcaagtacc    8880
aacttgacaa agatggagtg gtcttgttca aaaagtttga cgaaggcaga aacaatttcg    8940
agggtgaggt tacaaaggag aaactgcttg atttcattaa acataaccaa ctacccttag    9000
ttatcgaatt cactgaacaa actgctccta gatttttcgg tggagaaatc aaaacacata    9060
tcttgttgtt tttgccaaag tccgtatcgg attatgaagg taaactctcc aatttcaaaa    9120
aggccgctga gagctttaag ggcaagattt tgttcatctt tattgactca gaccacacag    9180
acaatcagag gattttggag ttttttcggtt tgaaaaagga ggaatgtcca gcagtccgtt    9240
tgatcacctt ggaggaggag atgaccaaat acaaaccaga gtcggatgag ttgactgccg    9300
agaagataac agaattttgt cacagatttc tggaaggtaa gatcaagcct catcttatgt    9360
ctcaagagtt gcctgatgac tgggataagc aaccagttaa agtattggtg ggtaaaaact    9420
ttgaggaagt ggccttcgac gagaaaaaaa atgtctttgt tgaattctat gctccgtggt    9480
gtggtcactg taagcagctg gcaccaattt gggataaact gggtgaaact tacaaagatc    9540
acgaaaacat tgttattgca aagatggaca gtactgctaa cgaagtggag gctgtgaaag    9600
ttcactcctt ccctacgctg aagttctttc ctgcatctgc tgacagaact gttatcgact    9660
ataatggaga gaggacattg gatggtttta aaaagtttct tgaatccgga ggtcaagacg    9720
gagctggtga cgacgatgat ttggaagatc tggaggaggc tgaggaacct gatcttgagg    9780
aggatgacga ccagaaggca gtcaaagatg aactgtgata aggggtcaag aggatgtcag    9840
aatgccattt gcctgagaga tgcaggcttc attttttgata ctttttttatt tgtaacctat    9900 atagtatagg atttttttttg tcattttgtt tcttctcgta cgagcttgct cctgatcagc    9960
```

```
ctatctcgca gcagatgaat atcttgtggt aggggtttgg gaaaatcatt cgagtttgat    10020 gttttcttg gtatttccca ctcctcttca gagtacagaa gattaagtga gaccttcgtt    10080
tgtgcggttc tggctctggt tctggctct                                      10109
```

<210> SEQ ID NO 10
<211> LENGTH: 10075
<212> TYPE: DNA
<213> ORGANISM: Artificial Sequence
<220> FEATURE:
<223> OTHER INFORMATION: Synthetic nucleotide

<400> SEQUENCE: 10

```
ggatccttca gtaatgtctt gtttcttttg ttgcagtggt gagccatttt gacttcgtga      60
aagtttcttt agaatagttg tttccagagg ccaaacattc cacccgtagt aaagtgcaag     120
cgtaggaaga ccaagactgg cataaatcag gtataagtgt cgagcactgg caggtgatct     180
tctgaaagtt tctactagca gataagatcc agtagtcatg catatggcaa caatgtaccg     240
tgtggatcta agaacgcgtc ctactaacct tcgcattcgt tggtccagtt tgttgttatc     300
gatcaacgtg acaaggttgt cgattccgcg taagcatgca tacccaagga cgcctgttgc     360
aattccaagt gagccagttc caacaatctt tgtaatatta gagcacttca ttgtgttgcg     420
cttgaaagta aaatgcgaac aaattaagag ataatctcga aaccgcgact tcaaacgcca     480
atatgatgtg cggcacacaa taagcgttca tatccgctgg gtgactttct cgcttttaaaa    540 aattatccga aaaatttttc ctctagaatg ggtaaggaaa agactcacgt ttcgaggccg     600
cgattaaatt ccaacatgga tgctgattta tatgggtata aatgggctcg cgataatgtc     660
gggcaatcag gtgcgacaat ctatcgattg tatgggaagc ccgatgcgcc agagttgttt     720
ctgaaacatg gcaaaggtag cgttgccaat gatgttacag atgagatggt cagactaaac     780
tggctgacgg aatttatgcc tcttccgacc atcaagcatt ttatccgtac tcctgatgat     840
gcatggttac tcaccactgc gatccccggc aaaacagcat tccaggtatt agaagaatat     900
cctgattcag gtgaaaatat tgttgatgcg ctggcagtgt tcctgcgccg gttgcattcg     960
attcctgttt gtaattgtcc ttttaacagc gatcgcgtat ttcgtctcgc tcaggcgcaa    1020
tcacgaatga ataacggttt ggttgatgcg agtgattttg atgacgagcg taatggctgg    1080
cctgttgaac aagtctggaa agaaatgcat aagcttttgc cattctcacc ggattcagtc    1140
gtcactcatg gtgatttctc acttgataac cttatttttg acgaggggaa attaataggt    1200
tgtattgatg ttgacgagt cggaatcgca gaccgatacc aggatcttgc catcctatgg    1260
aactgcctcg gtgagttttc tccttcatta cagaaacggc ttttttcaaaa atatggtatt    1320 gataatcctg atatgaataa attgcagttt catttgatgc tcgatgagtt tttctaaaat    1380
tgacacctta cgattattta gagagtattt attagtttta ttgtatgtat acggatgttt    1440
tattatctat ttatgccctt atattctgta actatccaaa agtcctatct tatcaagcca    1500
gcaatctatg tccgcgaacg tcaactaaaa ataagctttt tatgctgttc tctctttttt    1560
tcccttcggt ataattatac cttgcatcca cagattctcc tgccaaattt tgcataatcc    1620
tttacaacat ggctatatgg gagcacttag cgccctccaa aacccatatt gcctacgcat    1680
gtataggtgt ttttccaca atattttctc tgtgctctct ttttattaaa gagaagctct    1740
atatcggaga agcttctgtg gccgttatat tcggccttat cgtgggacca cattgcctga    1800
attggtttgc cccggaagat tggggaaact tggatctgat taccttagct gcatcagaat    1860
```

-continued

```
tggttaattg gttgtaacac tgaccectat ttgtttatt ttctaaatac attcaaatat    1920
gtatccgctc atgagacaat aaccctgata aatgcttcaa taatattgaa aaaggaagaa    1980
tatgagtatt caacatttcc gtgtcgccct tattccctt tttgcggcat tttgccttcc    2040
tgttttgct cacccagaaa cgctggtgaa agtaaaagat gctgaagatc agttgggtgc    2100
acgagtgggt tacatcgaac tggatctcaa cagcggtaag atccttgaga gttttcgccc    2160
cgaagaacgt tttccaatga tgagcacttt taaagttctg ctatgtggcg cggtattatc    2220
ccgtattgac gccgggcaag agcaactcgg tcgccgcata cactattctc agaatgactt    2280
ggttgagtac tcaccagtca cagaaaagca tcttacggat ggcatgacag taagagaatt    2340
atgcagtgct gccataacca tgagtgataa cactgcggcc aacttacttc tgacaacgat    2400
cggaggaccg aaggagctaa ccgcttttt gcacaacatg ggggatcatg taactcgcct    2460
tgatcgttgg gaaccggagc tgaatgaagc cataccaaac gacgagcgtg acaccacgat    2520
gcctgtagcg atggcaacaa cgttgcgcaa actattaact ggcgaactac ttactctagc    2580
ttcccggcaa caattaatag actggatgga ggcggataaa gttgcaggac cacttctgcg    2640
ctcggccctt ccggctggct ggtttattgc tgataaatcc ggagccggtg agcgtggttc    2700
tcgcggtatc atcgcagcgc tggggccaga tggtaagccc tcccgtatcg tagttatcta    2760
cacgacgggg agtcaggcaa ctatggatga acgaaataga cagatcgctg agataggtgc    2820
ctcactgatt aagcattggt aactgcagga aaagggtacc actgagcgtc agaccccgta    2880
gaaaagatca aggatcttc ttgagatcct tttttctgc gcgtaatctg ctgcttgcaa    2940
acaaaaaaac caccgctacc agcggtggtt tgtttgccgg atcaagagct accaactctt    3000
tttccgaagg taactggctt cagcagagcg cagataccaa atactgttct tctagtgtag    3060
ccgtagttag gccaccactt caagaactct gtagcaccgc ctacatacct cgctctgcta    3120
atcctgttac cagtggctgc tgccagtggc gataagtcgt gtcttaccgg gttggaccca    3180
agacgatagt taccggataa ggcgcagcgg tcgggctgaa cggggggttc gtgcacacag    3240
cccagcttgg agcgaacgac ctacaccgaa ctgagatacc tacagcgtga gctatgagaa    3300
agcgccacgc ttcccgaagg gagaaaggcg gacaggtatc cggtaagcgg cagggtcgga    3360
acaggagagc gcacgaggga gcttccaggg ggaaacgcct ggtatcttta tagtcctgtc    3420
gggtttcgcc acctctgact tgagcgtcga ttttgtgat gctcgtcagg ggggcggagc    3480
ctatggaaaa acgccagcaa cgcggccttt ttacggttcc tggccttttg ctggccttt    3540
gctcacatgt tttgttcgat tattctccag ataaaatcaa caatagttgt ttgtaagtaa    3600
acgaatcaag atactgaaaa tagtttcaaa agcagatcat ctgggattta tatatcaggc    3660
atcctgcttt agttcttttt tgaacccaaa ggctatctga tgaaaagttg atataggtat    3720
gaagaccaga atttgcctag aggctaaccg agacctgagg ctaaaaaagg caggaggaaa    3780
agtcctgcca aagataggta tttgaacttg ttcgaaaaag gcggaagttt aaacacatgg    3840
ttggagcaag cggcggaata gcggagggat gatacgcagc aaggctggga tcattcgagt    3900
ttcaaggaac gttagctcaa cattcattga ctggtaagcg acaactggtt tcatctgggt    3960
ggagttagtc tggtgttggg atgctagttg ttccccacaa ttgaaggcca gatgaggagg    4020
atggtgtggt gataagagat gcaaacagat ggttatggcc ttttgagaac aaagtagacc    4080
tgtcactcaa ttgttgttta tatcattgct atttaaataa tgtatctaaa cgcaaactcc    4140
gagctggaaa aatgttaccg gcgatgcgcg gacaatttag aggcggcgat caagaaacac    4200
ctgctgggcg agcagtctgg agcacagtct tcgatgggcc cgagatccca ccgcgttcct    4260
```

```
gggtaccggg acgtgaggca gcgcgacatc catcaaatat accaggcgcc aaccgagtgt    4320
ctcggaaaac agcttctgga tatcttccgc tggcggcgca acgacgaata atagtccctg    4380
gaggtgacgg aatatatatg tgtggagggt aaatctgaca gggtgtagca aaggtaatat    4440
tttcctaaaa catgcaatcg gctgccccgc aacggggaaa agaatgactt tggcactctt    4500
caccagagtg gggtgtcccg ctcgtgtgtg caaataggct cccactggtc accccggatt    4560
ttgcagaaaa acagcaagtt ccggggtgtc tcactggtgt ccgccaataa gaggagccgg    4620
caggcacgga gtttacatca agctgtctcc gatacactcg actaccatcc gggtctctca    4680
gagaggggaa tggcactata aataccgcct ccttgcgctc tctgccttca tcaatcaaat    4740
catgctgagg actcgaattc gacctctgtt gcctcttgt tggacgaacc attcaccggt     4800
gtcttgtact taaagggcag tggtatcact gaagacttcc agtccctaaa gggtaagaag    4860
atcggttacg ttggtgactt cggtaagatc caaatcgatg aattgaccaa gcactacggt    4920
atgaagccag aagactacac cgccgtcaga tgtggtatga atgtcgccaa gtacatcatc    4980
gaaggtaaga ttgatgccgg tattggtatc gaatgtatgc aacaagtcga attggaagag    5040
tacttggcca agcaaggcag accagcttct gatgctaaaa tgttgagaat tgacaagttg    5100
gcttgcttgg gttgctgttg cttctgtacc gttctttaca tctgcaacga tgaattttg    5160 aagaagaacc ctgaaaaggt cagaaagttc ttgaaagcca tcaagaaggc aaccgactac    5220
gttctagccg accctgtgaa ggcttggaaa gaatacatcg acttcaagcc tcaattgaac    5280
aacgatctat cctacaagca ataccaaaga tgttacgctt acttctcttc atctttgtac    5340
aatgttcacc gtgactggaa gaaggttacc ggttacggta agagattagc catcttgcca    5400
ccagactatg tctcgaacta cactaatgaa tacttgtcct ggccagaacc agaagaggtt    5460
tctgatcctt tggaagctca aagattgatg gctattcatc aagaaaaatg cagacaggaa    5520
ggtactttca agagattggc tcttccagct taagcggccg cgagtcgtga gtaatcaaga    5580
ggatgtcaga atgccatttg cctgagagat gcaggcttca ttttttgatac tttttttattt    5640 gtaacctata tagtatagga tttttttttgt cattttgttt cttctcgtac gagccttgctc    5700 ctgatcagcc tatctcgcag ctgatgaata tcttgtggta ggggtttggg aaaatcattc    5760
gagtttgatg ttttttcttgg tatttcccac tcctcttcag agtacagaag attaagtgag    5820
acgttcgttt gtgctccgga caggtgaacc cacctaacta ttttttaactg ggatccagtg    5880 agctcgctgg gtgaaagcca accatctttt gtttcgggga accgtgctcg ccccgtaaag    5940 ttaattttt tttcccgcgc agctttaatc tttcggcaga gaaggcgttt tcatcgtagc    6000
gtgggaacag aataatcagt tcatgtgcta tacaggcaca tggcagcagt cactatttg    6060 cttttttaacc ttaaagtcgt tcatcaatca ttaactgacc aatcagattt tttgcatttg    6120
ccacttatct aaaaatactt ttgtatctcg cagatacgtt cagtggtttc caggacaaca    6180
cccaaaaaaa ggtatcaatg ccactaggca gtcggtttta ttttttggtca cccacgcaaa    6240 gaagcaccca cctcttttag gttttaagtt gtgggaacag taacaccgcc tagagcttca    6300
ggaaaaacca gtacctgtga ccgcaattca ccatgatgca gaatgttaat ttaaacgagt    6360
gccaaatcaa gatttcaaca gacaaatcaa tcgatcccata gttacccatt ccagccttt    6420 cgtcgtcgag cctgcttcat tcctgcctca ggtgcataac tttgcatgaa aagtccagat    6480
tagggcagat tttgagttta aaataggaaa tataaacaaa tataccgcga aaaggtttg    6540 tttatagctt ttcgcctggt gccgtacggt ataaatacat actctcctcc cccccctggt    6600
```

```
tctctttttc ttttgttact tacattttac cgttccgtca ctcgcttcac tcaacaacaa    6660
aaatgagatt cccatctatt ttcaccgctg tcttgttcgc tgcctcctct gcattggctg    6720
cacccgatga ggaagatcat gttttagtat tgcataaagg aaatttcgat gaagctttgg    6780
ccgctcacaa atatctgctc gtcgagtttt acgctccctg gtgcggtcat tgtaaggccc    6840
ttgcaccaga gtacgccaag gcagctggta agttaaaggc cgaaggttca gagatcagat    6900
tagcaaaagt tgatgctaca gaagagtccg atcttgctca acaatacggg gttcgaggat    6960
acccaacaat taagtttttc aaaaatggtg atactgcttc cccaaaggaa tatactgctg    7020
gtagagaggc agacgacata gtcaactggc tcaaaaagag aacgggccca gctgcgtcta    7080
cattaagcga cggagcagca gccgaagctc ttgtggaatc tagtgaagtt gctgtaatcg    7140
gtttctttaa ggacatggaa tctgattcag ctaaacagtt cctttttagca gctgaagcaa    7200
tcgatgacat ccctttcgga atcacctcaa atagtgacgt gttcagcaag taccaacttg    7260
acaaagatgg agtggtcttg ttcaaaaagt ttgacgaagg cagaaacaat ttcgagggtg    7320
aggttacaaa ggagaaactg cttgatttca ttaaacataa ccaactaccc ttagttatcg    7380
aattcactga acaaactgct cctaagattt tcggtggaga aatcaaaaca catatcttgt    7440
tgttttgcc aaagtccgta tcggattatg aaggtaaact ctccaatttc aaaaaggccg    7500
ctgagagctt taagggcaag attttgttca tctttattga ctcagaccac acagacaatc    7560
agaggatttt ggagttttc ggtttgaaaa aggaggaatg tccagcagtc cgtttgatca    7620
ccttggagga ggagatgacc aaatacaaac cagagtcgga tgagttgact gccgagaaga    7680
taacagaatt ttgtcacaga tttctggaag gtaagatcaa gcctcatctt atgtctcaag    7740
agttgcctga tgactgggat aagcaaccag ttaaagtatt ggtgggtaaa aactttgagg    7800
aagtggcctt cgacgagaaa aaaaatgtct ttgttgaatt ctatgctccg tggtgtggtc    7860
actgtaagca gctggcacca atttgggata aactgggtga aacttacaaa gatcacgaaa    7920
acattgttat tgcaaagatg gacagtactg ctaacgaagt ggaggctgtg aaagttcact    7980
ccttccctac gctgaagttc tttcctgcat ctgctgacag aactgttatc gactataatg    8040
gagagaggac attggatggt tttaaaaagt ttccttgaatc cggaggtcaa gacggagctg    8100
gtgacgacga tgatttggaa gatctggagg aggctgagga acctgatctt gaggaggatg    8160
acgaccagaa ggcagtcaaa gatgaactgg gttctggctc tggttctggc tctatgattt    8220
ggtatatcct agtcgttggt attttgttgc cacagtcact ggctcaccca ggcttcttca    8280
cttctatagg acagatgact gatttgattc acacagaaaa agacctagtt acaagcctta    8340
aagactatat caaagctgaa gaggataagt tggagcaaat caaaaagtgg gcagagaaac    8400
tcgatagatt gactagtact gcaacaaaag atcctgaggg ttttgtgggt cacccagtga    8460
atgctttcaa gctgatgaag agacttaata cagagtggtc agaattggaa aacttggtac    8520
ttaaagatat gagtgatgga ttcatttcta acttaacaat tcaaagacaa tactttccaa    8580
acgatgagga ccaagtagga gcagcaaaag ctttgttgcg attgcaggac acatacaatt    8640
tggacaccga cacgatatcg aagggtgatt tacctggtgt gaagcataag tccttcctca    8700
ctgtggaaga ttgttttgaa ttgggaaaag tcgcatatac agaagccgac tactatcaca    8760
cagaattatg gatggagcaa gctctgcgtc agttggacga aggtgaagtt tctaccgttg    8820
ataaggtttc agttttggat tactatcat acgctgttta ccagcaaggt gatctggaca    8880
aagctctact tttaactaaa aagttgttgg agctggaccc ggagcatcaa agagctaacg    8940
gtaatctgaa atactttgaa tacatcatgg ctaaggaaaa ggacgcaaat aagtcctcgt    9000
```

```
ccgatgacca atccgatcaa aagaccactc tgaaaaaaaa aggtgcagct gttgactacc    9060
tcccagagag acaaaagtat gaaatgctgt gtagaggaga gggtatcaag atgactccaa    9120
ggagacagaa aaagctgttc tgtagatatc atgatgggaa ccgtaaccca aaattcattc    9180
ttgctccagc gaaacaggaa gatgaatggg acaagcctag aatcattcgt tttcatgaca    9240
tcatctccga tgcagaaata gaggttgtga aagacttggc caaaccaaga ttgagtaggg    9300
ctaccgtcca tgaccctgag actggaaaat tgactaccgc acaatatcgt gtctctaaat    9360
cagcatggtt gtccggttac gagaatcccg tggtcagccg tatcaatatg cgtattcaag    9420
atttgactgg tcttgacgta agcactgctg aggaactaca agttgccaac tatggtgtgg    9480
gcggtcagta tgaaccccac tttgatttcg ccagaaagga cgagcctgat gcttttaagg    9540
agctaggtac tggaaataga atcgcaacgt ggttgttcta tatgtccgat gtgcttgctg    9600
gaggagccac agtttteeet gaggtaggtg cttctgtttg gcctaaaaag ggcacggccg    9660
tattttggta caatctgttt gcatctggag aaggtgatta cagcactaga catgctgctt    9720
gtcccgtctt agtcggtaat aagtgggttt ccaataagtg gctgcatgag agaggtcaag    9780
agtttaggag gccatgcaca ttgtcagaat tagaatgata attttacggg aagtctttac    9840
agttttagtt aggagcccct tatatatgaca gtaatgctag tacgttttgt tttgtttaat    9900
taataactta gttatgttta gcctagtata gactccatca attttttttg ttattacgta    9960
agccgcgatg ataatatctg atgaaaaatt cctatcagaa ataatttat caaaagtttc    10020 atgcgatatg agactaagta gaatagggac tcccaaagtg tcagtcacaa gggtc         10075
```

<210> SEQ ID NO 11
<211> LENGTH: 8413
<212> TYPE: DNA
<213> ORGANISM: Artificial Sequence
<220> FEATURE:
<223> OTHER INFORMATION: Synthetic nucleotide

<400> SEQUENCE: 11

```
ggatccttca gtaatgtctt gtttcttttg ttgcagtggt gagccatttt gacttcgtga      60
aagtttcttt agaatagttg tttccagagg ccaaacattc cacccgtagt aaagtgcaag     120
cgtaggaaga ccaagactgg cataaatcag gtataagtgt cgagcactgg caggtgatct     180
tctgaaagtt tctactagca gataagatcc agtagtcatg catatggcaa caatgtaccg     240
tgtggatcta agaacgcgtc ctactaacct tcgcattcgt tggtccagtt tgttgttatc     300
gatcaacgtg acaaggttgt cgattccgcg taagcatgca tacccaagga cgcctgttgc     360
aattccaagt gagccagttc caacaatctt tgtaatatta gagcacttca ttgtgttgcg     420
cttgaaagta aaatgcgaac aaattaagag ataatctcga aaccgcgact tcaaacgcca     480
atatgatgtg cggcacacaa taagcgttca tatccgctgg gtgactttct cgctttaaaa     540
aattatccga aaaaattttc ctctagaatg ggtaaggaaa agactcacgt ttcgaggccg     600
cgattaaatt ccaacatgga tgctgattta tatgggtata aatgggctcg cgataatgtc     660
gggcaatcag gtgcgacaat ctatcgattg tatgggaagc ccgatgcgcc agagttgttt     720
ctgaaacatg gcaaaggtag cgttgccaat gatgttacag atgagatggt cagactaaac     780
tggctgacgg aatttatgcc tcttccgacc atcaagcatt ttatccgtac tcctgatgat     840
gcatggttac tcaccactgc gatccccggc aaaacagcat tccaggtatt agaagaatat     900
cctgattcag gtgaaaatat tgttgatgcg ctggcagtgt tcctgcgccg gttgcattcg     960
```

```
attcctgttt gtaattgtcc ttttaacagc gatcgcgtat ttcgtctcgc tcaggcgcaa    1020
tcacgaatga ataacggttt ggttgatgcg agtgattttg atgacgagcg taatggctgg    1080
cctgttgaac aagtctggaa agaaatgcat aagcttttgc cattctcacc ggattcagtc    1140
gtcactcatg gtgatttctc acttgataac cttatttttg acgaggggaa attaataggt    1200
tgtattgatg ttggacgagt cggaatcgca gaccgatacc aggatcttgc catcctatgg    1260
aactgcctcg gtgagttttc tccttcatta cagaaacggc ttttcaaaa atatggtatt    1320
gataatcctg atatgaataa attgcagttt catttgatgc tcgatgagtt tttctaaaat    1380
tgacacctta cgattattta gagagtattt attagtttta ttgtatgtat acggatgttt    1440
tattatctat ttatgccctt atattctgta actatccaaa agtcctatct tatcaagcca    1500
gcaatctatg tccgcgaacg tcaactaaaa ataagctttt tatgctgttc tctcttttt    1560
tcccttcggt ataattatac cttgcatcca cagattctcc tgccaaattt tgcataatcc    1620
tttacaacat ggctatatgg gagcacttag cgccctccaa aacccatatt gcctacgcat    1680
gtataggtgt ttttccaca atattttctc tgtgctctct tttattaaa gagaagctct    1740
atatcggaga agcttctgtg gccgttatat tcggcttat cgtgggacca cattgcctga    1800
attggtttgc cccggaagat tggggaaact tggatctgat taccttagct gcattaccaa    1860
tgcttaatca gtgaggcacc tatctcagcg atctgtctat ttcgttcatc catagttgcc    1920
tgactccccg tcgtgtagat aactacgata cgggagggct taccatctgg ccccagcgct    1980
gcgatgatac cgcgagaacc acgctcaccg gctccggatt tatcagcaat aaaccagcca    2040
gccggaaggg ccgagcgcag aagtggtcct gcaactttat ccgcctccat ccagtctatt    2100
aattgttgcc gggaagctag agtaagtagt tcgccagtta atagtttgcg caacgttgtt    2160
gccatcgcta caggcatcgt ggtgtcacgc tcgtcgtttg gtatggcttc attcagctcc    2220
ggttcccaac gatcaaggcg agttacatga tcccccatgt tgtgcaaaaa agcggttagc    2280
tccttcggtc ctccgatcgt tgtcagaagt aagttggccg cagtgttatc actcatggtt    2340
atggcagcac tgcataattc tcttactgtc atgccatccg taagatgctt ttctgtgact    2400
ggtgagtact caaccaagtc attctgagaa tagtgtatgc ggcgaccgag ttgctcttgc    2460
ccggcgtcaa tacgggataa taccgcgcca catagcagaa ctttaaaagt gctcatcatt    2520
ggaaaacgtt cttcggggcg aaaactctca aggatcttac cgctgttgag atccagttcg    2580
atgtaaccca ctcgtgcacc caactgatct tcagcatctt ttactttcac cagcgtttct    2640
gggtgagcaa aaacaggaag gcaaaatgcc gcaaaaaagg gaataagggc gacacggaaa    2700
tgttgaatac tcatattctt ccttttcaa tattattgaa gcatttatca gggttattgt    2760
ctcatgagcg gatacatatt tgaatgtatt tagaaaaata aacaaatagg ggtcagtgtt    2820
acaaccaatt aaccaattct gaaggaaga atctgcagga aaagggtacc actgagcgtc    2880
agacccgta gaaagatca aggatcttc ttgagatcct tttttctgc gcgtaatctg    2940
ctgcttgcaa acaaaaaaac caccgctacc agcggtggtt tgtttgccgg atcaagagct    3000
accaactctt tttccgaagg taactggctt cagcagagcg cagataccaa atactgttct    3060
tctagtgtag ccgtagttag gccaccactt caagaactct gtagcaccgc ctacatacct    3120
cgctctgcta atcctgttac cagtggctgc tgccagtggc gataagtcgt gtcttaccgg    3180
gttggaccca agacgatagt taccggataa ggcgcagcgg tcgggctgaa cggggggttc    3240
gtgcacacag cccagcttgg agcgaacgac ctacaccgaa ctgagatacc tacagcgtga    3300
gctatgagaa agcgccacgc ttcccgaagg gagaaaggcg gacaggtatc cggtaagcgg    3360
```

```
cagggtcgga acaggagagc gcacgaggga gcttccaggg ggaaacgcct ggtatcttta   3420
tagtcctgtc gggtttcgcc acctctgact tgagcgtcga ttttttgtgat gctcgtcagg   3480 ggggcggagc ctatggaaaa acgccagcaa cgcggccttt ttacggttcc tggccttttg   3540
ctggcctttt gctcacatgt tttgttcgat tattctccag ataaaatcaa caatagttgt   3600
ttgtaagtaa acgaatcaag atactgaaaa tagtttcaaa agcagatcat ctgggattta   3660
tatatcaggc atcctgcttt agttcttttt tgaacccaaa ggctatctga tgaaaagttg   3720
atataggtat gaagaccaga atttgcctag aggctaaccg agacctgagg ctaaaaaagg   3780
caggaggaaa agtcctgcca aagataggta tttgaacttg ttcgaaaaag gcggaagttt   3840
aaacacatgg ttggagcaag cggcggaata gcggagggat gatacgcagc aaggctggga   3900
tcattcgagt ttcaaggaac gttagctcaa cattcattga ctggtaagcg caactggtt   3960 tcatctgggt ggagttagtc tggtgttggg atgctagttg ttccccacaa ttgaaggcca   4020
gatgaggagg atggtgtggt gataagagat gcaaacagat ggttatggcc ttttgagaac   4080
aaagtagacc tgtcactcaa ttgttgttta tatcattgct atttaaatca ggtgaaccca   4140
cctaactatt tttaactggc atccagtgag ctcgctgggt gaaagccaac catcttttgt   4200
ttcggggaac cgtgctcgcc ccgtaaagtt aattttttt tcccgcgcag ctttaatctt   4260
tcggcagaga aggcgttttc atcgtagcgt gggaacagaa taatcagttc atgtgctata   4320
caggcacatg gcagcagtca ctattttgct ttttaacctt aaagtcgttc atcaatcatt   4380
aactgaccaa tcagattttt tgcatttgcc acttatctaa aaatactttt gtatctcgca   4440
gatacgttca gtggtttcca ggacaacacc caaaaaaagg tatcaatgcc actaggcagt   4500
cggttttatt tttggtcacc cacgcaaaga agcacccacc tcttttaggt tttaagttgt   4560
gggaacagta acaccgccta gagcttcagg aaaaaccagt acctgtgacc gcaattcacc   4620
atgatgcaga atgttaattt aaacgagtgc caaatcaaga tttcaacaga caaatcaatc   4680
gatccatagt tacccattcc agccttttcg tcgtcgagcc tgcttcattc ctgcctcagg   4740
tgcataactt tgcatgaaaa gtccagatta gggcagattt tgagtttaaa ataggaaata   4800
taaacaaata taccgcgaaa aaggtttgtt tatagctttt cgcctggtgc cgtacggtat   4860
aaatacatac tctcctcccc cccctggttc tcttttttctt ttgttactta cattttaccg   4920
ttccgtcact cgcttcactc aacaacaaaa atgttctctc caattttgtc cttggaaatt   4980
attttagctt tggctacttt gcaatctgtc ttcgctcacc caggcttctt cacttctata   5040
ggacagatga ctgatttgat tcacacagaa aaagacctag ttacaagcct taaagactat   5100
atcaaagctg aagaggataa gttggagcaa atcaaaaagt gggcagagaa actcgataga   5160
ttgactagta ctgcaacaaa agatcctgag ggttttgtgg gtcacccagt gaatgctttc   5220
aagctgatga agagacttaa tacagagtgg tcagaattgg aaaacttggt acttaaagat   5280
atgagtgatg gattcatttc taacttaaca attcaaagac aatactttcc aaacgatgag   5340
gaccaagtag gagcagcaaa agctttgttg cgattgcagg acacatacaa tttggacacc   5400
gacacgatat cgaagggtga tttacctggt gtgaagcata agtccttcct cactgtggaa   5460
gattgttttg aattgggaaa agtcgcatat acagaagccg actactatca cacagaatta   5520
tggatggagc aagctctgcg tcagttggac gaaggtgaag tttctaccgt tgataaggtt   5580
tcagttttgg attacttatc atacgctgtt taccagcaag gtgatctgga caaagctcta   5640
cttttaacta aaaagttgtt ggagctggac ccggagcatc aaagagctaa cggtaatctg   5700
```

```
aaatactttg aataacatcat ggctaaggaa aaggacgcaa ataagtcctc gtccgatgac    5760
caatccgatc aaaagaccac tctgaaaaaa aaggtgcag ctgttgacta cctcccagag     5820
agacaaaagt atgaaatgct gtgtagagga gagggtatca agatgactcc aaggagacag   5880
aaaaagctgt tctgtagata tcatgatggg aaccgtaacc caaaattcat tcttgctcca   5940
gcgaaacagg aagatgaatg ggacaagcct agaatcattc gttttcatga catcatctcc   6000
gatgcagaaa tagaggttgt gaaagacttg gccaaaccaa gattgagtag ggctaccgtc   6060
catgaccctg agactggaaa attgactacc gcacaatatc gtgtctctaa atcagcatgg   6120
ttgtccggtt acgagaatcc cgtggtcagc cgtatcaata tgcgtattca agatttgact   6180
ggtcttgacg taagcactgc tgaggaacta caagttgcca actatggtgt gggcggtcag   6240
tatgaacccc actttgattt cgccagaaag gacgagcctg atgctttaa ggagctaggt    6300 actgaaaata gaatcgcaac gtggttgttc tatatgtccg atgtgcttgc tggaggagcc   6360
acagttttcc ctgaggtagg tgcttctgtt tggcctaaaa agggcacggc cgtattttgg   6420
tacaatctgt ttgcatctgg agaaggtgat tacagcacta gacatgctgc ttgtcccgtc   6480
ttagtcggta ataagtgggt ttccaataag tggctgcatg agagaggtca agagtttagg   6540
aggccatgca cattgtcaga attagaaggt tctggctctg gttctggctc tatgagattc   6600
ccatctattt tcaccgctgt cttgttcgct gcctcctctg cattggctgc acccgatgag   6660
gaagatcatg ttttagtatt gcataaagga aatttcgatg aagctttggc cgctcacaaa   6720
tatctgctcg tcgagtttta cgctccctgg tgcggtcatt gtaaggccct tgcaccagag   6780
tacgccaagg cagctggtaa gttaaaggcc gaaggttcag agatcagatt agcaaaagtt   6840
gatgctacag aagagtccga tcttgctcaa caatacgggg ttcgaggata cccaacaatt   6900
aagtttttca aaaatggtga tactgcttcc ccaaaggaat atactgctgg tagagaggca   6960
gacgacatag tcaactggct caaaaagaga acgggcccag ctgcgtctac attaagcgac   7020
ggagcagcag ccgaagctct tgtggaatct agtgaagttg ctgtaatcgg tttctttaag   7080
gacatggaat ctgattcagc taaacagttc cttttagcag ctgaagcaat cgatgacatc   7140
cctttcggaa tcacctcaaa tagtgacgtg ttcagcaagt accaacttga caaagatgga   7200
gtggtcttgt tcaaaaagtt tgacgaaggc agaaacaatt tcgagggtga ggttacaaag   7260
gagaaactgc ttgatttcat taaacataac caactaccct tagttatcga attcactgaa   7320
caaactgctc ctaagatttt cggtggagaa atcaaaacac atatcttgtt gttttttgcca   7380 aagtccgtat cggattatga aggtaaactc tccaatttca aaaaggccgc tgagagcttt   7440
aagggcaaga ttttgttcat ctttattgac tcagaccaca cagacaatca gaggattttg   7500 gagttttttcg gtttgaaaaa ggaggaatgt ccagcagtcc gtttgatcac cttggaggag   7560
gagatgacca aatacaaacc agagtcggat gagttgactg ccgagaagat aacagaattt   7620
tgtcacagat ttctgaaagg taagatcaag cctcatctta tgtctcaaga gttgcctgat   7680
gactgggata agcaaccagt taaagtattg gtgggtaaaa actttgagga agtggccttc   7740
gacgagaaaa aaaatgtctt tgttgaattc tatgctccgt ggtgtggtca ctgtaagcag   7800
ctggcaccaa tttgggataa actgggtgaa acttacaaag atcacgaaaa cattgttatt   7860
gcaaagatgg acagtactgc taacgaagtg gaggctgtga agttcactc cttccctacg   7920 ctgaagttct ttcctgcatc tgctgacaga actgttatcg actataatgg agagaggaca   7980
ttggatggtt ttaaaagtt tcttgaatcc ggaggtcaag acggagctgg tgacgacgat   8040
gatttggaag atctggagga ggctgaggaa cctgatcttg aggaggatga cgaccagaag   8100
```

| | |
|---|---:|
| gcagtcaaag atgaactgtg ataaggggg ccgcgagtcg tgagtaatca agaggatgtc | 8160 |
| agaatgccat tgcctgaga gatgcaggct tcatttttga tacttttta tttgtaacct | 8220 |
| atatagtata ggattttttt tgtcattttg tttcttctcg tacgagcttg ctcctgatca | 8280 |
| gcctatctcg cagctgatga atatcttgtg gtaggggttt gggaaaatca ttcgagtttg | 8340 |
| atgttttct tggtatttcc cactcctctt cagagtacag aagattaagt gagacgttcg | 8400 |
| tttgtgctcc gga | 8413 |

<210> SEQ ID NO 12
<211> LENGTH: 714
<212> TYPE: DNA
<213> ORGANISM: Artificial Sequence
<220> FEATURE:
<223> OTHER INFORMATION: Synthetic nucleotide

<400> SEQUENCE: 12

| | |
|---|---:|
| gtttcttgaa tccggaggtc aagacggagc tggtgacgac gatgatttgg aagatctgga | 60 |
| ggaggctgag gaacctgatc ttgaggagga tgacgaccag aaggcagtca agatgaact | 120 |
| gcatcatcat catcatcatt gataagggg caagaggatg tcagaatgcc atttgcctga | 180 |
| gagatgcagg cttcattttt gatactttt tatttgtaac ctatatagta taggattttt | 240 |
| tttgtcattt tgtttcttct cgtacgagct tgctcctgat cagcctatct cgcagcagat | 300 |
| gaatatcttg tggtaggggt ttgggaaaat cattcgagtt tgatgttttt cttggtattt | 360 |
| cccactcctc ttcagagtac agaagattaa gtgagacctt cgtttgtgcg gttctggctc | 420 |
| tggttctggc tctggatcct tcagtaatgt cttgtttctt ttgttgcagt ggtgagccat | 480 |
| tttgacttcg tgaaagtttc tttagaatag ttgtttccag aggccaaaca ttccacccgt | 540 |
| agtaaagtgc aagcgtagga agaccaagac tggcataaat caggtataag tgtcgagcac | 600 |
| tggcaggtga tcttctgaaa gtttctacta gcagataaga tccagtagtc atgcatatgg | 660 |
| caacaatgta ccgtgtggat ctaagaacgc gtcctactaa ccttcgcatt cgtt | 714 |

<210> SEQ ID NO 13
<211> LENGTH: 7605
<212> TYPE: DNA
<213> ORGANISM: Artificial Sequence
<220> FEATURE:
<223> OTHER INFORMATION: Synthetic nucleotide

<400> SEQUENCE: 13

| | |
|---|---:|
| tgcaggtacc actgagcgtc agaccccgta gaaaagatca aaggatcttc ttgagatcct | 60 |
| ttttttctgc gcgtaatctg ctgcttgcaa acaaaaaaac caccgctacc agcggtggtt | 120 |
| tgtttgccgg atcaagagct accaactctt tttccgaagg taactggctt cagcagagcg | 180 |
| cagataccaa atactgttct tctagtgtag ccgtagttag gccaccactt caagaactct | 240 |
| gtagcaccgc ctacatacct cgctctgcta atcctgttac cagtggctgc tgccagtggc | 300 |
| gataagtcgt gtcttaccgg gttggactca agacgatagt taccggataa ggcgcagcgg | 360 |
| tcgggctgaa cggggggttc gtgcacacag cccagcttgg agcgaacgac ctacaccgaa | 420 |
| ctgagatacc tacagcgtga gctatgagaa agcgccacgc ttcccgaagg gagaaaggcg | 480 |
| gacaggtatc cggtaagcgg cagggtcgga acaggagagc gcacgaggga gcttccaggg | 540 |
| ggaaacgcct ggtatcttta tagtcctgtc gggtttcgcc acctctgact tgagcgtcga | 600 |
| ttttttgtgat gctcgtcagg gggcggagc ctatggaaaa acgccagcaa cgcggccttt | 660 |

```
ttacggttcc tggccttttg ctggcctttt gctcacatgt tctttcctgc ggtacccaga    720
tccaattccc gctttgactg cctgaaatct ccatcgccta caatgatgac atttggattt    780
ggttgactca tgttggtatt gtgaaataga cgcagatcgg gaacactgaa aaatacacag    840
ttattattca tttcagaagc gatagagaga ctgcgctaag cattaatgag attattttg    900 agcattcgtc aatcaatacc aaacaagaca aacggtatgc cgacttttgg aagtttcttt    960
ttgaccaact ggccgttagc atttcaacga accaaactta gttcatcttg gatgagatca   1020
cgcttttgtc atattaggtt ccaagacagc gttaaactg tcagttttgg gccatttggg    1080
gaacatgaaa ctatttgacc ccacactcag aaagccctca tctggagtga tgttcgggtg   1140
taatgcggag cttgttgcat tcggaaataa acaaacatga acctcgccag ggggccagg    1200 atagacaggc taataaagtc atggtgttag tagcctaata aaggaattg gaataaatga    1260 cccttgtgac tgacactttg ggagtcccta ttctacttag tctcatatcg catgaaactt   1320
ttgataaatt attttctgat aggaattttt catcagatat tatcatcgcg gcttacgtaa   1380
taacaaaaaa aattgatgga gtctatacta ggctaacata aactaagtta ttaattaaac   1440
aaaacaaaac gtactagcat tactgtcata tataagggct cctaactaaa actgtaaaga   1500
cttcccgtaa aattatcatt ctaattctga caatgtgcat ggcctcctaa actcttgacc   1560
tctctcatgc agccacttat tggaaaccca cttattaccg actaagacgg gacaagcagc   1620
atgtctagtg ctgtaatcac cttctccaga tgcaaacaga ttgtaccaaa atacggccgt   1680
gcccttttta ggccaaacag aagcacctac ctcagggaaa actgtggctc ctccagcaag   1740
cacatcggac atatagaaca accacgttgc gattctattt ccagtaccta gctccttaaa   1800
agcatcaggc tcgtcctttc tggcgaaatc aaagtggggt tcatactgac cgcccacacc   1860
atagttggca acttgtagtt cctcagcagt gcttacgtca agaccagtca aatcttgaat   1920
acgcatattg atacggctga ccacgggatt ctcgtaaccg acaaccatg ctgatttaga    1980 gacacgatat tgtgcggtag tcaattttcc agtctcaggg tcatggacgg tagccctact   2040
caatcttggt ttggccaagt cttttcacaac ctctatttct gcatcggaga tgatgtcatg  2100
aaaacgaatg attctaggct tgtcccattc atcttcctgt ttcgctggag caagaatgaa   2160
ttttgggtta cggttcccat catgatatct acagaacagc ttttttctgtc tccttggagt  2220 catcttgata ccctctcctc tacacagcat ttcatacttt tgtctctctg ggaggtagtc   2280
aacagctgca ccttttttt tcagagtggt cttttgatcg gattggtcat cggacgagga    2340 cttattgcg tccttttcct tagccatgat gtattcaaag tatttcagat taccgttagc    2400
tctttgatgc tccgggtcca gctccaacaa cttttttagtt aaaagtagag ctttgtccag  2460
atcaccttgc tggtaaacag cgtatgataa gtaatccaaa actgaaacct tatcaacggt   2520
agaaacttca ccttcgtcca actgacgcag agcttgctcc atccataatt ctgtgtgata   2580
gtagtcggct tctgtatatg cgacttttcc caattcaaaa caatcttcca cagtgaggaa   2640
ggacttatgc ttcacaccag gtaaatcacc cttcgatatc gtgtcggtgt ccaaattgta   2700
tgtgtcctgc aatcgcaaca aagcttttgc tgctcctact tggtcctcat cgtttggaaa   2760
gtattgtctt tgaattgtta agttagaaat gaatccatca ctcatatctt taagtaccaa   2820
gttttccaat tctgaccact ctgtattaag tctcttcatc agcttgaaag cattcactgg   2880
gtgacccaca aaaccctcag gatcttttgt tgcagtacta gtcaatctat cgagtttctc   2940
tgcccacttt ttgatttgct ccaacttatc ctcttcagct ttgatatagt ctttaaggct   3000
tgtaactagg tcttttttctg tgtgaatcaa atcagtcatc tgtcctatag aagtgaagaa   3060
```

```
gcctgggtga gccagtgact gtggcaacaa ataccaacg actaggatat accaaatcat      3120
gcggcctgtt gtagttttaa tatagtttga gtatgagatg gaactcagaa cgaaggaatt      3180
atcaccagtt tatatattct gaggaaaggg tgtgtcctaa attggacagt cacgatggca      3240
ataaacgctc agccaatcag aatgcaggag ccataaattg ttgtattatt gctgcaagat      3300
ttatgtgggt tcacattcca ctgaatggtt ttcactgtag aattggtgtc ctagttgtta      3360
tgtttcgaga tgttttcaag aaaaactaaa atgcacaaac tgaccaataa tgtgccgtcg      3420
cgcttggtac aaacgtcagg attgccacca ctttttttcgc actctggtac aaaagttcgc      3480
acttcccact cgtatgtaac gaaaaacaga gcagtctatc cagaacgaga caaattagcg      3540
cgtactgtcc cattccataa ggtatcatag gaaacgagag tcctccccccc atcacgtata      3600 tataaacaca ctgatatccc acatccgctt gtcaccaaac taatacatcc agttcaagtt      3660
acctaaacaa atcaaagcat gagattccca tctattttca ccgctgtctt gttcgctgcc      3720
tcctctgcat tggctgcacc cgatgaggaa gatcatgttt tagtattgca taaggaaat      3780 ttcgatgaag cttttggccgc tcacaaatat ctgctcgtcg agttttacgc tccctggtgc      3840
ggtcattgta aggcccttgc accagagtac gccaaggcag ctggtaagtt aaaggccgaa      3900
ggttcagaga tcagattagc aaaagttgat gctacagaag agtccgatct tgctcaacaa      3960
tacggggttc gaggataccc aacaattaag ttttttcaaaa atggtgatac tgcttcccca      4020
aaggaatata ctgctggtag agaggcagac gacatagtca actggctcaa aaagagaacg      4080
ggcccagctg cgtctacatt aagcgacgga gcagcagccg aagctcttgt ggaatctagt      4140
gaagttgctg taatcggttt ctttaaggac atggaatctg attcagctaa acagttcctt      4200
ttagcagctg aagcaatcga tgacatccct ttcggaatca cctcaaatag tgacgtgttc      4260
agcaagtacc aacttgacaa agatggagtg gtcttgttca aaaagtttga cgaaggcaga      4320
aacaatttcg agggtgaggt tacaaaggag aaactgcttg atttcattaa acataaccaa      4380
ctacccttag ttatcgaatt cactgaacaa actgctccta gattttcgg tggagaaatc      4440 aaaacacata tcttgttgtt tttgccaaag tccgtatcgg attatgaagg taaactctcc      4500
aatttcaaaa aggccgctga gagctttaag ggcaagattt tgttcatctt tattgactca      4560
gaccacacag acaatcagag gattttggag ttttttcggtt tgaaaaagga ggaatgtcca      4620
gcagtccgtt tgatcacctt ggaggaggag atgaccaaat acaaaccaga gtcggatgag      4680
ttgactgccg agaagataac agaattttgt cacagatttc tggaaggtaa gatcaagcct      4740
catcttatgt ctcaagagtt gcctgatgac tgggataagc aaccagttaa agtattggtg      4800
ggtaaaaact ttgaggaagt ggccttcgac gagaaaaaaa atgtctttgt tgaattctat      4860
gctccgtggt gtggtcactg taagcagctg gcaccaattt gggataaact gggtgaaact      4920
tacaaagatc acgaaaacat tgttattgca agatggaca gtactgctaa cgaagtggag      4980
gctgtgaaag ttcactcctt ccctacgctg aagttctttc ctgcatctgc tgacagaact      5040
gttatcgact ataatggaga gaggacattg gatggtttta aaaagtttct tgaatccgga      5100
ggtcaagacg gagctggtga cgacgatgat ttggaagatc tggaggaggc tgaggaacct      5160
gatcttgagg aggatgacga ccagaaggca gtcaaagatg aactgtgata gggggtcaag      5220
aggatgtcag aatgccattt gcctgagaga tgcaggcttc attttttgata cttttttatt      5280 tgtaacctat atagtatagg attttttttg tcattttgtt tcttctcgta cgagcttgct      5340
cctgatcagc ctatctcgca gcagatgaat atcttgtggt aggggtttgg gaaaatcatt      5400
```

```
cgagtttgat gttttctctg gtatttccca ctcctcttca gagtacagaa gattaagtga    5460
gaccttcgtt tgtgcggatc cttcagtaat gtcttgtttc ttttgttgca gtggtgagcc    5520
attttgactt cgtgaaagtt tctttagaat agttgtttcc agaggccaaa cattccaccc    5580
gtagtaaagt gcaagcgtag gaagaccaag actggcataa atcaggtata agtgtcgagc    5640
actggcaggt gatcttctga aagtttctac tagcagataa gatccagtag tcatgcatat    5700
ggcaacaatg taccgtgtgg atctaagaac gcgtcctact aaccttcgca ttcgttggtc    5760
cagtttgttg ttatcgatca acgtgacaag gttgtcgatt ccgcgtaagc atgcataccc    5820
aaggacgcct gttgcaattc caagtgagcc agttccaaca atctttgtaa tattagagca    5880
cttcattgtg ttgcgcttga agtaaaatg cgaacaaatt aagagataat ctcgaaaccg    5940
cgacttcaaa cgccaatatg atgtgcggca cacaataagc gttcatatcc gctgggtgac    6000
tttctcgctt taaaaaatta tccgaaaaaa ttttctagag tgttgacact ttatacttcc    6060
ggctcgtata atacgacaag gtgtaaggag gactaaacca tgggtaaaaa gcctgaactc    6120
accgcgacgt ctgtcgagaa gtttctgatc gaaaagttcg acagcgtctc cgacctgatg    6180
cagctctcgg agggcgaaga atctcgtgct ttcagcttcg atgtaggagg gcgtggatat    6240
gtcctgcggg taaatagctg cgccgatggt ttctacaaag atcgttatgt ttatcggcac    6300
tttgcatcgg ccgcgctccc gattccggaa gtgcttgaca ttggggaatt cagcgagagc    6360
ctgacctatt gcatctcccg ccgtgcacag ggtgtcacgt tgcaagacct gcctgaaacc    6420
gaactgcccg ctgttctgca gccggtcgcg gaggccatgg atgcgatcgc tgcggccgat    6480
cttagccaga cgagcgggtt cggcccattc ggaccgcaag gaatcggtca atacactaca    6540
tggcgtgatt tcatatgcgc gattgctgat ccccatgtgt atcactggca aactgtgatg    6600
gacgacaccg tcagtgcgtc cgtcgcgcag gctctcgatg agctgatgct ttgggccgag    6660
gactgccccg aagtccggca cctcgtgcac gcggatttcg gctccaacaa tgtcctgacg    6720
gacaatggcc gcataacagc ggtcattgac tggagcgagg cgatgttcgg ggattcccaa    6780
tacgaggtcg ccaacatctt cttctggagg ccgtggttgg cttgtatgga gcagcagacg    6840
cgctacttcg agcggaggca tccggagctt gcaggatcgc cgcggctccg gcgtatatg    6900
ctccgcattg gtcttgacca actctatcag agcttggttg acggcaattt cgatgatgca    6960
gcttgggcgc agggtcgatg cgacgcaatc gtccgatccg gagccgggac tgtcgggcgt    7020
acacaaatcg cccgcagaag cgcggccgtc tggaccgatg gctgtgtaga agtactcgcc    7080
gatagtggaa accgacgccc cagcactcgt ccgagggcaa aggaataaca attgacacct    7140
tacgattatt tagagagtat ttattagttt tattgtatgt atacggatgt tttattatct    7200
atttatgccc ttatattctg taactatcca aaagtcctat cttatcaagc cagcaatcta    7260
tgtccgcgaa cgtcaactaa aaataagctt tttatgctct tctctctttt tttcccttcg    7320
gtataattat accttgcatc cacagattct cctgccaaat tttgcataat ccttacaac    7380
atggctatat gggagcactt agcgccctcc aaaacccata ttgcctacgc atgtataggt    7440
gtttttccca caatatttc tctgtgctct cttttattta agagaagct ctatatcgga    7500
gaagcttctg tggccgttat attcggcctt atcgtgggac cacattgcct gaattggttt    7560
gccccggaag attggggaaa cttggatctg attaccttag ctgca               7605
```

<210> SEQ ID NO 14
<211> LENGTH: 7377
<212> TYPE: DNA
<213> ORGANISM: Artificial Sequence
<220> FEATURE:
<223> OTHER INFORMATION: Synthetic nucleotide

<400> SEQUENCE: 14

```
ggatccttca gtaatgtctt gtttcttttg ttgcagtggt gagccatttt gacttcgtga      60
aagtttcttt agaatagttg tttccagagg ccaaacattc cacccgtagt aaagtgcaag     120
cgtaggaaga ccaagactgg cataaatcag gtataagtgt cgagcactgg caggtgatct     180
tctgaaagtt tctactagca gataagatcc agtagtcatg catatggcaa caatgtaccg     240
tgtggatcta agaacgcgtc ctactaacct tcgcattcgt tggtccagtt tgttgttatc     300
gatcaacgtg acaaggttgt cgattccgcg taagcatgca tacccaagga cgcctgttgc     360
aattccaagt gagccagttc caacaatctt tgtaatatta gagcacttca ttgtgttgcg     420
cttgaaagta aaatgcgaac aaattaagag ataatctcga aaccgcgact tcaaacgcca     480
atatgatgtg cggcacacaa taagcgttca tatccgctgg gtgactttct cgctttaaaa     540
aattatccga aaaattttc tagagtgttg ttactttata cttccggctc gtataatacg     600
acaaggtgta aggaggacta aaccatggct aaactcacct ctgctgttcc agtcctgact     660
gctcgtgatg ttgctggtgc tgttgagttc tggactgata ggctcggttt ctcccgtgac     720
ttcgtagagg acgactttgc cggtgttgta cgtgacgacg ttaccctgtt catctccgca     780
gttcaggacc aggttgtgcc agacaacact ctggcatggg tatgggttcg tggtctggac     840
gaactgtacg ctgagtggtc tgaggtcgtg tctaccaact ccgtgatgc atctggtcca     900
gctatgaccg agatcggtga acagccctgg ggtcgtgagt ttgcactgcg tgatccagct     960
ggtaactgcg tgcatttcgt cgcagaagag caggactaac aattgacacc ttacgattat    1020
ttagagagta tttattagtt ttattgtatg tatacggatg ttttattatc tatttatgcc    1080
cttatattct gtaactatcc aaaagtccta tcttatcaag ccagcaatct atgtccgcga    1140
acgtcaacta aaaataagct ttttatgctc ttctctcttt ttttcccttc ggtataatta    1200
taccttgcat ccacagattc tcctgccaaa ttttgcataa tcctttacaa catggctata    1260
tgggagcact tagcgccctc caaaacccat attgcctacg catgtatagg tgttttttcc    1320
acaatatttt ctctgtgctc tctttttatt aaagagaagc tctatatcgg agaagcttct    1380
gtggccgtta tattcggcct tatcgtggga ccacattgcc tgaattggtt tgccccggaa    1440
gattggggaa acttggatct gattaccta gctgcagaaa agggtaccac tgagcgtcag    1500
accccgtaga aaagatcaaa ggatcttctt gagatccttt ttttctgcgc gtaatctgct    1560
gcttgcaaac aaaaaaacca ccgctaccag cggtggtttg tttgccggat caagagctac    1620
caactctttt tccgaaggta actggcttca gcagagcgca gataccaaat actgttcttc    1680
tagtgtagcc gtagttaggc caccacttca agaactctgt agcaccgcct acatacctcg    1740
ctctgctaat cctgttacca gtggctgctg ccagtggcga taagtcgtgt cttaccgggt    1800
tggacccaag acgatagtta ccggataagg cgcagcggtc gggctgaacg ggggggttcgt    1860
gcacacagcc cagcttggag cgaacgacct acaccgaact gagatacta cagcgtgagc    1920
tatgagaaag cgccacgctt cccgaaggga gaaaggcgga caggtatccg gtaagcggca    1980
gggtcggaac aggagagcgc acgagggagc ttccaggggg aaacgcctgg tatctttata    2040
gtcctgtcgg gtttcgccac ctctgacttg agcgtcgatt tttgtgatgc tcgtcagggg    2100
ggcggagcct atgaaaaac gccagcaacg cggccttttt acggttcctg gccttttgct    2160
ggccttttgc tcacatgttt cagaagcgat agagagactg cgctaagcat taatgagatt    2220
```

```
attttttgagc attcgtcaat caataccaaa caagacaaac ggtatgccga cttttggaag    2280 tttcttttg accaactggc cgttagcatt tcaacgaacc aaacttagtt catcttggat     2340
gagatcacgc ttttgtcata ttaggttcca agacagcgtt taaactgtca gttttgggcc    2400
atttggggaa catgaaacta tttgaccca cactcagaaa gccctcatct ggagtgatgt     2460
tcgggtgtaa tgcggagctt gttgcattcg gaaataaaca aacatgaacc tcgccagggg    2520
ggccaggata gacaggctaa taaagtcatg gtgttagtag cctaatagaa ggaattggaa    2580
ataatgtatc taaacgcaaa ctccgagctg gaaaaatgtt accggcgatg cgcggacaat    2640
ttagaggcgg cgatcaagaa acacctgctg ggcgagcagt ctggagcaca gtcttcgatg    2700
ggcccgagat cccaccgcgt tcctgggtac cgggacgtga ggcagcgcga catccatcaa    2760
atataccagg cgccaaccga gtctctcgga aaacagcttc tggatatctt ccgctggcgg    2820
cgcaacgacg aataatagtc cctggaggtg acggaatata tatgtgtgga gggtaaatct    2880
gacagggtgt agcaaaggta atattttcct aaaacatgca atcggctgcc ccgcaacggg    2940
aaaaagaatg actttggcac tcttcaccag agtgggggtgt cccgctcgtg tgtgcaaata    3000
ggctcccact ggtcaccccg attttgcag aaaaacagca agttccgggg tgtctcactg     3060
gtgtccgcca ataagaggag ccggcaggca cggagtctac atcaagctgt ctccgataca    3120
ctcgactacc atccgggtct ctcagagagg ggaatggcac tataaatacc gcctccttgc    3180
gctctctgcc ttcatcaatc aaatcatgtt ctctccaatt ttgtccttgg aaattatttt    3240
agctttggct actttgcaat ctgtcttcgc tcaacaggaa gcagtagatg gtggttgctc    3300
acatttaggt caatcttacg cagatagaga tgtatgaaaa cctgaaccat gtcaaatttg    3360
cgtgtgtgac tcaggttcag tgctctgcga cgatatcata tgtgacgacc aggaattgga    3420
ctgtccaaac ccagagatac cattcggtga atgttgtgct gttttgtccac agccaccaac    3480 tgctcctaca agacctccaa acggtcaagg tccacaaggt cctaaaggtg atccgggtcc    3540
acctggtatt cctggtagaa atggtgaccc tggacctccc ggttcccag gtagcccagg    3600 atcacctggg cctcctggaa tatgtgaatc ctgcccaact ggtggtcaga actatagccc    3660
acaatacgag gcctacgacg tcaaatctgg tgttgctgga ggaggtattg caggctaccc    3720
tggtcccgca gggcccccag gtccgccggg tccgcccgga acatcaggtc atcccggagc    3780
ccctggtgca ccaggttatc agggaccgcc cggagagcct ggacaagctg gtcccgctgg    3840
accccctggt ccaccaggtg ctattggacc aagtggtcct gccggaaaag acggtgaatc    3900
cggtagacct ggtagacccg cgcaaagggg tttcccaggt cctcccggaa tgaagggtcc    3960
agccggtatg cccggttttc ctgggatgaa gggtcacaga ggatttgatg gtagaaacgg    4020
agagaaaggc gaaaccggtg ctcccggact gaagggtgaa aacggtgtcc ctggtgagaa    4080
cggcgctcct ggacctatgg gtccacgtgg tgctccagga gaaagaggca gaccaggatt    4140
gcctggtgca gctggtgcta gaggtaacga tggtgcccgt ggttccgatg gacaacccgg    4200
gccacccggc cctccaggta ccgctggatt tcctggaagc cctggtgcta aggggaggt     4260 tggtccggct ggtagtcccg gaagtagcgg tgccccaggt caaagaggcg aaccaggccc    4320
tcagggtcac gcaggagcac ctggaccgcc tggtcctcct ggttcgaatg gttcgcctgg    4380
aggaaaaggt gaaatggggc ccgcaggaat ccccggtgcg cctggtcta ttggtgccag      4440 gggtcctcca ggcccgccag gtacaaatgg tgtacccgga cagcgaggag cagctggtga    4500
acctggtaaa aacggtgcca aaggagatcc aggtcctcgt ggagagcgtg gtgaagctgg    4560
ctctcccggt atcgccggtc caaaaggtga ggacggtaag gacggttccc ctggtgagcc    4620
```

```
aggtgcgaac ggactgccag gtgcagccgg agagcgagga gtcccaggat tcagggggacc    4680 agccggtgct aacggcttgc ctggtgaaaa agggcccccct ggtgataggg gaggacccgg   4740
tccagcaggc cctcgtggag ttgctggtga gcctggacgt gacggtttac caggagggcc    4800
aggtttgagg ggtattcccg ggtccctgg cggtcctgga tcggatggaa aaccaggggcc    4860 accaggttcg cagggtgaaa caggacgtcc aggcccaccc ggctcacctg gtccaagggg    4920
tcagcctggt gtcatgggtt tccccggtcc aaagggtaat gacggagcac cgggtaaaaa    4980
tggtgaacgt ggtggcccag gtggtccagg accccaaggt ccagctggaa aaaacggtga    5040
gacaggtcct caaggacctc caggacctac cggtcctagc ggagataagg gagatacggg    5100
accgccagga cctcaaggat tgcaaggttt gcctggtaca tctggccctc ccggagaaaa    5160
tggtaagcct ggagagccag gaccaaaagg cgaagctgga gccccaggta tccccggagg    5220
taagggagac tcaggtgctc cgggtgagcg tggtcctccg ggtgccggtg gtccacctgg    5280
acctagaggt ggtgccgggc cgccaggtcc tgaaggtggt aaaggtgctg ctggtccacc    5340
gggaccgcct ggctctgctg gtactcctgg cttgcaggga atgccaggag agagaggtgg    5400
acctggaggt cccggtccga agggtgataa aggggagcca ggatcatccg gtgttgacgg    5460
cgcacctggt aaagacggac caaggggacc aacgggtcca atcggaccac caggacccgc    5520
tggccagcca ggagataaag gcgagtccgg agcaccggt gttcctggta tagctggacc    5580
caggggtggt cccggtgaaa gaggtgaaca gggcccaccg ggtcccgccg gtttccctgg    5640
cgcccctggt caaaatggag aaccaggtgc aaagggcgag agaggagccc caggagaaaa    5700
gggtgaggga ggaccacccg gtgctgccgg tccagctggg ggttcaggtc ctgctggacc    5760
accaggtcca cagggcgtta aaggtgagag aggaagtcca ggtggtcctg gagctgctgg    5820
attcccaggt ggccgtggac ctcctggtcc ccctggatcg aatggtaatc ctggtccgcc    5880
aggtagttcg ggtgctcctg ggaaggacgt tccacctggc cccccaggta gtaacggtgc    5940
acctggtagt ccaggtatat ccggacctaa aggagattcc ggtccaccag gcgaaagagg    6000
ggccccaggc ccacagggtc caccaggagc ccccggtcct ctgggtattg ctggtcttac    6060
tggtgcacgt ggactggccg gtccaccgg aatgcctgga gcaagaggtt cacctggacc    6120
acaaggtatt aaaggagaga acggtaaacc tggaccttcc ggtcaaaacg gagagcgggg    6180 accccaggc ccccaaggtc tgccaggact agctggtacc gcagggggaac caggaagaga    6240 tggaaatcca ggttcagacg gactacccgg tagagatggt gcaccgggg ccaagggcga    6300 cagggtgag aatggatctc ctggtgcgcc agggggcacca ggccacccag gtccccagg    6360 tcctgtgggc cctgctggaa agtcaggtga caggggagag acaggccgg ctggtccatc    6420 tggcgcaccc ggaccagctg gttccagagg cccacctggt ccgcaaggcc ctagaggtga    6480 caagggggagag actggagaac gaggtgctat gggtatcaag ggtcatagag gttttccggg    6540
taatcccggc gccccaggtt ctcctggtcc agctggccat caaggtgcag tcggatcgcc    6600
cggcccagcc ggtcccaggg gccctgttgg tccatccggt cctccaggaa aggatggtgc    6660
ttctggacac ccaggaccta tcggacctcc gggtcctaga ggtaatagag gagaacgtgg    6720
atccgagggt agtcctggtc accctggtca acctggccca ccaggcctc caggtgcacc    6780 cggtccatgt tgtggtgcag gcggtgtggc tgcaattgct ggtgtgggtg ctgaaaaggc    6840
cggcggtttc gctccatatt atggtgatgg ttacattcct gaagctccta gagacgggaca    6900 agcatacgtt agaaaggacg gtgagtgggt gttgctgtcc accttcttag gttctggttc    6960
```

-continued

```
tggttctgat tacaaggatg acgacgataa gggatcgtgt tgcccgggct gctgtggcaa      7020
accaatacct aacccttttac tgggccttga cagtacgtat ccgtatgatg tgccggatta    7080
tgcgcatcac catcatcacc atagatctta atcaagagga tgtcagaatg ccatttgcct    7140
gagagatgca ggcttcattt ttgatacttt tttatttgta acctatatag tataggattt    7200
tttttgtcat tttgtttctt ctcgtacgag cttgctcctg atcagcctat ctcgcagctg    7260
atgaatatct tgtggtaggg gtttgggaaa atcattcgag tttgatgttt ttcttggtat    7320
ttcccactcc tcttcagagt acagaagatt aagtgagacg ttcgtttgtg ctccgga       7377
```

<210> SEQ ID NO 15
<211> LENGTH: 951
<212> TYPE: DNA
<213> ORGANISM: Artificial Sequence
<220> FEATURE:
<223> OTHER INFORMATION: Synthetic nucleotide

<400> SEQUENCE: 15

```
atgagattcc catctatttt caccgctgtc ttgttcgctg cctcctctgc attggctgcc       60
cctgttaaca ctaccactga agacgagact gctcaaattc agctgaagc agttatcggt      120 tactctgacc ttgagggtga tttcgacgtc gctgttttgc cttctctaa ctccactaac      180 aacggttttgt tgttcattaa caccactatc gcttccattg ctgctaagga gagggtgtc    240 tctctcgaga aaagagaggc cgaagctgtg ctgtcaaagt cctgtgtcag tcactttaga    300
aatgttggat ccttgaatag tagggatgtc aatctgaaag atgacttttc ctatgctaat    360
attgatgatc cctataacaa gcctttcgtc ctaaataacc taataaaccc taccaagtgt    420
caagagatca tgcaatttgc caatggcaag ttgtttgact cccaagtcct gagtggcacg    480
gacaagaaca tacgtaactc tcaacaaatg tggatatcca agaacaaccc tatggtaaaa    540 cccatttttcg agaacatatg caggcagttt aacgtaccct ttgataatgc cgaggaccta    600
caggtcgtcc gttacttgcc taatcaatat tataatgagc atcatgactc atgctgtgac    660
tcctccaagc aatgcagtga atttatagag aggggcggtc agaggattct gaccgttta     720 atttacctaa caacgagtt ctcagatgga cacacgtact tccctaattt aaaccaaaag   780
ttcaagccca agactggtga tgcttttggtt ttttaccctt tagccaacaa ctctaataaa    840
tgtcacccat acagtctaca cgcaggtatg cccgtcacgt caggagagaa gtggattgct    900
aatctgtggt tcgtgagcg taagttctcc caccaccacc accaccacta a             951
```

<210> SEQ ID NO 16
<211> LENGTH: 316
<212> TYPE: PRT
<213> ORGANISM: Artificial Sequence
<220> FEATURE:
<223> OTHER INFORMATION: Synthetic peptide

<400> SEQUENCE: 16

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
```

```
                65                  70                  75                  80
Ser Leu Glu Lys Arg Glu Ala Glu Ala Val Leu Ser Lys Ser Cys Val
                    85                  90                  95

Ser His Phe Arg Asn Val Gly Ser Leu Asn Ser Arg Asp Val Asn Leu
                   100                 105                 110

Lys Asp Asp Phe Ser Tyr Ala Asn Ile Asp Asp Pro Tyr Asn Lys Pro
               115                 120                 125

Phe Val Leu Asn Asn Leu Ile Asn Pro Thr Lys Cys Gln Glu Ile Met
130                 135                 140

Gln Phe Ala Asn Gly Lys Leu Phe Asp Ser Gln Val Leu Ser Gly Thr
145                 150                 155                 160

Asp Lys Asn Ile Arg Asn Ser Gln Gln Met Trp Ile Ser Lys Asn Asn
                165                 170                 175

Pro Met Val Lys Pro Ile Phe Glu Asn Ile Cys Arg Gln Phe Asn Val
                180                 185                 190

Pro Phe Asp Asn Ala Glu Asp Leu Gln Val Val Arg Tyr Leu Pro Asn
            195                 200                 205

Gln Tyr Tyr Asn Glu His His Asp Ser Cys Cys Asp Ser Ser Lys Gln
    210                 215                 220

Cys Ser Glu Phe Ile Glu Arg Gly Gly Gln Arg Ile Leu Thr Val Leu
225                 230                 235                 240

Ile Tyr Leu Asn Asn Glu Phe Ser Asp Gly His Thr Tyr Phe Pro Asn
                245                 250                 255

Leu Asn Gln Lys Phe Lys Pro Lys Thr Gly Asp Ala Leu Val Phe Tyr
                260                 265                 270

Pro Leu Ala Asn Asn Ser Asn Lys Cys His Pro Tyr Ser Leu His Ala
            275                 280                 285

Gly Met Pro Val Thr Ser Gly Glu Lys Trp Ile Ala Asn Leu Trp Phe
    290                 295                 300

Arg Glu Arg Lys Phe Ser His His His His His
305                 310                 315

<210> SEQ ID NO 17
<211> LENGTH: 4029
<212> TYPE: DNA
<213> ORGANISM: Artificial Sequence
<220> FEATURE:
<223> OTHER INFORMATION: Synthetic nucleotide

<400> SEQUENCE: 17
ggatccttca gtaatgtctt gtttcttttg ttgcagtggt gagccatttt gacttcgtga      60
aagtttcttt agaatagttg tttccagagg ccaaacattc caccgtagt aaagtgcaag     120 cgtaggaaga ccaagactgg cataaatcag gtataagtgt cgagcactgg caggtgatct    180
tctgaaagtt tctactagca gataagatcc agtagtcatg catatggcaa caatgtaccg    240
tgtggatcta gaacgcgtc ctactaacct tcgcattcgt tggtccagtt tgttgttatc     300
gatcaacgtg acaaggttgt cgattccgcg taagcatgca tacccaagga cgcctgttgc    360
aattccaagt gagccagttc caacaatctt tgtaatatta gagcacttca ttgtgttgcg    420
cttgaaagta aaatgcgaac aaattaagag ataatctcga accgcgact tcaaacgcca     480 atatgatgtg cggcacacaa taagcgttca tatccgctgg gtgactttct cgctttaaaa    540
aattatccga aaaatttttc tagagtgttg ttactttata cttccggctc gtataatacg    600
acaaggtgta aggaggacta aaccatggct aaactcacct ctgctgttcc agtcctgact    660
```

```
gctcgtgatg ttgctggtgc tgttgagttc tggactgata ggctcggttt ctcccgtgac      720
ttcgtagagg acgactttgc cggtgttgta cgtgacgacg ttaccctgtt catctccgca      780
gttcaggacc aggttgtgcc agacaacact ctggcatggg tatgggttcg tggtctggac      840
gaactgtacg ctgagtggtc tgaggtcgtg tctaccaact tccgtgatgc atctggtcca      900
gctatgaccg agatcggtga acagccctgg ggtcgtgagt ttgcactgcg tgatccagct      960
ggtaactgcg tgcatttcgt cgcagaagag caggactaac aattgacacc ttacgattat     1020
ttagagagta tttattagtt ttattgtatg tatacggatg ttttattatc tatttatgcc     1080
cttatattct gtaactatcc aaaagtccta tcttatcaag ccagcaatct atgtccgcga     1140
acgtcaacta aaaataagct ttttatgctc ttctctcttt ttttcccttc ggtataatta     1200
taccttgcat ccacagattc tcctgccaaa ttttgcataa tcctttacaa catggctata     1260
tgggagcact tagcgccctc caaaacccat attgcctacg catgtatagg tgttttttcc     1320
acaatatttt ctctgtgctc tcttttta tt aaagagaagc tctatatcgg agaagcttct     1380
gtggccgtta tattcggcct tatcgtggga ccacattgcc tgaattggtt tgccccggaa     1440
gattggggaa acttggatct gattaccta gctgcagaaa agggtaccac tgagcgtcag     1500
accccgtaga aaagatcaaa ggatcttctt gagatccttt ttttctgcgc gtaatctgct     1560
gcttgcaaac aaaaaaacca ccgctaccag cggtggtttg tttgccggat caagagctac     1620
caactctttt tccgaaggta actggcttca gcagagcgca gataccaaat actgttcttc     1680
tagtgtagcc gtagttaggc caccacttca agaactctgt agcaccgcct acatacctcg     1740
ctctgctaat cctgttacca gtggctgctg ccagtggcga taagtcgtgt cttaccgggt     1800
tggacccaag acgatagtta ccggataagg cgcagcggtc gggctgaacg gggggttcgt     1860
gcacacagcc cagcttggag cgaacgacct acaccgaact gagatacca cagcgtgagc     1920 tatgagaaag cgccacgctt cccgaaggga gaaaggcgga caggtatccg gtaagcggca     1980
gggtcggaac aggagagcgc acgagggagc ttccaggggg aaacgcctgg tatctttata     2040
gtcctgtcgg gtttcgccac ctctgacttg agcgtcgatt tttgtgatgc tcgtcagggg     2100
ggcggagcct atggaaaaac gccagcaacg cggccttttt acggttcctg gccttttgct     2160
ggccttttgc tcacatgtat ttaaataatg tatctaaacg caaactccga gctggaaaaa     2220
tgttaccggc gatgcgcgga caatttagag gcggcgatca agaaacacct gctgggcgag     2280
cagtctggag cacagtcttc gatgggcccg agatcccacc gcgttcctgg gtaccgggac     2340
gtgaggcagc gcgacatcca tcaaatatac caggcgccaa ccgagtgtct cggaaaacag     2400
cttctggata tcttccgctg gcggcgcaac gacgaataat agtccctgga ggtgacggaa     2460
tatatatgtg tggagggtaa atctgacagg gtgtagcaaa ggtaatatt t tcctaaaaca     2520 tgcaatcggc tgccccgcaa cgggaaaaag aatgactttg gcactcttca ccagagtggg     2580
gtgtcccgct cgtgtgtgca aataggctcc cactggtcac cccggatttt gcagaaaaac     2640
agcaagttcc ggggtgtctc actggtgtcc gccaataaga ggagccggca ggcacggagt     2700
ttacatcaag ctgtctccga tacactcgac taccatccgg gtctctcaga gaggggaatg     2760
gcactataaa taccgcctcc ttgcgctctc tgccttcatc aatcaaatca tgagattccc     2820
atctattttc accgctgtct tgttcgctgc ctcctctgca ttggctgccc ctgttaacac     2880
taccactgaa gacagactg ctcaaattcc agctgaagca gttatcggtt actctgacct     2940
tgagggtgat ttcgacgtcg ctgttttgcc tttctctaac tccactaaca acggtttgtt     3000
gttcattaac accactatcg cttccattgc tgctaaggaa gagggtgtct ctctcgagaa     3060
```

```
aagagaggcc gaagctgtgc tgtcaaagtc ctgtgtcagt cactttagaa atgttggatc    3120
cttgaatagt agggatgtca atctgaaaga tgacttttcc tatgctaata ttgatgatcc    3180
ctataacaag cctttcgtcc taaataacct aataaaccct accaagtgtc aagagatcat    3240
gcaatttgcc aatggcaagt tgtttgactc ccaagtcctg agtggcacgg acaagaacat    3300
acgtaactct caacaaatgt ggatatccaa gaacaaccct atggtaaaac ccattttcga    3360
gaacatatgc aggcagttta acgtacccct tgataatgcc gaggacctac aggtcgtccg    3420
ttacttgcct aatcaatatt ataatgagca tcatgactca tgctgtgact cctccaagca    3480
atgcagtgaa tttatagaga ggggcggtca gaggattctg accgttttaa tttacctaaa    3540
caacgagttc tcagatggac acacgtactt tcctaattta aaccaaaagt tcaagcccaa    3600
gactggtgat gctttggttt tttacccttt agccaacaac tctaataaat gtcacccata    3660
cagtctacac gcaggtatgc ccgtcacgtc aggagagaag tggattgcta atctgtggtt    3720
tcgtgagcgt aagttctccc accaccacca ccaccactaa taatcaagag gatgtcagaa    3780
tgccatttgc ctgagagatg caggcttcat ttttgatact tttttatttg taacctatat    3840
agtataggat ttttttttgtc attttgtttc ttctcgtacg agcttgctcc tgatcagcct    3900
atctcgcagc tgatgaatat cttgtggtag gggtttggga aaatcattcg agtttgatgt    3960
ttttcttggt atttcccact cctcttcaga gtacagaaga ttaagtgaga cgttcgtttg    4020
tgctccgga                                                            4029

<210> SEQ ID NO 18
<211> LENGTH: 50
<212> TYPE: DNA
<213> ORGANISM: Artificial Sequence
<220> FEATURE:
<223> OTHER INFORMATION: Synthetic nucleotide

<400> SEQUENCE: 18
ctctgccttc atcaatcaaa tcatgagatt cccatctatt ttcaccgctg                 50

<210> SEQ ID NO 19
<211> LENGTH: 25
<212> TYPE: DNA
<213> ORGANISM: Artificial Sequence
<220> FEATURE:
<223> OTHER INFORMATION: Synthetic nucleotide

<400> SEQUENCE: 19
agcttcggcc tctcttttct cgaga                                           25

<210> SEQ ID NO 20
<211> LENGTH: 55
<212> TYPE: DNA
<213> ORGANISM: Artificial Sequence
<220> FEATURE:
<223> OTHER INFORMATION: Synthetic nucleotide

<400> SEQUENCE: 20
tctcgagaaa agagaggccg aagctgtgct gtcaaagtcc tgtgtcagtc acttt          55

<210> SEQ ID NO 21
<211> LENGTH: 60
<212> TYPE: DNA
<213> ORGANISM: Artificial Sequence
<220> FEATURE:
<223> OTHER INFORMATION: Synthetic nucleotide
```

<400> SEQUENCE: 21

```
gcaaatggca ttctgacatc ctcttgatta gtggtggtgg tggtggtggg agaacttacg    60
```